United States Patent
Juhasz et al.

(10) Patent No.: US 12,245,813 B2
(45) Date of Patent: *Mar. 11, 2025

(54) SYSTEM AND METHOD FOR LOCATING A SURFACE OF OCULAR TISSUE FOR GLAUCOMA SURGERY BASED ON DUAL AIMING BEAMS

(71) Applicant: ViaLase, Inc., Aliso Viejo, CA (US)

(72) Inventors: Tibor Juhasz, San Clemente, CA (US); Ferenc Raksi, Mission Viejo, CA (US); Manu Sharma, Ladera Ranch, CA (US); Hadi Srass, Yorba Linda, CA (US); Carlos G. Suarez, Tustin, CA (US); Guy Holland, San Juan Capistrano, CA (US); Wesley W. Lummis, Rancho Santa Margarita, CA (US); Eric R. Mikula, Aliso Viejo, CA (US); Virginia Lin, Newport Beach, CA (US)

(73) Assignee: ViaLase, Inc., Aliso Viejo, CA (US)

( * ) Notice: Subject to any disclaimer, the term of this patent is extended or adjusted under 35 U.S.C. 154(b) by 90 days.

This patent is subject to a terminal disclaimer.

(21) Appl. No.: 18/085,771

(22) Filed: Dec. 21, 2022

(65) Prior Publication Data

US 2023/0128830 A1     Apr. 27, 2023

Related U.S. Application Data

(63) Continuation of application No. 16/781,770, filed on Feb. 4, 2020, now Pat. No. 11,564,567.

(51) Int. Cl.
*A61B 3/117*     (2006.01)
*A61B 3/10*     (2006.01)
(Continued)

(52) U.S. Cl.
CPC .............. *A61B 3/117* (2013.01); *A61B 3/102* (2013.01); *A61B 3/145* (2013.01); *A61B 3/152* (2013.01);
(Continued)

(58) Field of Classification Search
CPC ......... A61B 3/117; A61B 3/102; A61B 3/145; A61B 3/152; A61B 5/004; A61B 5/0066;
(Continued)

(56) References Cited

U.S. PATENT DOCUMENTS

| 4,423,931 A | 1/1984 | Shapiro |
| 5,123,902 A | 6/1992 | Müller et al. |

(Continued)

FOREIGN PATENT DOCUMENTS

| CN | 104382689 B | 9/2016 |
| DE | 4430720 A1 | 6/1995 |

(Continued)

OTHER PUBLICATIONS

CA3166350 Office Action (Oct. 16, 2023).
(Continued)

*Primary Examiner* — Mohammed A Hasan
(74) *Attorney, Agent, or Firm* — LOZA & LOZA, LLP; David S. Sarisky

(57) ABSTRACT

A target surface in an eye is located using a dual aiming beam apparatus that transmits a first aiming beam of light and a second aiming beam of light. An optics subsystem receives a laser beam from a laser source, the first aiming beam of light, and the second aiming beam of light, and directs the beams of light to be incident with the target surface and aligns the beams of light such that they intersect at a point corresponding to a focus of the laser beam. An imaging apparatus captures an image of the target surface including a first spot corresponding to the first aiming beam (Continued)

of light and a second spot corresponding to a second aiming beam of light. A separation between the spots indicates that the focus is away from the target surface, while overlapping spots indicate the focus is at or on the target surface.

43 Claims, 28 Drawing Sheets

(51) Int. Cl.
*A61B 3/14* (2006.01)
*A61B 3/15* (2006.01)
*A61B 5/00* (2006.01)
*G02B 27/10* (2006.01)
*G02B 27/16* (2006.01)

(52) U.S. Cl.
CPC ............ *A61B 5/004* (2013.01); *A61B 5/0066* (2013.01); *G02B 27/1006* (2013.01); *G02B 27/16* (2013.01)

(58) Field of Classification Search
CPC ................ G02B 27/1006; G02B 27/16; A61F 2009/00851; A61F 2009/00868; A61F 2009/00891; A61F 9/00825
USPC ........................................................ 351/206
See application file for complete search history.

(56) References Cited

U.S. PATENT DOCUMENTS

| | | | |
|---|---|---|---|
| 5,549,596 A | 8/1996 | Latina | |
| 6,004,314 A | 12/1999 | Wei et al. | |
| 6,033,396 A | 3/2000 | Huang et al. | |
| 6,059,772 A | 5/2000 | Hsia et al. | |
| 6,251,103 B1 | 6/2001 | Berlin | |
| 6,482,199 B1 | 11/2002 | Neev | |
| 6,525,875 B1* | 2/2003 | Lauer | G03H 1/0866 359/371 |
| 6,682,523 B2 | 1/2004 | Shadduck | |
| 6,989,007 B2 | 1/2006 | Shadduck | |
| 7,131,968 B2 | 11/2006 | Bendett et al. | |
| 7,192,412 B1 | 3/2007 | Zhou et al. | |
| 7,282,046 B2 | 10/2007 | Simon | |
| 7,351,241 B2 | 4/2008 | Bendett et al. | |
| 7,771,417 B2 | 8/2010 | Telfair et al. | |
| 8,011,504 B1 | 9/2011 | Farberov | |
| 8,171,937 B2 | 5/2012 | Bendett et al. | |
| 8,230,866 B2 | 7/2012 | Hauger et al. | |
| 8,394,084 B2 | 3/2013 | Palankar et al. | |
| 8,523,926 B2 | 9/2013 | Neev | |
| 8,540,659 B2 | 9/2013 | Berlin | |
| 8,568,393 B2 | 10/2013 | Palanker | |
| 8,585,686 B2 | 11/2013 | Bergt et al. | |
| 8,679,089 B2 | 3/2014 | Berlin | |
| 8,687,866 B2 | 4/2014 | Marziliano et al. | |
| 8,709,001 B2 | 4/2014 | Blumenkranz et al. | |
| 8,747,395 B2 | 6/2014 | Rathjen | |
| 8,845,624 B2 | 9/2014 | Raksi et al. | |
| 8,920,407 B2 | 12/2014 | Raksi et al. | |
| 9,028,069 B2 | 5/2015 | Rathjen | |
| 9,033,963 B2 | 5/2015 | Vera et al. | |
| 9,044,303 B2 | 6/2015 | Kurtz et al. | |
| 9,101,448 B2 | 8/2015 | Blumenkranz et al. | |
| 9,259,153 B2 | 2/2016 | Goto | |
| 9,259,354 B2 | 2/2016 | Horvath et al. | |
| 9,265,411 B2 | 2/2016 | Chen et al. | |
| 9,271,870 B2 | 3/2016 | Palanker et al. | |
| 9,301,878 B2 | 4/2016 | Raksi et al. | |
| 9,320,650 B2 | 4/2016 | Bendett et al. | |
| 9,441,946 B2 | 9/2016 | Massow et al. | |
| 9,456,925 B2 | 10/2016 | Kurtz et al. | |
| 9,474,648 B2 | 10/2016 | Palanker et al. | |
| 9,498,295 B2 | 11/2016 | Palanker | |
| 9,517,006 B2 | 12/2016 | Izatt et al. | |
| 9,554,702 B2 | 1/2017 | Papac et al. | |
| 9,560,963 B2 | 2/2017 | Buckland et al. | |
| 9,603,741 B2 | 3/2017 | Berlin | |
| 9,603,744 B2 | 3/2017 | Hailmann et al. | |
| 9,629,750 B2 | 4/2017 | Dambacher et al. | |
| 9,642,746 B2 | 5/2017 | Berlin | |
| 9,681,985 B2 | 6/2017 | Andersen et al. | |
| 9,724,238 B2 | 8/2017 | Heitel | |
| 9,750,640 B2 | 9/2017 | Palanker et al. | |
| 9,820,883 B2 | 11/2017 | Berlin | |
| 9,833,357 B2 | 12/2017 | Berlin | |
| 9,844,464 B2 | 12/2017 | Bendett et al. | |
| 9,936,868 B2 | 4/2018 | Izatt et al. | |
| 10,064,757 B2 | 9/2018 | Berlin | |
| 10,073,515 B2 | 9/2018 | Awdeh | |
| 10,159,600 B2 | 12/2018 | Horvath et al. | |
| 10,159,601 B2 | 12/2018 | Berlin | |
| 10,165,941 B2 | 1/2019 | Walsh et al. | |
| 10,179,066 B2 | 1/2019 | Badawi et al. | |
| 10,195,078 B2 | 2/2019 | Horvath et al. | |
| 10,195,079 B2 | 2/2019 | Horvath et al. | |
| 10,195,080 B2 | 2/2019 | Berlin | |
| 10,238,281 B2 | 3/2019 | Isogai et al. | |
| 10,238,541 B2 | 3/2019 | Yee et al. | |
| 10,292,868 B2 | 5/2019 | Chew et al. | |
| 10,335,314 B2 | 7/2019 | Berlin | |
| 10,335,315 B2 | 7/2019 | Goldshleger et al. | |
| 10,360,683 B2 | 7/2019 | Iwase et al. | |
| 10,362,935 B2 | 7/2019 | Dastmalchi et al. | |
| 10,362,936 B2 | 7/2019 | Buckland et al. | |
| 10,363,169 B2 | 7/2019 | Belkin et al. | |
| 10,363,172 B2 | 7/2019 | Kawai et al. | |
| 10,383,689 B2 | 8/2019 | Berlin | |
| 10,390,883 B2 | 8/2019 | Deladurantaye et al. | |
| 10,398,306 B2 | 9/2019 | Liu | |
| 10,406,034 B2 | 9/2019 | Siegele | |
| 10,426,548 B2 | 10/2019 | Tearney et al. | |
| 10,454,237 B2 | 10/2019 | Yu et al. | |
| 10,456,030 B2 | 10/2019 | Buckland et al. | |
| 10,456,209 B2 | 10/2019 | Peyman | |
| 10,478,060 B2 | 11/2019 | Kubota | |
| 10,493,274 B2 | 12/2019 | Irazoqui et al. | |
| 10,499,809 B2 | 12/2019 | Kalina, Jr. et al. | |
| 10,500,094 B2 | 12/2019 | Buzawa et al. | |
| 10,517,760 B2 | 12/2019 | Berlin | |
| 10,524,822 B2 | 1/2020 | Aljuri et al. | |
| 10,537,476 B2 | 1/2020 | Ha et al. | |
| 10,542,883 B2 | 1/2020 | Gooi et al. | |
| 10,543,122 B2 | 1/2020 | Kahook | |
| 10,543,123 B2 | 1/2020 | Neev | |
| 10,568,763 B2 | 2/2020 | Vera et al. | |
| 10,588,694 B1 | 3/2020 | Neev | |
| 10,596,036 B2 | 3/2020 | Pinchuk | |
| 10,603,214 B2 | 3/2020 | Bigler et al. | |
| 10,603,216 B2 | 3/2020 | Kurtz et al. | |
| 10,653,557 B2 | 5/2020 | Rill et al. | |
| 10,674,906 B2 | 6/2020 | Kalina, Jr. et al. | |
| 10,687,978 B2 | 6/2020 | Berlin | |
| 10,702,416 B2 | 7/2020 | Belkin et al. | |
| 10,744,033 B2 | 8/2020 | Baerveldt et al. | |
| 10,744,034 B2 | 8/2020 | Homer | |
| 10,758,418 B2 | 9/2020 | Vold et al. | |
| 10,765,559 B2 | 9/2020 | Berlin | |
| 10,779,988 B2 | 9/2020 | Fu et al. | |
| 10,799,113 B2 | 10/2020 | Vadakke Matham et al. | |
| 10,821,023 B2 | 11/2020 | Raksi | |
| 10,821,024 B2 | 11/2020 | Raksi | |
| 10,888,461 B2 | 1/2021 | Orthaber et al. | |
| 10,898,381 B2 | 1/2021 | Bendett et al. | |
| 11,019,996 B2 | 6/2021 | Kalina, Jr. et al. | |
| 11,019,997 B2 | 6/2021 | Kalina, Jr. et al. | |
| 11,026,860 B2 | 6/2021 | Andersen et al. | |
| 11,039,958 B2 | 6/2021 | Berlin | |
| 11,110,006 B2 | 9/2021 | Raksi | |
| 11,147,708 B2 | 10/2021 | Horvath et al. | |
| 11,166,630 B2 | 11/2021 | Frisken et al. | |
| 11,173,067 B2 | 11/2021 | Raksi | |
| 11,246,754 B2 | 2/2022 | Holland et al. | |

(56) References Cited

U.S. PATENT DOCUMENTS

| | | |
|---|---|---|
| 11,316,318 B2 | 4/2022 | Yu et al. |
| 11,376,160 B2 | 7/2022 | Romano et al. |
| 11,382,794 B2 | 7/2022 | Sacks et al. |
| 11,395,765 B2 | 7/2022 | Goldshleger et al. |
| 11,399,981 B2 | 8/2022 | Fu et al. |
| 11,564,567 B2 * | 1/2023 | Juhasz .............. A61B 3/117 |
| 11,583,445 B2 | 2/2023 | Raksi |
| 11,759,358 B2 | 9/2023 | Dorin et al. |
| 11,771,596 B2 | 10/2023 | Belkin et al. |
| 11,819,457 B2 | 11/2023 | Berlin |
| 11,826,104 B2 | 11/2023 | Kalina, Jr. et al. |
| 11,833,079 B2 | 12/2023 | Kim |
| 11,833,080 B2 | 12/2023 | Hacker et al. |
| 11,850,186 B2 | 12/2023 | Berlin |
| 11,857,463 B2 | 1/2024 | Berlin |
| 11,877,951 B1 | 1/2024 | Junger et al. |
| 2002/0013572 A1 | 1/2002 | Berlin |
| 2004/0070761 A1 | 4/2004 | Horvath et al. |
| 2006/0200113 A1 | 9/2006 | Haffner et al. |
| 2008/0058781 A1 | 3/2008 | Langeweyde et al. |
| 2009/0012507 A1 | 1/2009 | Culbertson et al. |
| 2009/0093798 A1 | 4/2009 | Charles |
| 2009/0118718 A1 | 5/2009 | Raksi et al. |
| 2009/0149840 A1 | 6/2009 | Kurtz |
| 2009/0149841 A1 | 6/2009 | Kurtz |
| 2009/0157062 A1 * | 6/2009 | Hauger .............. A61B 3/102 |
| | | 606/5 |
| 2009/0185191 A1 | 7/2009 | Boppart et al. |
| 2010/0130966 A1 | 5/2010 | Brownell |
| 2011/0092965 A1 | 4/2011 | Slatkine et al. |
| 2011/0172649 A1 | 7/2011 | Schuele et al. |
| 2011/0202046 A1 | 8/2011 | Angeley et al. |
| 2011/0213664 A1 | 9/2011 | Osterhout et al. |
| 2011/0214082 A1 | 9/2011 | Osterhout et al. |
| 2011/0282190 A1 | 11/2011 | Caffey et al. |
| 2012/0023557 A1 | 1/2012 | Bevan et al. |
| 2012/0075168 A1 | 3/2012 | Osterhout et al. |
| 2012/0257167 A1 | 10/2012 | Gille et al. |
| 2012/0259321 A1 | 10/2012 | Vera et al. |
| 2012/0283557 A1 * | 11/2012 | Berlin .............. A61F 9/009 |
| | | 600/407 |
| 2012/0303007 A1 | 11/2012 | Loesel et al. |
| 2013/0035672 A1 | 2/2013 | Raksi |
| 2013/0085484 A1 | 4/2013 | Van Valen et al. |
| 2013/0103011 A1 | 4/2013 | Grant et al. |
| 2013/0197634 A1 * | 8/2013 | Palanker ........... A61F 9/0084 |
| | | 606/5 |
| 2013/0226160 A1 | 8/2013 | Rathjen |
| 2013/0237972 A1 | 9/2013 | Raksi |
| 2013/0289450 A1 | 10/2013 | Homer |
| 2014/0128853 A1 | 5/2014 | Angeley et al. |
| 2014/0142599 A1 | 5/2014 | Jeglorz et al. |
| 2014/0216468 A1 | 8/2014 | Goldshleger et al. |
| 2014/0236066 A1 | 8/2014 | Horvath et al. |
| 2014/0288485 A1 | 9/2014 | Berlin |
| 2014/0354951 A1 | 12/2014 | Izatt et al. |
| 2015/0077528 A1 | 3/2015 | Awdeh |
| 2015/0080783 A1 | 3/2015 | Berlin |
| 2015/0157505 A1 | 6/2015 | Neev |
| 2015/0202083 A1 | 7/2015 | Takeda et al. |
| 2015/0297408 A1 | 10/2015 | Dolzan et al. |
| 2015/0305939 A1 | 10/2015 | Vera et al. |
| 2015/0305940 A1 | 10/2015 | Vera et al. |
| 2015/0313759 A1 | 11/2015 | Vera et al. |
| 2015/0335477 A1 | 11/2015 | Schuele et al. |
| 2015/0359426 A1 | 12/2015 | Buckland et al. |
| 2016/0095751 A1 | 4/2016 | Berlin |
| 2016/0095752 A1 * | 4/2016 | Srinivasan .......... A61F 9/00834 |
| | | 606/6 |
| 2016/0213512 A1 | 7/2016 | Palanker et al. |
| 2016/0367403 A1 | 12/2016 | Siewert et al. |
| 2017/0020732 A1 | 1/2017 | Berlin |
| 2017/0027437 A1 | 2/2017 | Neal et al. |
| 2017/0042736 A9 | 2/2017 | Berlin |
| 2017/0119579 A9 | 5/2017 | Berlin |
| 2017/0127938 A1 | 5/2017 | Izatt et al. |
| 2017/0202708 A1 | 7/2017 | Berlin |
| 2017/0326003 A1 | 11/2017 | Schuele et al. |
| 2018/0028355 A1 | 2/2018 | Raksi |
| 2018/0207029 A1 | 7/2018 | Herekar et al. |
| 2018/0221205 A1 | 8/2018 | Berlin |
| 2018/0235462 A1 | 8/2018 | Gooi et al. |
| 2018/0360310 A1 | 12/2018 | Berlin |
| 2018/0360655 A1 | 12/2018 | Berlin |
| 2019/0021908 A1 | 1/2019 | Scott |
| 2019/0083313 A1 | 3/2019 | Berlin |
| 2019/0083314 A1 | 3/2019 | Berlin |
| 2019/0117459 A1 | 4/2019 | Berlin |
| 2019/0151146 A1 | 5/2019 | Kim |
| 2019/0240070 A1 | 8/2019 | Schmid et al. |
| 2019/0357768 A1 | 11/2019 | Shareef |
| 2020/0016000 A1 | 1/2020 | Raksi |
| 2020/0016002 A1 | 1/2020 | Raksi |
| 2020/0078216 A1 | 3/2020 | Raksi |
| 2020/0078217 A1 | 3/2020 | Raksi |
| 2020/0078218 A1 | 3/2020 | Holland et al. |
| 2021/0298945 A1 | 9/2021 | Juhasz et al. |

FOREIGN PATENT DOCUMENTS

| | | | |
|---|---|---|---|
| EP | 1080706 A1 * | 3/2001 | ............ A61F 9/008 |
| EP | 1208792 A1 | 5/2002 | |
| EP | 1017308 B1 | 6/2003 | |
| EP | 2384727 A1 | 11/2011 | |
| JP | 58187911 A | 11/1983 | |
| JP | H06319765 A | 11/1994 | |
| JP | 2001070337 A | 3/2001 | |
| JP | 2005508704 A | 4/2005 | |
| JP | 2015163193 A | 9/2015 | |
| JP | 2016504964 A | 2/2016 | |
| JP | 2016105827 A | 6/2016 | |
| JP | 2016193033 A | 11/2016 | |
| JP | 2019000742 A | 1/2019 | |
| WO | 2010060443 A1 | 6/2010 | |
| WO | 2013188885 A1 | 12/2013 | |
| WO | 2017031570 A1 | 3/2017 | |
| WO | 2018049246 A1 | 3/2018 | |
| WO | 2018073625 A1 | 4/2018 | |
| WO | 2018218232 A1 | 11/2018 | |
| WO | 2019060756 A1 | 3/2019 | |
| WO | WO-2019173759 A1 * | 9/2019 | ............... A61F 7/00 |

OTHER PUBLICATIONS

JP2022-546659 Office Action (Sep. 26, 2023).

Lumibird; "Optimis™ Fusion Next Generation SLY/YAG Laser"; Quantel Medical; Cournon d'Auvergne, France; 2020; 6 pgs.

Grant, "Tonographic method for measuring the facility and rate of aqueous flow in human eyes" . Arch. Ophthalmol. 44(2), pp. 204-214 (1950).

Jones et al., "New methods of measuring the rate of aqueous flow in man with fluorescein" . Experimental Eye Research, vol. 5:3, pp. 208-220 (Jul. 1966).

Rosenquist et al., "Ouflow resistance of enucleated human eyes at two different perfusion pressures and different extents of trabeculotomy" . Current Eye Research, vol. 8:12, pp. 1233-1240 (1989).

Brubaker, "Goldmann's equation and clinical measures of aqueous dynamics" . Experimental Eye Research, vol. 78, Issue 3, pp. 633-637 (2004).

Johnstone, "The aqueous outflow system as a mechanical pump: evidence from examination of tissue and aqueous movement in human and non-human primates" . J Glaucoma, vol. 13:5, pp. 421-438 (Oct. 2004).

Junker et al. "Intraoperative optical coherence tomography and ab interno trabecular meshwork surgery with the trabectome." Clin Ophthalmol. 11: 17551760 (Sep. 28, 2017).

Hann et al. "Anatomic changes in schlemm's canal and collector channels in normal and primary open-angle glaucoma eyes using low and high perfusion pressures" . Glaucoma, vol. 55:9 (Sep. 2014).

(56) References Cited

OTHER PUBLICATIONS

Kagemann et al. "Characterisation of Schlemm's canal cross-sectional area." Br J Ophthalmol 2014, 98 (Suppl. II) (Mar. 3, 2014).
McNabb et al. "Complete 360 circumferential gonioscopic optical coherence tomography imaging of the iridocorneal angle." Biomedical Optics Express vol. 6, Issue 4, pp. 1376-1391 (2015).
Xin et al. "Aqueous outflow regulation: optical coherence tomography implicates pressure-dependent tissue motion." Experimental Eye Research, vol. 158, pp. 171-186 (May 2017).
Xin et al. "OCT study of mechanical properties associated with Trabecular meshwork and collector channel motion in human eyes." PLoS One. 2016; 11(9): e0162048. doi: 10.1371/journal.pone.0162048 (Sep. 6, 2016).
PCT/US2021/012981. Int'l Search Report & Written Opinion(Apr. 28, 2021).
PCT/US2021/012981. IPEA Written Report dated (Dec. 23, 2021).

\* cited by examiner

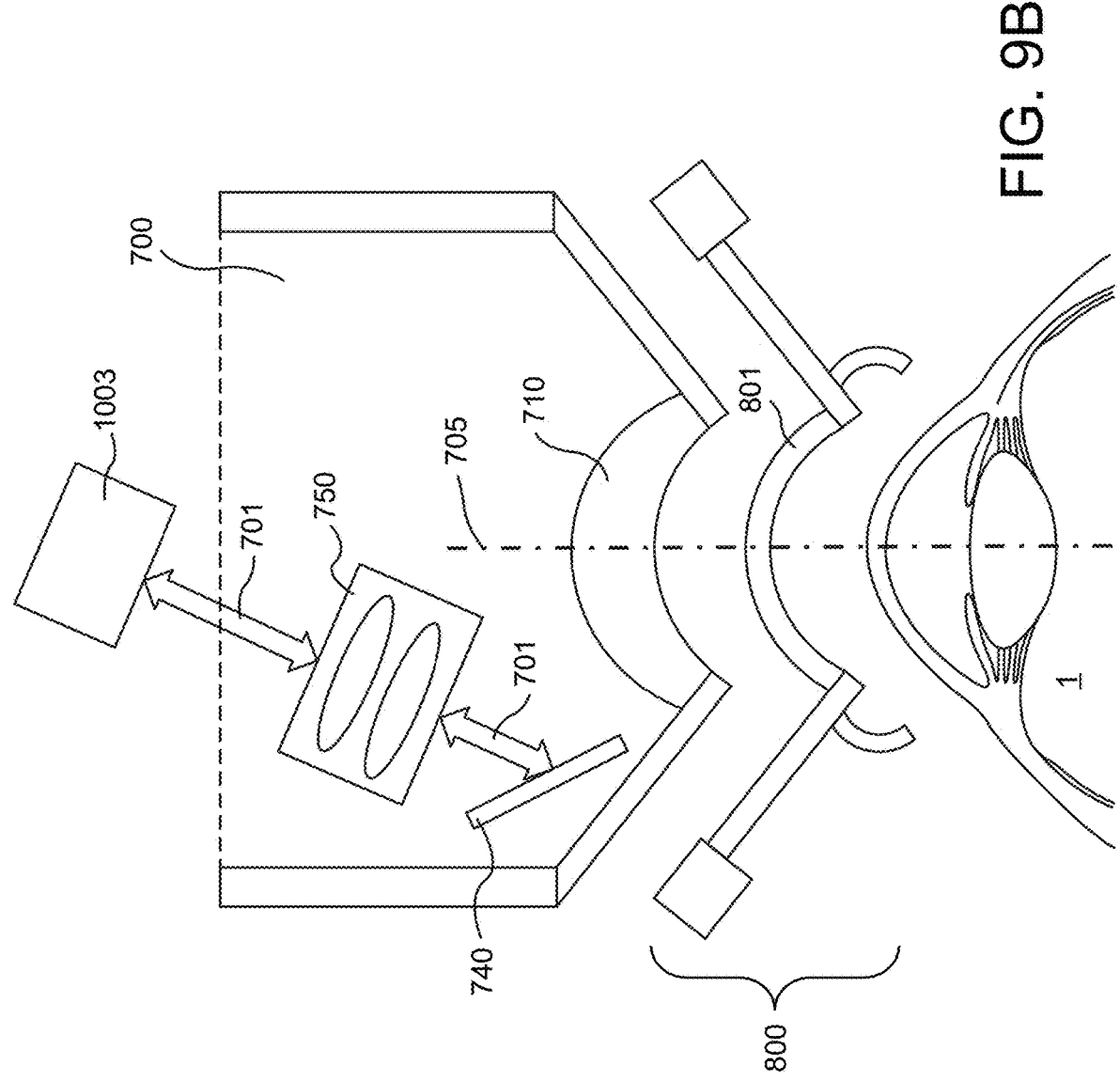

SYSTEM AND METHOD FOR LOCATING A SURFACE OF OCULAR TISSUE FOR GLAUCOMA SURGERY BASED ON DUAL AIMING BEAMS

CROSS-REFERENCE TO RELATED APPLICATION

This application is a continuation of U.S. Application Ser. No. 16/781,770 filed on Feb. 4, 2020, now U.S. Pat. No. 11,564,567, entitled "System and Method for Locating a Surface of Ocular Tissue for Glaucoma Surgery Based on Dual Aiming Beams," which is expressly incorporated by reference herein in its entirety.

TECHNICAL FIELD

The present disclosure relates generally to the field of medical devices and treatment of diseases in ophthalmology including glaucoma, and more particularly to systems and methods for locating a surface of ocular tissue based on dual aiming beams.

BACKGROUND

Before describing the different types of glaucoma and current diagnosis and treatments options, a brief overview of the anatomy of the eye is provided.
Anatomy of the Eye With reference to FIGS. 1-3, the outer tissue layer of the eye 1 includes a sclera 2 that provides the structure of the eye's shape. In front of the sclera 2 is a cornea 3 that is comprised of transparent layers of tissue that allow light to enter the interior of the eye. Inside the eye 1 is a crystalline lens 4 that is connected to the eye by fiber zonules 5, which are connected to the ciliary body 6. Between the crystalline lens 4 and the cornea 3 is an anterior chamber 7 that contains a flowing clear liquid called aqueous humor 8. Encircling the perimeter of the crystalline lens 4 is an iris 9 which forms a pupil around the approximate center of the crystalline lens. A posterior chamber 23 is an annular volume behind the iris 9 and bounded by the ciliary body 6, fiber zonules 5, and the crystalline lens 4. The vitreous humor 10 is located between the crystalline lens 4 and the retina 11. Light entering the eye is optically focused through the cornea 3 and crystalline lens.

With reference to FIG. 2, the corneoscleral junction of the eye is the portion of the anterior chamber 7 at the intersection of the iris 9, the sclera 2, and the cornea 3. The anatomy of the eye 1 at the corneoscleral junction includes a trabecular meshwork 12. The trabecular meshwork 12 is a fibrous network of tissue that encircles the iris 9 within the eye 1. In simplified, general terms the tissues of the corneoscleral junction are arranged as follows: the iris 9 meets the ciliary body 6, the ciliary body meets with the underside of the scleral spur 14, the top of the scleral spur serves as an attachment point for the bottom of the trabecular meshwork 12. The ciliary body is present mainly in the posterior chamber, but also extends into the very corner of the anterior chamber 7. The network of tissue layers that make up the trabecular meshwork 12 are porous and thus present a pathway for the egress of aqueous humor 8 flowing from the anterior chamber 7. This pathway may be referred to herein as an aqueous humor outflow pathway, an aqueous outflow pathway, or simply an outflow pathway.

Referring to FIG. 3, the pathway formed by the pores in the trabecular meshwork 12 connect to a set of thin porous tissue layers called the uveal meshwork 15, the corneoscleral meshwork 16, and the juxtacanalicular tissue 17. The juxtacanalicular tissue 17, in turn, abuts a structure called Schlemm's canal 18. The Schlemm's canal 18 carries a mixture of aqueous humor 8 and blood from the surrounding tissue to drain into the venous system though a system of collector channels 19. As shown in FIG. 2, the vascular layer of the eye, referred to as the choroid 20, is next to the sclera 2. A space, called the suprachoroidal space 21, may be present between the choroid 20 and the sclera 2. The general region near the periphery of the wedge between the cornea 3 and the iris 9, running circumferentially is called the irido-corneal angle 13. The irido-corneal angle 13 may also be referred to as the corneal angle of the eye or simply the angle of the eye. The ocular tissues illustrated in FIG. 3 are all considered to be within the irido-corneal angle 13.

With reference to FIG. 4, two possible outflow pathways for the movement of aqueous humor 8 include a trabecular outflow pathway 40 and a uveoscleral outflow pathway 42. Aqueous humor 8, which is produced by the ciliary body 6, flows from the posterior chamber 23 through the pupil into the anterior chamber 7, and then exits the eye through one or more of the two different outflow pathways 40, 42. Approximately 90% of the aqueous humor 8 leaves via the trabecular outflow pathway 40 by passing through the trabecular meshwork 12, into the Schlemm's canal 18 and through one or more plexus of collector channels 19 before draining through a drain path 41 into the venous system. Any remaining aqueous humor 8 leaves primarily through the uveoscleral outflow pathway 42. The uveoscleral outflow pathway 42 passes through the ciliary body 6 face and iris root into the suprachoroidal space 21 (shown in FIG. 2). Aqueous humor 8 drains from the suprachoroidal space 21, from which it can be drained through the sclera 2.

The intra-ocular pressure of the eye depends on the aqueous humor 8 outflow through the trabecular outflow pathway 40 and the resistance to outflow of aqueous humor through the trabecular outflow pathway. The intra-ocular pressure of the eye is largely independent of the aqueous humor 8 outflow through the uveoscleral outflow pathway 42. Resistance to the outflow of aqueous humor 8 through the trabecular outflow pathway 40 may lead to elevated intra-ocular pressure of the eye, which is a widely recognized risk factor for glaucoma. Resistance through the trabecular outflow pathway 40 may increase due a collapsed or malfunctioning Schlemm's canal 18 and trabecular meshwork 12.

Referring to FIG. 5, as an optical system, the eye 1 is represented by an optical model described by idealized centered and rotationally symmetrical surfaces, entrance and exit pupils, and six cardinal points: object and image space focal points, first and second principal planes, and first and second nodal points. Angular directions relative to the human eye are often defined with respect to an optical axis 24, a visual axis 26, a pupillary axis 28 and a line of sight 29 of the eye. The optical axis 24 is the symmetry axis, the line connecting the vertices of the idealized surfaces of the eye. The visual axis 26 connects the foveal center 22 with the first and second nodal points to the object. The line of sight 29 connects the fovea through the exit and entrance pupils to the object. The pupillary axis 28 is normal to the anterior surface of the cornea 3 and directed to the center of the entrance pupil. These axes of the eye differ from one another only by a few degrees and fall within a range of what is generally referred to as the direction of view.

Glaucoma

Glaucoma is a group of diseases that can harm the optic nerve and cause vision loss or blindness. It is the leading cause of irreversible blindness. Approximately 80 million people are estimated to have glaucoma worldwide and of these, approximately 6.7 million are bilaterally blind. More than 2.7 million Americans over age 40 have glaucoma. Symptoms start with loss of peripheral vision and can progress to blindness.

There are two forms of glaucoma, one is referred to as closed-angle glaucoma, the other as open-angled glaucoma. With reference to FIGS. 1-4, in closed-angle glaucoma, the iris 9 in a collapsed anterior chamber 7 may obstruct and close off the flow of aqueous humor 8. In open-angle glaucoma, which is the more common form of glaucoma, the permeability of ocular tissue may be affected by irregularities in the juxtacanalicular tissue 17 and inner wall of Schlemm's canal 18a, blockage of tissue in the irido-corneal angle 13 along the trabecular outflow pathway 40.

As previously stated, elevated intra-ocular pressure (IOP) of the eye, which damages the optic nerve, is a widely recognized risk factor for glaucoma. However, not every person with increased eye pressure will develop glaucoma, and glaucoma can develop without increased eye pressure. Nonetheless, it is desirable to reduce elevated TOP of the eye to reduce the risk of glaucoma.

Methods of diagnosing conditions of the eye of a patient with glaucoma include visual acuity tests and visual field tests, dilated eye exams, tonometry, i.e. measuring the intra-ocular pressure of the eye, and pachymetry, i.e. measuring the thickness of the cornea. Deterioration of vision starts with the narrowing of the visual field and progresses to total blindness. Imaging methods include slit lamp examination, observation of the irido-corneal angle with a gonioscopic lens and optical coherence tomography (OCT) imaging of the anterior chamber and the retina Once diagnosed, some clinically proven treatments are available to control or lower the intra-ocular pressure of the eye to slow or stop the progress of glaucoma. The most common treatments include: 1) medications, such as eye drops or pills, 2) laser surgery, and 3) traditional surgery. Treatment usually begins with medication. However, the efficacy of medication is often hindered by patient non-compliance. When medication does not work for a patient, laser surgery is typically the next treatment to be tried. Traditional surgery is invasive, more high risk than medication and laser surgery, and has a limited time window of effectiveness. Traditional surgery is thus usually reserved as a last option for patients whose eye pressure cannot be controlled with medication or laser surgery.

Laser Surgery

With reference to FIG. 2, laser surgery for glaucoma targets the trabecular meshwork 12 to decrease aqueous humor 8 flow resistance. Common laser treatments include Argon Laser Trabeculoplasty (ALT), Selective Laser Trabeculoplasty (SLT) and Excimer Laser Trabeculostomy (ELT).

ALT was the first laser trabeculoplasty procedure. During the procedure, an argon laser of 514 nm wavelength is applied to the trabecular meshwork 12 around 180 degrees of the circumference of the irido-corneal angle 13. The argon laser induces a thermal interaction with the ocular tissue that produces openings in the trabecular meshwork 12. ALT, however, causes scarring of the ocular tissue, followed by inflammatory responses and tissue healing that may ultimately close the opening through the trabecular meshwork 12 formed by the ALT treatment, thus reducing the efficacy of the treatment. Furthermore, because of this scarring, ALT therapy is typically not repeatable.

SLT is designed to lower the scarring effect by selectively targeting pigments in the trabecular meshwork 12 and reducing the amount of heat delivered to surrounding ocular tissue. During the procedure, a solid-state laser of 532 nm wavelength is applied to the trabecular meshwork 12 between 180 to 360 degrees around the circumference of the irido-corneal angle 13 to remove the pigmented cells lining the trabeculae which comprise the trabecular meshwork. The collagen ultrastructure of the trabecular meshwork is preserved during SLT. 12. SLT treatment can be repeated, but subsequent treatments have lower effects on TOP reduction.

ELT uses a 308 nm wavelength ultraviolet (UV) excimer laser and non-thermal interaction with ocular tissue to treat the trabecular meshwork 12 and inner wall of Schlemm's canal in a manner that does not invoke a healing response. Therefore, the TOP lowering effect lasts longer. However, because the UV light of the laser cannot penetrate deep into the eye, the laser light is delivered to the trabecular meshwork 12 via an optical fiber inserted into the eye 1 through an opening and the fiber is brought into contact with the trabecular meshwork. The procedure is highly invasive and is generally practiced simultaneously with cataract procedures when the eye is already surgically open. Like ALT and SLT, ELT also lacks control over the amount of TOP reduction.

None of these existing laser treatments represents an ideal treatment for glaucoma. Accordingly, what is needed are systems, apparatuses, and method for laser surgery treatment of glaucoma that effectively reduce TOP non-invasively without significant scarring of tissue, so the treatment may be completed in a single procedure and repeated at a later time if necessary. U.S. patent application Ser. No. 16/036,883, entitled Integrated Surgical System and Method for Treatment in the Irido-Corneal Angle of the Eye, and U.S. patent application Ser. No. 16/125,588, entitled Non-Invasive and Minimally Invasive Laser Surgery for the Reduction Of Intraocular Pressure in the Eye Systems, each of which is assigned to the assignee of the present application and is hereby incorporated by reference, disclose laser treatment systems that reduce IOP non-invasively through photodisruption by, for example, a femtosecond laser that provides highly localized, non-thermal photo-disruptive laser-tissue interaction with minimal collateral damage to surrounding ocular tissue.

Such photo-disruptive laser treatment requires the locating of specific structures of ocular tissue in the irido-corneal angle for laser focus placement. For example, during glaucoma surgery with a femtosecond laser, apertures or canals may be created in the trabecular meshwork by placing the focus of femtosecond laser on the surface of the trabecular meshwork facing the anterior chamber and photodisrupting the ocular tissue between the surface and the inner wall of Schlemm's canal. However, accurately locating the surface of the trabecular meshwork and placing the femtosecond laser focus onto that surface is difficult. In some known glaucoma laser treatments, a surgical device may incorporate a single aiming beam that is co-linear with a treatment surgical laser beam. The single aiming beam may mark the location of the surgical laser beam that is incident on a target surface. This technique, however, is ineffective for laser treatments that require a focused beam placed onto the surface of target tissue, such as required by photo-disruptive laser treatments. U.S. Pat. No. 6,033,396 discloses a system that uses two aiming lasers to center a laser projection pattern on a pupil aperture of an eye during laser thermal keratoplasty. This system, however, does not place the focus of the treatment laser on the cornea based on the two aiming lasers. Accordingly, what is needed in the field of laser treatment of glaucoma are systems and methods that enable the detection of a surface of ocular tissue. What is further needed and desired, are systems and methods that enable placement of a focus of a femtosecond laser on the surface of ocular tissue based on, e.g., simultaneous with, the detection of such surface.

SUMMARY

The present disclosure relates to a systems for locating a target surface of ocular tissue in an irido-corneal angle of an eye for photodisruption by a laser. In one implementation, the system includes a laser source configured to output a laser beam, and a dual aiming beam apparatus configured to transmit a first aiming beam of light and a second aiming beam of light. The system also include an optics subsystem optically aligned with the laser source and the dual aiming beam apparatus to receive the laser beam, the first aiming beam of light, and the second aiming beam of light. The optics subsystem includes a focusing objective configured to direct the first aiming beam of light and the second aiming beam of light to be incident with the target surface and to align the first aiming beam of light and the second aiming beam of light relative to each other and relative to the laser beam such that the first aiming beam of light and the second aiming beam of light intersect at a point corresponding to a focus of the laser beam. The intersection point of the first aiming beam of light and the second aiming beam of light may be at a location that is the same as the location of the focus of the laser beam. The intersection point of the first aiming beam of light and the second aiming beam of light may be at a location different from the location of the focus of the laser beam. For example, the intersection point may be slightly offset from the focus. The system further includes an imaging apparatus optically aligned with the optics subsystem to capture an image of the irido-corneal angle including a first spot corresponding to the first aiming beam of light and a second spot corresponding to a second aiming beam of light.

In another implementation, the system includes a laser source configured to output a laser beam, a dual aiming beam apparatus configured to transmit a first aiming beam of light and a second aiming beam of light, and an OCT imaging apparatus configured to output an OCT beam and optically aligned to capture one or more OCT images of the irido-corneal angle. The system further includes an optics subsystem optically aligned with the laser source, the dual aiming beam apparatus, and the OCT imaging apparatus to receive the laser beam, the first aiming beam of light, the second aiming beam of light, and the OCT beam. The optics subsystem includes a focusing objective configured to direct the first aiming beam of light, the second aiming beam of light, and the OCT beam to be incident with the target surface and to align the first aiming beam of light, the second aiming beam of light and the OCT beam relative to each other and relative to the laser beam such that the first aiming beam of light, the second aiming beam of light, and the OCT beam intersect at a point corresponding to a focus of the laser beam. The intersection point of the first aiming beam of light, the second aiming beam of light, and the OCT beam may be at a location that is the same as the location of the focus of the laser beam. The intersection point of the first aiming beam of light, the second aiming beam of light, and the OCT beam may be at a location different from the location of the focus of the laser beam. For example, the intersection point may be slightly offset from the focus. The system further includes an imaging apparatus optically aligned with the optics subsystem to capture an image of the irido-corneal angle including a first spot corresponding to the first aiming beam of light and a second spot corresponding to a second aiming beam of light.

The present disclosure also relates to methods of locating a target surface of ocular tissue in an irido-corneal angle of an eye for photodisruption by a laser. In one implementation, the method includes directing a first aiming beam of light and a second aiming beam of light to be incident with the target surface. The first aiming beam of light and the second aiming beam of light are aligned relative to each other and relative to a laser beam such that the first aiming beam of light and the second aiming beam of light intersect at a point relative to a focus of the laser beam. The intersection point of the first aiming beam of light and the second aiming beam of light may be at a location that is the same as the location of the focus of the laser beam. The intersection point of the first aiming beam of light and the second aiming beam of light may be at a location different from the location of the focus of the laser beam. The method further includes capturing an image of a first spot corresponding to the first aiming beam of light and a second spot corresponding to a second aiming beam of light.

In another implementation, the method includes directing an OCT beam, a first aiming beam of light and a second aiming beam of light to be incident with the target surface. The OCT beam, the first aiming beam of light and the second aiming beam of light are aligned relative to each other and relative to a laser beam such that the OCT beam, the first aiming beam of light and the second aiming beam of light intersect at a point corresponding to a focus of the laser beam. The intersection point of the first aiming beam of light, the second aiming beam of light, and the OCT beam may be at a location that is the same as the location of the focus of the laser beam. The intersection point of the first aiming beam of light, the second aiming beam of light, and the OCT beam may be at a location different from the location of the focus of the laser beam. The method further includes capturing an image of a first spot corresponding to the first aiming beam of light and a second spot corresponding to a second aiming beam of light; and capturing one or more OCT images of the irido-corneal angle.

It is understood that other aspects of apparatuses and methods will become apparent to those skilled in the art from the following detailed description, wherein various aspects of apparatuses and methods are shown and described by way of illustration. As will be realized, these aspects may be implemented in other and different forms and its several details are capable of modification in various other respects. Accordingly, the drawings and detailed description are to be regarded as illustrative in nature and not as restrictive.

BRIEF DESCRIPTION OF THE DRAWINGS

Various aspects of systems and methods will now be presented in the detailed description by way of example, and not by way of limitation, with reference to the accompanying drawings, wherein:

FIGS. 9A and 9B are schematic illustrations of the focusing objective of the integrated surgical system of FIG. 7 coupled to (FIG. 9A) and decoupled from (FIG. 9B) the patient interface of the integrated surgical system of FIG. 7.

DETAILED DESCRIPTION

Figure 1:
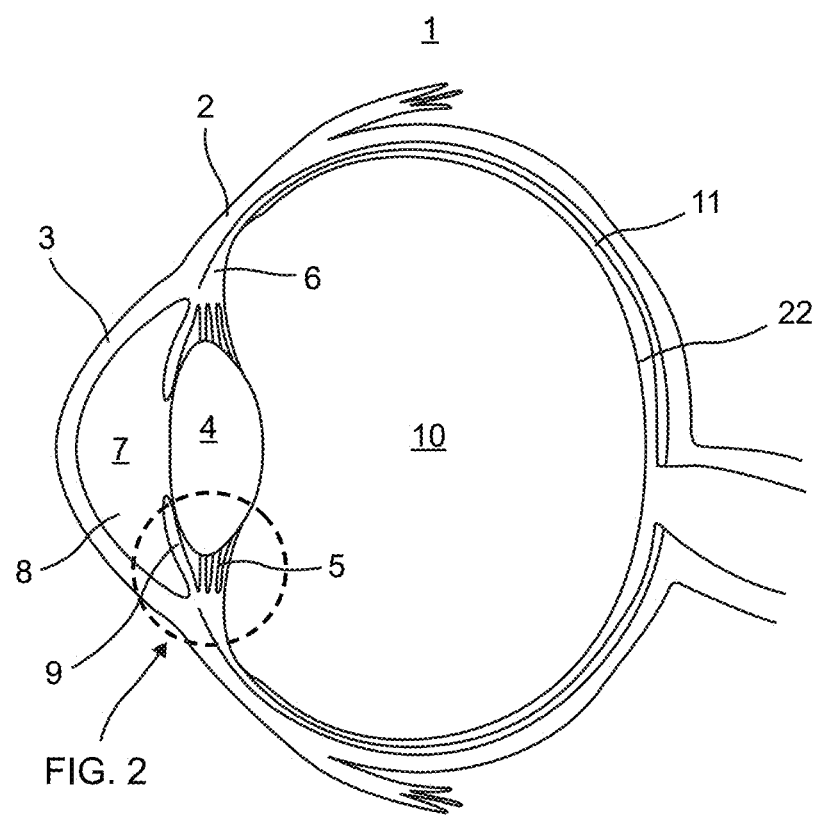
FIG. 1 is a sectional schematic illustration of a human eye and its interior anatomical structures.
Figure 2:
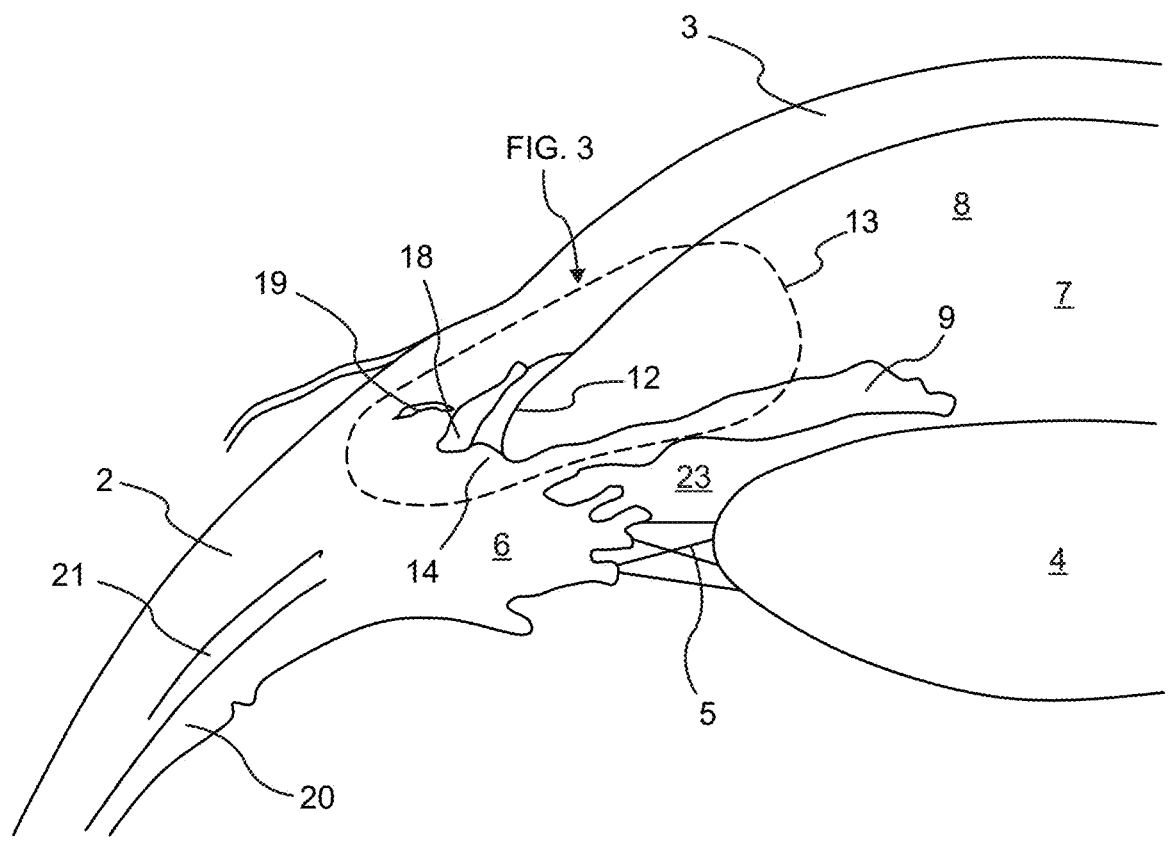
FIG. 2 is a sectional schematic illustration of the irido-corneal angle of the eye of FIG. 1.
Figure 3:
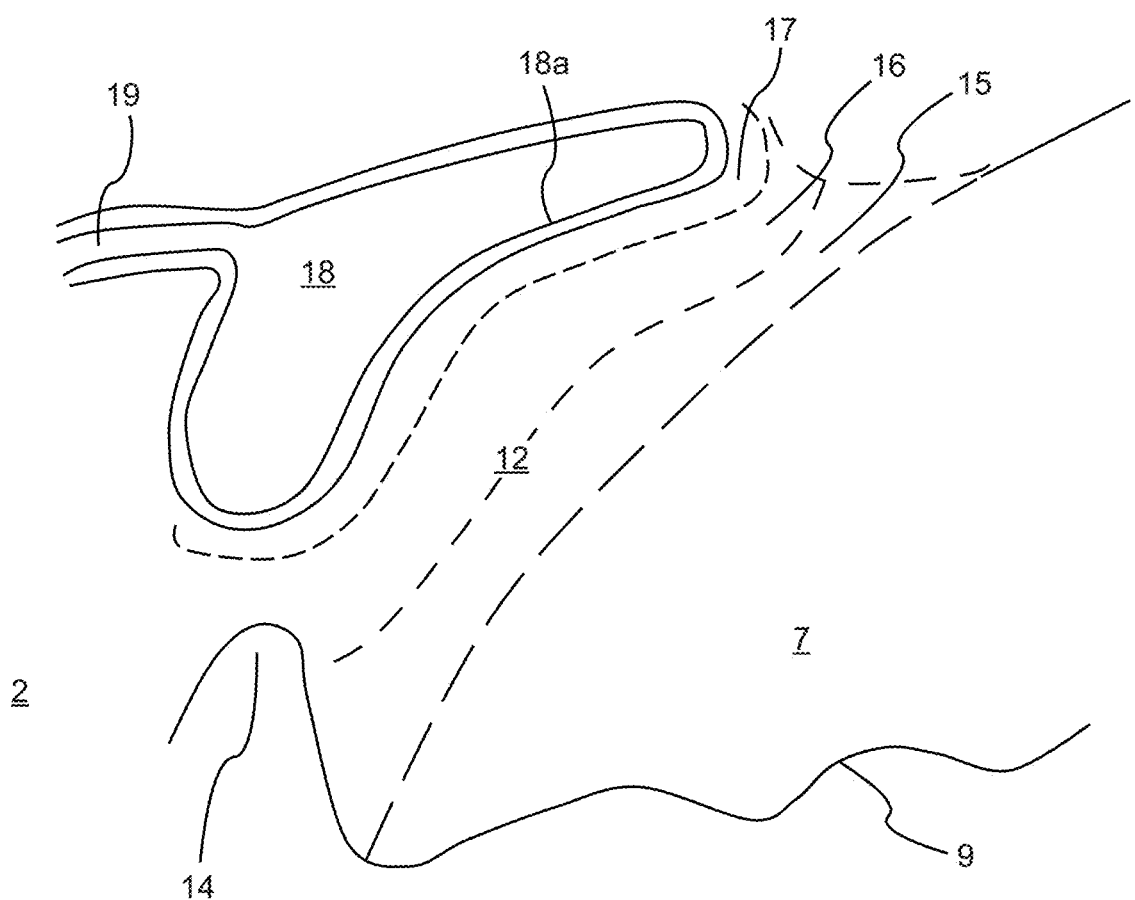
FIG. 3 is a sectional schematic illustration detailing anatomical structures in the irido-corneal angle of FIG. 2, including the trabecular meshwork, Schlemm's canal, and one or more collector channels branching from the Schlemm's canal.
Figure 4:
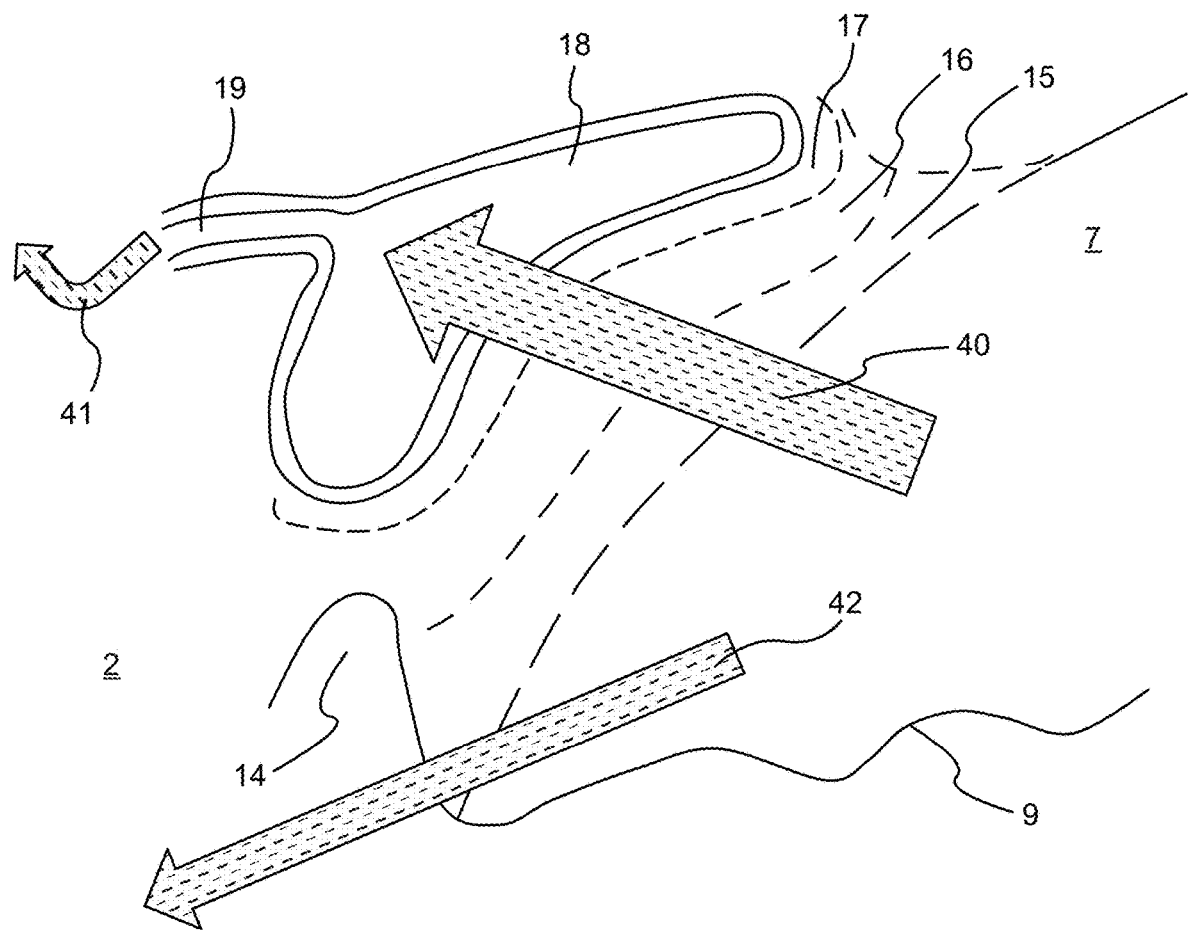
FIG. 4 is a sectional schematic illustration of various outflow pathways for aqueous humor through the trabecular meshwork, Schlemm's canal, and collector channels of FIG. 3.
Figure 5:
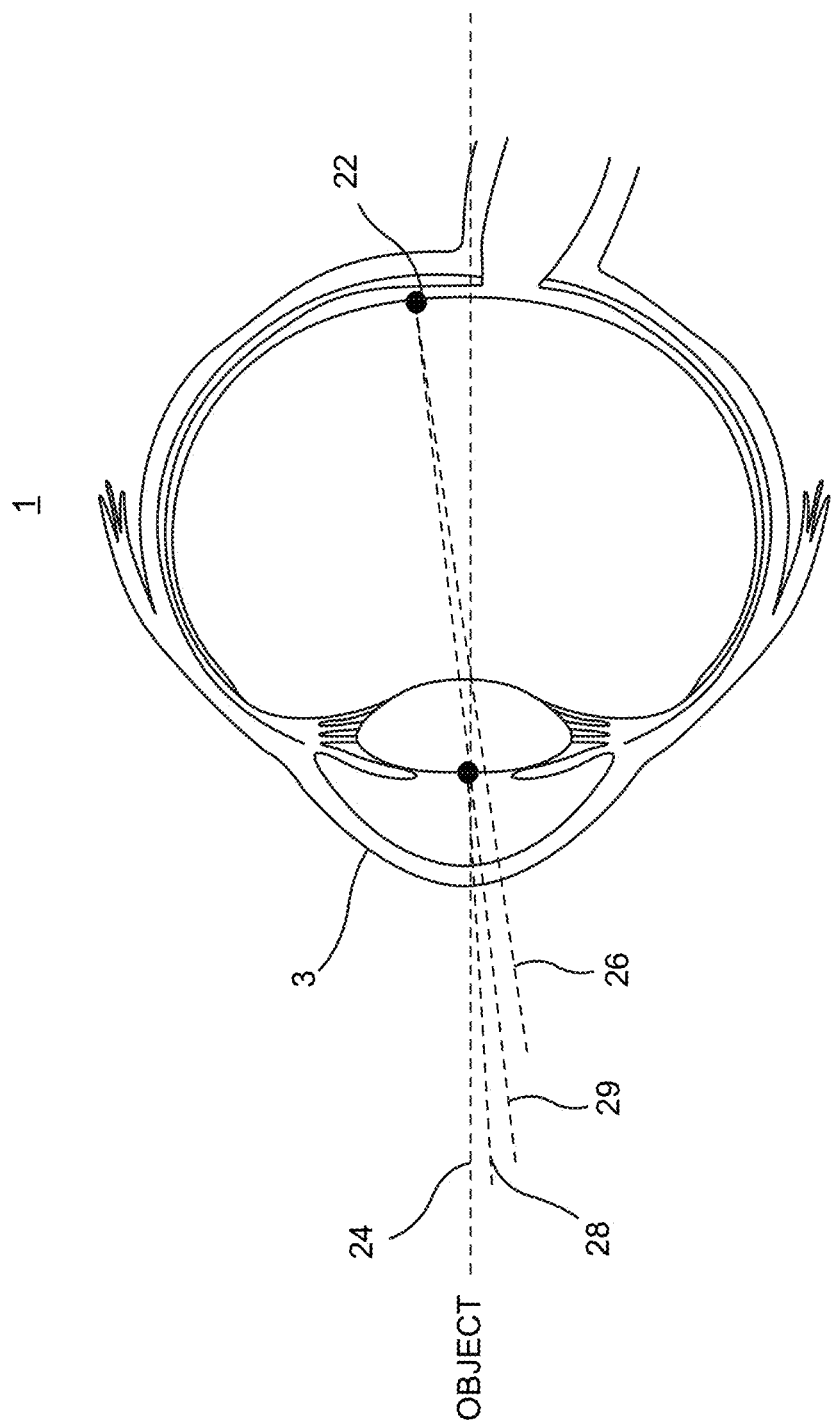
FIG. 5 is a sectional schematic illustration of a human eye showing various axes associated with the eye.

Disclosed herein are systems and methods for safely and effectively reducing intra-ocular pressure (IOP) in the eye to either treat or reduce the risk of glaucoma. The systems and methods enable access to the irido-corneal angle of the eye and use laser surgery techniques to treat abnormal ocular tissue conditions within the irido-corneal angle that may be causing elevated IOP.

The system and method disclosed herein also enables the locating or detection of a surface of ocular tissue while a focus of a laser is being moved about within the eye, either in the direction of propagation of the laser or opposite the direction of propagation. The detection is made based on the relative position of a pair of spots of light, either visually by a surgeon viewing the pair of spots in an image of the irido-corneal angle of the eye, or automatically by a processor analyzing the relative position of the pair of spots in an image of the irido-corneal angle. When the spots overlap the surface of ocular, the tissue is considered detected. The laser beam and the beams of light producing the spots are aligned such that the focus of the laser beam is at the intersection of the beams of light. Accordingly, the focus of the laser is considered to be on or at the surface of ocular tissue when the spots of light overlap.

In the systems and methods described in detail herein the laser producing a surgical effect is a femtosecond laser. Other types of surgical lasers, however, may be used. For example, photodisruptive lasers, also known as photoionizing lasers, such as neodymium-doped yttrium aluminum garnet (Nd:YAG) or neodymium-doped yttrium lithium fluoride (Nd:YLF) lasers can be used. These types of lasers are characterized by the generation of very short optical pulses with very large peak intensities that strip electrons from molecules of tissue in the focus of the beam.

Opto-Mechanical Imaging

In accordance with embodiments disclosed herein, opto-mechanical imaging is used by the system disclosed herein to locate a target surface of ocular tissue in an irido-corneal angle of an eye. To this end, the system includes a laser source configured to output a femtosecond laser beam, and a dual aiming beam apparatus configured to transmit a first aiming beam of light and a second aiming beam of light. The system further includes an optics subsystem optically aligned with the laser source and the dual aiming beam apparatus to receive the femtosecond laser beam, the first aiming beam of light, and the second aiming beam of light. The optics subsystem includes a focusing objective configured to direct the first aiming beam of light and the second aiming beam of light to be incident with the target surface and to align the first aiming beam of light and the second aiming beam of light relative to each other and relative to the femtosecond laser beam such that the first aiming beam of light and the second aiming beam of light intersect at a point corresponding to a focus of the femtosecond laser beam. An imaging apparatus optically aligned with the optics subsystem captures an image of the irido-corneal angle including a first spot corresponding to the first aiming beam of light and a second spot corresponding to a second aiming beam of light. The first spot of light and the second spot of light appear in the image as two separate visible spots on the target surface when the focus is away from the surface, and as a single, overlapping spot when the focus is on the surface.

In one configuration, the intersection point of the first aiming beam of light and the second aiming beam of light is at a location that is the same as the location of the focus of the laser beam. In this case, the intersection point of the beams and the focus of the laser beam are considered co-located and the correspondence between the intersection point and the focus of the laser beam is precise. In another configuration, the intersection point of the first aiming beam of light and the second aiming beam of light is at a location different from the location of the focus of the laser beam. In this case, the intersection point of the beams and the focus of the laser beam are considered non co-located and the correspondence between the intersection point and the focus of the laser beam is not exact, but within an acceptable measure of tolerance.

The pair of aiming beams of light can scan along the axis of propagation of the femtosecond laser beam a large distance inside the anterior chamber of the eye searching for the location where the two beams overlap. However, aiming beams incident on a surface is generally considered a relatively low resolution means of locating the surface. For example, a difficulty may lie in how well a surgeon can visualize the two spots of light in an image as the spots converge and fully overlap. The accuracy of determining the target surface has been located with intersecting beams depends on the angle at which the aiming beams are incident, the size of the aiming beams and the brightness of the aiming beams as well as the experience of the surgeon. The error in locating the target surface of ocular tissue has been estimated to be not better than ±1 mm from the actual surface location.

Opto-Mechanical Imaging Plus OCT Imaging

While the system just disclosed enables the detection of a target surface of ocular tissue in an irido-corneal angle of an eye, as noted above, there is room for improved accuracy. Thus, in accordance with embodiments disclosed herein, OCT imaging may be used in combination with opto-mechanical imaging, to provide spatial resolution and contrast to resolve microscopic details of ocular tissue and more accurate detection of tissue surfaces. When used, OCT imaging can provide two-dimensional (2D) cross-sectional images of the ocular tissue. These 2D cross-sectional images may be processed and analyzed to more accurately locate a target surface of tissue.

An OCT imaging apparatus can locate a target surface of tissue within a few microns of the actual location. However, the range over which the OCT imaging apparatus is effective is not more than 1 or 2 mm. So while an OCT imaging apparatus is a very high-resolution device, it cannot replace the opto-mechanical imaging aspect of the system because OCT is hampered by its relatively short effective range of operation. In other words, OCT imaging alone is not an effective means of locating the target surface of ocular tissue for femtosecond glaucoma surgery.

The disclosed system combines the dual aiming beam aspect of opto-mechanical imaging with OCT imaging to locate the target surface of tissue in femtosecond laser glaucoma treatments. To this end, the optics subsystem is optically aligned to receive the OCT beam and configured to direct the OCT beam to be incident with the target surface and to be aligned with the first aiming beam of light and the second aiming beam of light and relative to the femtosecond laser beam such that the OCT beam, the first aiming beam of light, and the second aiming beam of light intersect at a point corresponding to the focus of the femtosecond laser beam. The first aiming beam of light and the second aiming beam aiming beams are first used to provide a "coarse" detection of the target surface of tissue. Once the location of the target surface of tissue is approximately known, images resulting from the OCT beam are used to provide a "fine" detection of the location of the target surface of tissue. Once the location of the target surface of tissue is precisely known, the same OCT images are used to detect sub-surface tissues and distances of these sub-surfaces relative the target surface. These sub-surface tissues and distances can be electronically marked by a controller of the system and subsequently used to laser treatment to adjust the location of the focus of the femtosecond laser.

Femtosecond Laser Source

The preferred laser surgical component of the integrated surgical system disclosed herein is a femtosecond laser. A femtosecond laser provides highly localized, non-thermal photo-disruptive laser-tissue interaction with minimal collateral damage to surrounding ocular tissue. Photo-disruptive interaction of the laser is utilized in optically transparent tissue. The principal mechanism of laser energy deposition into the ocular tissue is not by absorption but by a highly nonlinear multiphoton process. This process is effective only at the focus of the pulsed laser where the peak intensity is high. Regions where the beam is traversed but not at the focus are not affected by the laser. Therefore, the interaction region with the ocular tissue is highly localized both transversally and axially along the laser beam. The process can also be used in weakly absorbing or weakly scattering tissue. While femtosecond lasers with photo-disruptive interactions have been successfully used in ophthalmic surgical systems and commercialized in other ophthalmic laser procedures, none have been used in an integrated surgical system that accesses the irido-corneal angle.

In known refractive procedures, femtosecond lasers are used to create corneal flaps, pockets, tunnels, arcuate incisions, lenticule shaped incisions, partial or fully penetrating corneal incisions for keratoplasty. For cataract procedures the laser creates a circular cut on the capsular bag of the eye for capsulotomy and incisions of various patterns in the lens for breaking up the interior of the crystalline lens to smaller fragments to facilitate extraction. Entry incisions through the cornea opens the eye for access with manual surgical devices and for insertions of phacoemulsification devices and intra-ocular lens insertion devices.

These existing systems are developed for their specific applications, for surgery in the cornea, and the crystalline lens and its capsular bag and are not capable of performing surgery in the irido-corneal angle 13 for several reasons. First, the irido-corneal angle 13 is not accessible with these surgical laser systems because the irido-corneal angle is too far out in the periphery and is outside of surgical range of these systems. Second, the angle of the laser beam from these systems, which is along the optical axis 24 to the eye 1, is not appropriate to reaching the irido-corneal angle 13, where there is significant scattering and optical distortion at the applied wavelength. Third, any imaging capabilities these systems may have do not have the accessibility, penetration depth and resolution to image the tissue along the trabecular outflow pathway 40 with sufficient detail and contrast.

In the integrated surgical system disclosed herein, clear access to the irido-corneal angle 13 is provided along the angled beam path 30. The tissue, e.g., cornea 3 and the aqueous humor 8 in the anterior chamber 7, along this angled beam path 30 is transparent for wavelengths from approximately 400 nm to 2500 nm and femtosecond lasers operating in this region can be used. Such mode locked lasers work at their fundamental wavelength with Titanium, Neodymium or Ytterbium active material. Non-linear frequency conversion techniques known in the art, frequency doubling, tripling, sum and difference frequency mixing techniques, optical parametric conversion can convert the fundamental wavelength of these lasers to practically any wavelength in the above mentioned transparent wavelength range of the cornea.

Existing ophthalmic surgical systems apply lasers with pulse durations longer than 1 ns have higher photo-disruption threshold energy, require higher pulse energy and the dimension of the photo-disruptive interaction region is larger, resulting in loss of precision of the surgical treatment. When treating the irido-corneal angle 13, however, higher surgical precision is required. To this end, the integrated surgical system may be configured to apply lasers with pulse durations from 10 femtosecond (fs) to 1 nanosecond (ns) for generating photo-disruptive interaction of the laser beam with ocular tissue in the irido-corneal angle 13. While lasers with pulse durations shorter than 10 fs are available, such laser sources are more complex and more expensive. Lasers with the described desirable characteristics, e.g., pulse durations from 10 femtosecond (fs) to 1 nanosecond (ns), are commercially available.

Accessing the Irido-Corneal Angle

Figure 6:
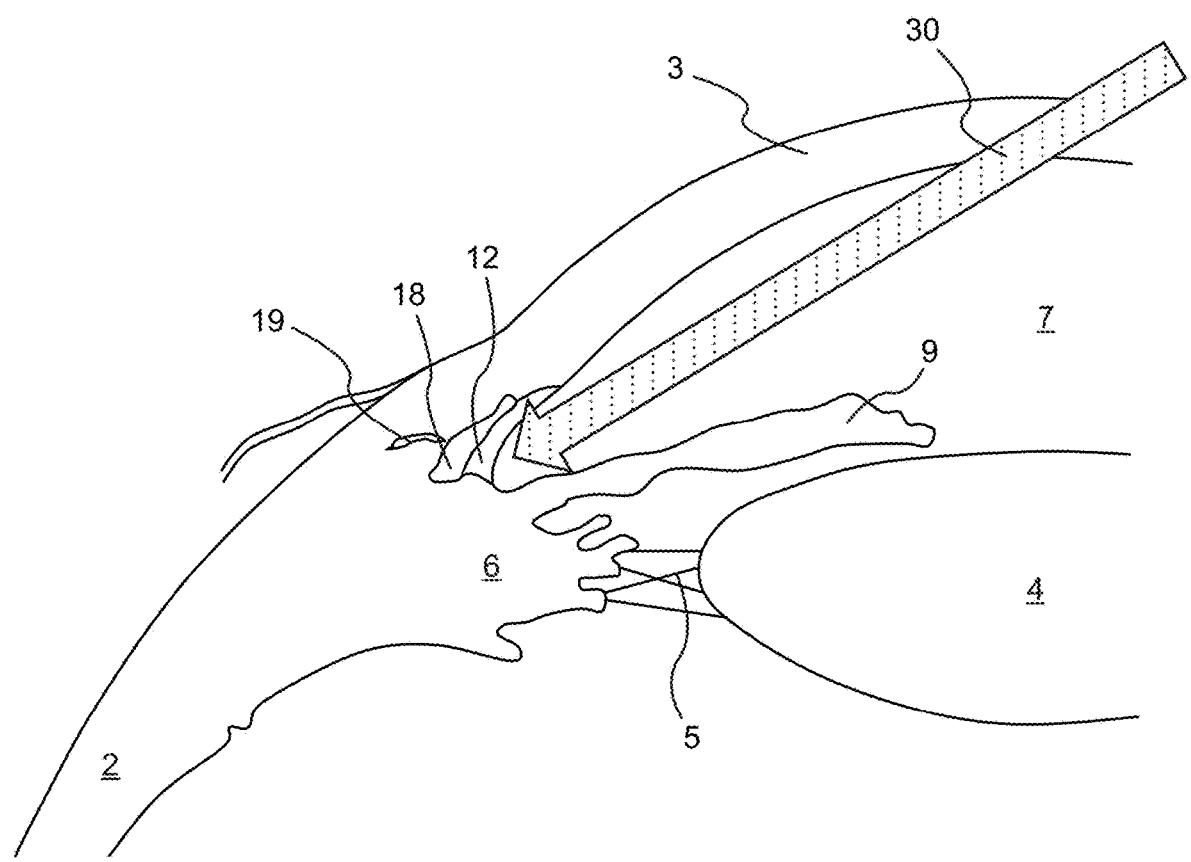
FIG. 6 is a sectional schematic illustration of an angled beam path along which one or more light beams may access the irido-corneal angle of the eye.

A feature afforded by the integrated surgical system is access to the targeted ocular tissue in the irido-corneal angle 13. With reference to FIG. 6, the irido-corneal angle 13 of the eye may be accessed via the integrated surgical system along an angled beam path 30 passing through the cornea 3 and through the aqueous humor 8 in the anterior chamber 7. For example, one or more of an imaging beam, e.g., an OCT beam and/or a illumination observation beam, and a laser beam may access the irido-corneal angle 13 of the eye along the angled beam path 30.

An optical system disclosed herein is configured to direct a light beam to an irido-corneal angle 13 of an eye along an angled beam path 30. The optical system includes a first optical subsystem and a second optical subsystem. The first optical subsystem includes a window formed of a material with a refractive index $n_w$ and has opposed concave and convex surfaces. The first optical subsystem also includes an exit lens formed of a material having a refractive index $n_x$. The exit lens also has opposed concave and convex surfaces. The concave surface of the exit lens is configured to couple to the convex surface of the window to define a first optical axis extending through the window and the exit lens. The concave surface of the window is configured to detachably couple to a cornea of the eye with a refractive index $n_c$ such that, when coupled to the eye, the first optical axis is generally aligned with the direction of view of the eye.

The second optical subsystem is configured to output a light beam, e.g., an OCT beam or a laser beam. The optical system is configured so that the light beam is directed to be incident at the convex surface of the exit lens along a second optical axis at an angle α that is offset from the first optical axis. The respective geometries and respective refractive indices $n_x$, and $n_w$ of the exit lens and window are configured to compensate for refraction and distortion of the light beam by bending the light beam so that it is directed through the cornea 3 of the eye toward the irido-corneal angle 13. More specifically, the first optical system bends the light beam such that the light beam exits the first optical subsystem and enters the cornea 3 at an appropriate angle so that the light beam progresses through the cornea and the aqueous humor 8 in a direction along the angled beam path 30 toward the irido-corneal angle 13.

Accessing the irido-corneal angle 13 along the angled beam path 30 provides several advantages. An advantage of this angled beam path 30 to the irido-corneal angle 13 is that the OCT beam and laser beam passes through mostly clear tissue, e.g., the cornea 3 and the aqueous humor 8 in the anterior chamber 7. Thus, scattering of these beams by tissue is not significant. With respect to OCT imaging, this enables the use of shorter wavelength, less than approximately 1 micrometer, for the OCT to achieve higher spatial resolution. An additional advantage of the angled beam path 30 to the irido-corneal angle 13 through the cornea 3 and the anterior chamber 7 is the avoidance of direct laser beam or OCT beam light illuminating the retina 11. As a result, higher average power laser light and OCT light can be used for imaging and surgery, resulting in faster procedures and less tissue movement during the procedure.

Another important feature provided by the integrated surgical system is access to the targeted ocular tissue in the irido-corneal angle 13 in a way that reduces beam discontinuity. To this end, the window and exit lens components of the first optical subsystem are configured to reduce the discontinuity of the optical refractive index between the cornea 3 and the neighboring material and facilitate entering light through the cornea at a steep angle.

Having thus generally described the integrated surgical system and some of its features and advantages, a more detailed description of the system and its component parts follows.

Integrated Surgical System

Figure 7:
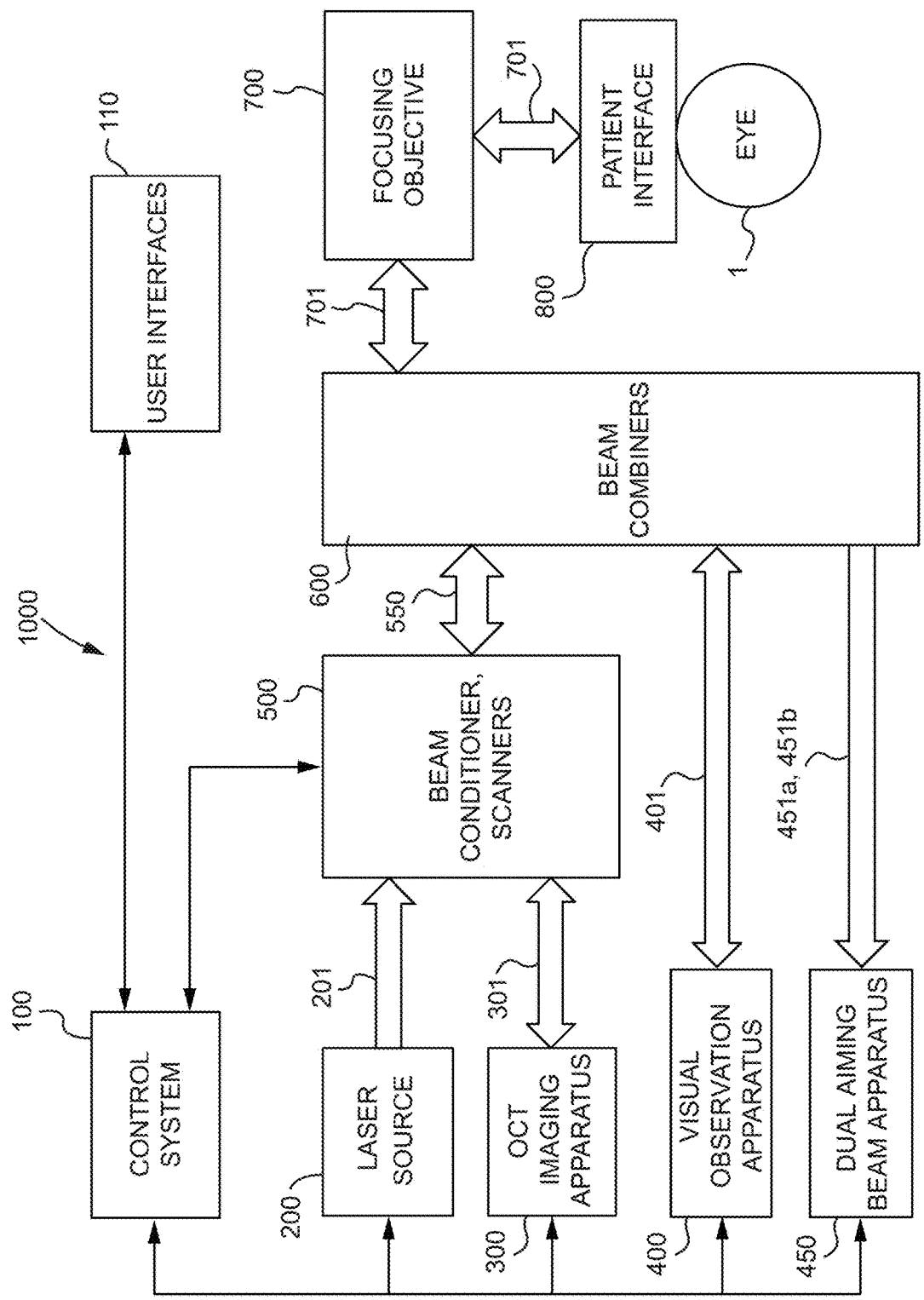
FIG. 7 is a block diagram of an integrated surgical system for non-invasive glaucoma surgery including a control system, a laser source, an OCT imaging apparatus, a visual observation apparatus, a dual aiming beam apparatus, beam conditioners and scanners, beam combiners, a focusing objective, and a patient interface.

With reference to FIG. 7, an integrated surgical system 1000 for non-invasive glaucoma surgery may include a control system 100, a surgical component 200, a first imaging apparatus 300, a second imaging apparatus 400, and a dual aiming beam apparatus 450. In the embodiment of FIG. 7, the surgical component 200 is a femtosecond laser source, the first imaging apparatus 300 is an OCT imaging apparatus, and the second imaging apparatus 400 is a visual observation apparatus comprising a video camera and an illumination source for viewing or capturing images of a surgical field. The dual aiming beam apparatus 450 outputs a pair of beams of light, referred to herein as aiming beams, for use in detecting a surface of ocular tissue in the surgical field. Other components of the integrated surgical system 1000 include beam conditioners and scanners 500, beam combiners 600, a focusing objective 700, and a patient interface 800.

The control system 100 may be a single computer or and plurality of interconnected computers configured to control the hardware and software components of the other components of the integrated surgical system 1000. A user interface 110 of the control system 100 accepts instructions from a user and displays information for observation by the user. Input information and commands from the user include but are not limited to system commands, motion controls for docking the patient's eye to the system, selection of pre-programmed or live generated surgical plans, navigating through menu choices, setting of surgical parameters, responses to system messages, determining and acceptance of surgical plans and commands to execute the surgical plan. Outputs from the system towards the user includes but are not limited to display of system parameters and messages, display of images of the eye, graphical, numerical and textual display of the surgical plan and the progress of the surgery.

The control system 100 is connected to the other components 200, 300, 400, 450, 500 of the integrated surgical system 1000. Signals between the control system 100 and the femtosecond laser source 200 function to control internal and external operation parameters of the laser source, including for example, power, repetition rate and beam shutter. Control and feedback signals between the control system 100 and the OCT imaging apparatus 300 function to control OCT beam scanning parameters, and the acquiring, analyzing and displaying of OCT images. Control signals between the control system 100 and the dual aiming beam apparatus 450 function to control the output of beams of light by the one or more aiming beam sources of the dual aiming beam apparatus. Control signals between the control system 100 and the visual observation apparatus 400 function to control the capturing, image processing and displaying of spots of light on tissue surfaces in the surgical field that result from the one or more beams of light output by the dual aiming beam apparatus 450. To this end, the line of sight of the visual observation apparatus 400 is aligned with the femtosecond laser and directed into the irido-corneal angle of the eye. Control signals from the control system 100 to the beam conditioner and scanners 500 function to control the focus of the laser beam output by the femtosecond laser source 200. Such control may include advancing the focus of the laser beam in the direction of propagation of the laser or in the direction opposite the direction of propagation of the laser, and scanning the focus.

Laser beams 201 from the femtosecond laser source 200 and OCT beams 301 from the OCT imaging apparatus 300 are directed towards a unit of beam conditioners and scanners 500. Different kinds of scanners can be used for the purpose of scanning the laser beam 201 and the OCT beam 301. For scanning transversal to a beam 201, 301, angular scanning galvanometer scanners are available for example from Cambridge Technology, Bedford, MA, and Scanlab, Munich, Germany. To optimize scanning speed, the scanner mirrors are typically sized to the smallest size, which still support the required scanning angles and numerical apertures of the beams at the target locations. The ideal beam size at the scanners is typically different from the beam size of the laser beam 201 or the OCT beam 301, and different from what is needed at the entrance of a focusing objective 700. Therefore, beam conditioners are applied before, after or in between individual scanners. The beam conditioner and scanners 500 includes scanners for scanning the beam transversally and axially. Axial scanning changes the depth of the focus at the target region. Axial scanning can be performed by moving a lens axially in the beam path with a servo or stepper motor.

The laser beam 201 and the OCT beam 301 are combined by dichroic, polarization or other kind of beam combiners 600 to reach a common target volume or surgical volume in the eye. Likewise, an illumination beam 401 from the visual observation apparatus 400 and a pair of aiming beams of light 451a, 451b from the dual aiming beam apparatus 450 are combined by dichroic, polarization or other kind of beam combiners 600 to reach the common target volume or surgical volume in the eye. In an integrated surgical system 1000 having a femtosecond laser source 200, an OCT imaging apparatus 300, a visual observation apparatus 400, and an dual aiming beam apparatus 450, the individual beams 201, 301, 401, 451a, 451b for each of these components may be individually optimized and may be collinear or non-collinear to one another. The beam combiner 600 uses dichroic or polarization beam splitters to split and recombine light with different wavelength and/or polarization. The beam combiner 600 may also include optics, such as a telescope, to change certain parameters of the individual beams 201, 301, 401, 451a, 451b such as beam size, beam angle and divergence. Integrated visual illumination, observation or imaging devices assist the surgeon in docking the eye to the system and identifying surgical locations.

To resolve ocular tissue structures of the eye in sufficient detail, the OCT imaging apparatus 300 of the integrated surgical system 1000 may provide an OCT having a spatial resolution of several micrometers. The resolution of the OCT beam is the spatial dimension of the smallest feature that can be recognized in the OCT image. It is determined mostly by the wavelength and the spectral bandwidth of the OCT source, the quality of the optics delivering the OCT beam to the target location in the eye, the numerical aperture of the OCT beam and the spatial resolution of the OCT imaging apparatus 300 at the target location. In one embodiment, the OCT beam of the integrated surgical system has a resolution of no more than 5 µm.

Likewise, the surgical laser beam provided by the femtosecond laser source 200 may be delivered to targeted locations with several micrometer accuracy. The resolution of the laser beam is the spatial dimension of the smallest feature at the target location that can be modified by the laser beam without significantly affecting surrounding ocular tissue. It is determined mostly by the wavelength of the laser beam, the quality of the optics delivering the laser beam to target location in the eye, the numerical aperture of the laser beam, the energy of the laser pulses in the laser beam and the spatial resolution of the laser scanning system at the target location. In addition, to minimize the threshold energy of the laser for photo-disruptive interaction, the size of the laser spot should be no more than approximately 5 µm.

For practical embodiments, beam conditioning, scanning and the combining of optical paths are performed on the laser beam 201, the OCT beam 301, the illumination beam 401, and the aiming beams of light 451a, 451b. Implementation of those functions may happen in a different order than what is indicated in FIG. 7. Specific optical hardware that manipulates the beams to implement those functions can have multiple arrangements with regards to how the optical hardware is arranged. They can be arranged in a way that manipulates individual optical beams separately, in another embodiment one component may combine functions and manipulates different beams. For example, a single set of scanners can scan both the laser beam 201 and the OCT beam 301. In this case, separate beam conditioners set the beam parameters for the laser beam 201 and the OCT beam 301, then a beam combiner combines the two beams for a single set of scanners to scan the beams. While many combinations of optical hardware arrangements are possible for the integrated surgical system, the following section describes an example arrangement.

In the following description, the term beam may—depending on the context—refer to one of a laser beam, an OCT beam, an illumination beam, or one or more aiming beams. A combined beam refers to two or more of a laser beam, an OCT beam, an illumination beam, or an aiming beam that are either collinearly combined or non-collinearly combined. Example combined beams include a combined OCT/laser beam, which is a collinear or non-colinear combination of an OCT beam and a laser beam, a combined OCT/laser/illumination beam, which is a collinear or non-collinear combination of an OCT beam, a laser beam, and an illumination beam, and a combined OCT/laser/illumination/aiming beam, which is a collinear or non-collinear combination of an OCT beam, a laser beam, an illumination beam, and one or more aiming beams. In a collinearly combined beam, the different beams may be combined by dichroic or polarization beam splitters, and delivered along a same optical path through a multiplexed delivery of the different beams. In a non-collinear combined beam, the different beams are delivered at the same time along different optical paths that are separated spatially or by an angle between them.

In the description to follow, any of the foregoing beams or combined beams may be generically referred to as a light beam. The terms distal and proximal may be used to designate the direction of travel of a beam, or the physical location of components relative to each other within the integrated surgical system. The distal direction refers to a direction toward the eye; thus an OCT beam output by the OCT imaging apparatus moves in the distal direction toward the eye. The proximal direction refers to a direction away from the eye; thus an OCT return beam from the eye moves in the proximal direction toward the OCT imaging apparatus.

Figure 8A:
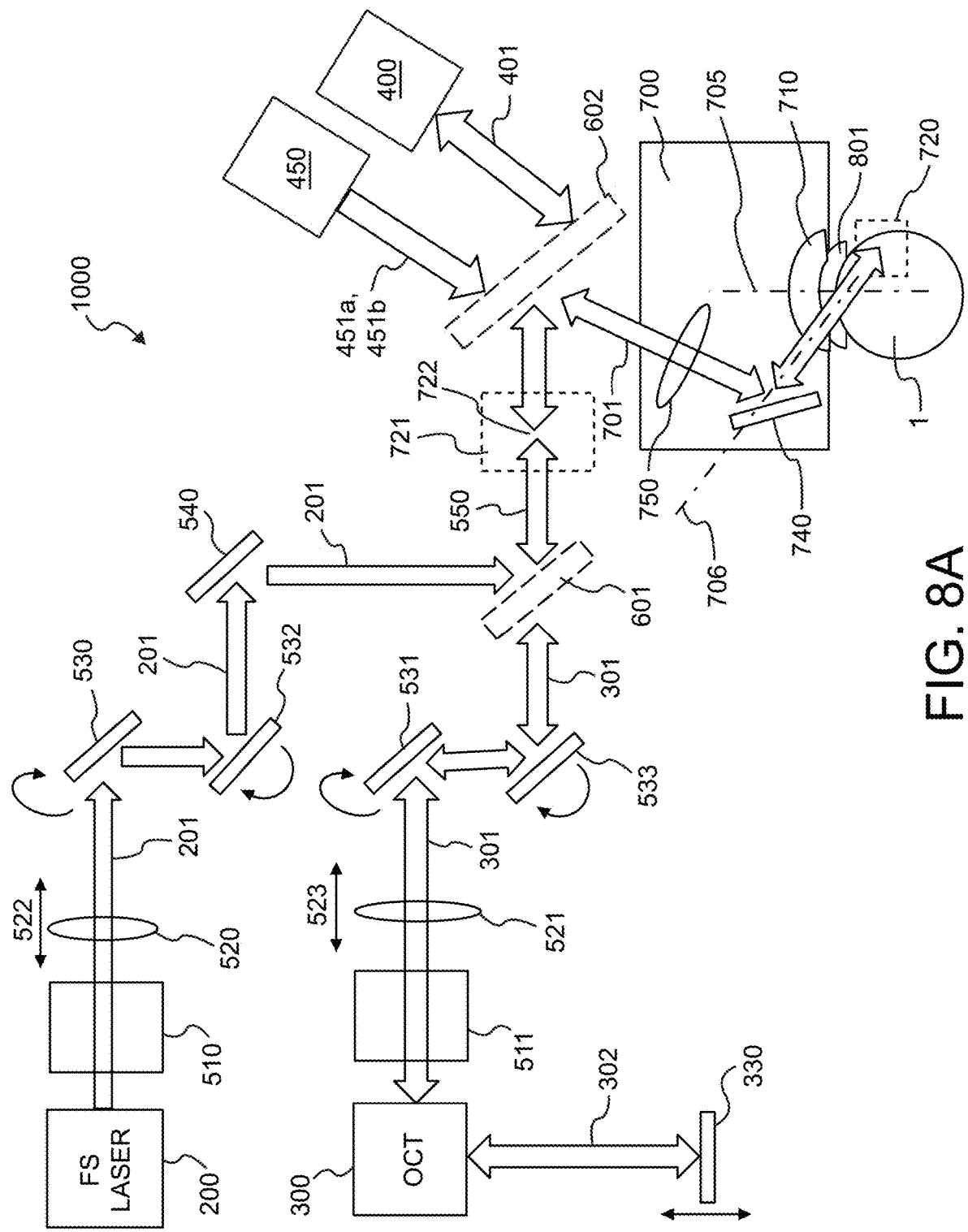
FIG. 8A is a detailed block diagram of the integrated surgical system of FIG. 7.

Referring to FIG. 8A, in one embodiment, an integrated surgical system is configured to deliver each of a laser beam 201, an illumination beam 401, and a pair of aiming beams of light 451a, 451b in the distal direction toward an eye 1, and an illumination return beam 401 back from the eye 1. In another embodiment, an integrated surgical system is configured to deliver each of a laser beam 201, an OCT beam 301, an illumination beam 401, and a pair of aiming beams of light 451a, 451b in the distal direction toward an eye 1, and receive each of an OCT return beam 301 and an illumination return beam 401 back from the eye 1. Regarding the delivery of a laser beam, a laser beam 201 output by the femtosecond laser source 200 passes through a beam conditioner 510 where the basic beam parameters, beam size, divergence are set. The beam conditioner 510 may also include additional functions, setting the beam power or pulse energy and shutter the beam to turn it on or off. After existing the beam conditioner 510, the laser beam 210 enters an axial scanning lens 520. The axial scanning lens 520, which may include a single lens or a group of lenses, is movable in the axial direction 522 by a servo motor, stepper motor or other control mechanism. Movement of the axial scanning lens 520 in the axial direction 522 changes the axial distance of the focus of the laser beam 210 at a focal point.

In a particular embodiment of the integrated surgical system, an intermediate focal point 722 is set to fall within, and is scannable in, the conjugate surgical volume 721, which is an image conjugate of the surgical volume 720, determined by the focusing objective 700. The surgical volume 720 is the spatial extent of the region of interest within the eye where imaging and surgery is performed. For glaucoma surgery, the surgical volume 720 is the vicinity of the irido-corneal angle 13 of the eye.

A pair of transverse scanning mirrors 530, 532 rotated by a galvanometer scanner scan the laser beam 201 in two essentially orthogonal transversal directions, e.g., in the x and y directions. Then the laser beam 201 is directed towards a dichroic or polarization beam splitter 540 where it is reflected toward a beam combining mirror 601 configured to combine the laser beam 201 with an OCT beam 301.

Regarding delivery of an OCT beam, an OCT beam 301 output by the OCT imaging apparatus 300 passes through a beam conditioner 511, an axially moveable focusing lens 521 and a transversal scanner with scanning mirrors 531 and 533. The focusing lens 521 is used to set the focal position of the OCT beam in the conjugate surgical volume 721 and the real surgical volume 720. The focusing lens 521 is not scanned for obtaining an OCT axial scan. Axial spatial information of the OCT image is obtained by Fourier transforming the spectrum of the interferometrically recombined OCT return beam 301 and reference beams 302. However, the focusing lens 521 can be used to re-adjust the focus when the surgical volume 720 is divided into several axial segments. This way the optimal imaging spatial resolution of the OCT image can be extended beyond the Rayleigh range of the OCT signal beam, at the expense of time spent on scanning at multiple ranges.

Proceeding in the distal direction toward the eye 1, after the scanning mirrors 531 and 533, the OCT beam 301 is combined with the laser beam 201 by the beam combiner minor 601. The OCT beam 301 and laser beam 201 components of the combined laser/OCT beam 550 are multiplexed and travel in the same direction to be focused at an intermediate focal point 722 within the conjugate surgical volume 721. After having been focused in the conjugate surgical volume 721, the combined laser/OCT beam 550 propagates to a second beam combining minor 602 where it is combined with one or more aiming beams of light 451 and an illumination beam 401 to form a combined laser/OCT/illumination/aiming beam 701. Regarding delivery of the illumination beam 401 and the pair of aiming beams of light 451a, 451b, details of the delivery of these beams is described below with reference to FIGS. 8B, 8C and 8D.

The combined laser/OCT/illumination/aiming beam 701 traveling in the distal direction then passes through an objective lens 750 included in the focusing objective 700, is reflected by a beam-folding mirror 740 and then passes through an exit lens 710 and a window 801 of a patient interface, where the intermediate focal point 722 of the laser beam within the conjugate surgical volume 721 is re-imaged into a focal point in the surgical volume 720. The focusing objective 700 re-images the intermediate focal point 722, through the window 801 of a patient interface, into the ocular tissue within the surgical volume 720.

A scattered OCT return beam 301 from the ocular tissue travels in the proximal direction to return to the OCT imaging apparatus 300 along the same paths just described, in reverse order. The reference beam 302 of the OCT imaging apparatus 300, passes through a reference delay optical path and return to the OCT imaging apparatus from a moveable minor 330. The reference beam 302 is combined interferometrically with the OCT return beam 301 on its return within the OCT imaging apparatus 300. The amount of delay in the reference delay optical path is adjustable by moving the moveable minor 330 to equalize the optical paths of the OCT return beam 301 and the reference beam 302. For best axial OCT resolution, the OCT return beam 301 and the reference beam 302 are also dispersion compensated to equalize the group velocity dispersion within the two arms of the OCT interferometer.

When the combined laser/OCT/illumination/aiming beam 701 is delivered through the cornea 3 and the anterior chamber 7, the combined beam passes through posterior and anterior surface of the cornea at a steep angle, far from normal incidence. These surfaces in the path of the combined laser/OCT/illumination/aiming beam 701 create excessive astigmatism and coma aberrations that need to be compensated for.

Having thus disclosed the general configuration and operation of the integrated surgical system 1000, the dual aiming beam feature of the system is further described with reference to a first embodiment shown in FIG. 8B and a second embodiment shown in FIG. 8C.

Figure 8B:
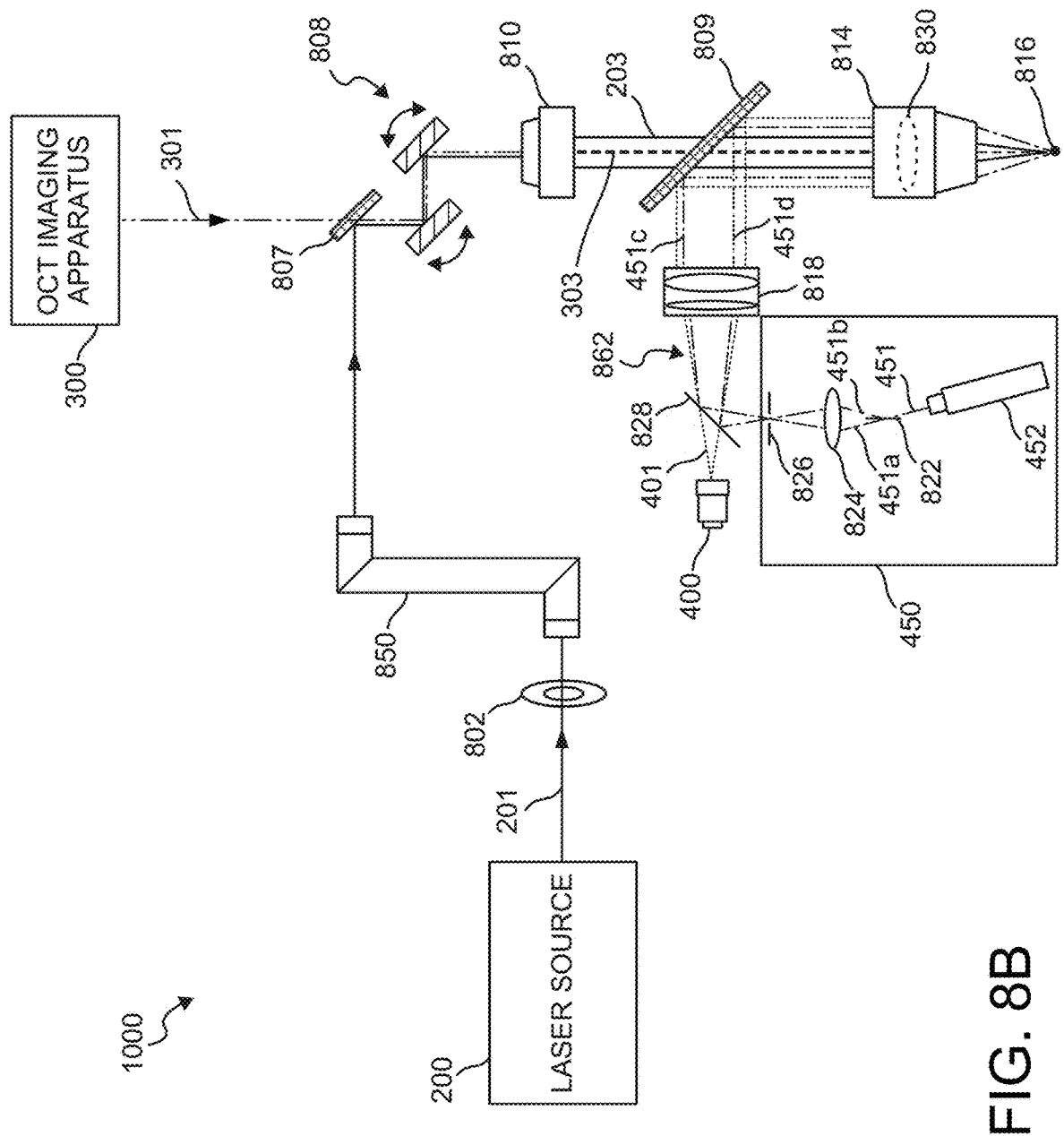
FIG. 8B is a block diagram of an integrated surgical system of FIG. 7 having a first embodiment of a dual aiming beam apparatus.

In the first embodiment shown in FIG. 8B, a laser source 200 emits a laser beam 201 of femtosecond light pulses through a control shutter 802 and into an articulated arm 850. The articulated arm 850 transmits the laser beam 201 onto a first dichroic mirror 807 that reflects the laser wavelength. The laser beam 201 is directed into a pair of scanning mirrors 808 and into an expanding telescope 810. The expanding telescope 810 increases the diameter of the femtosecond laser beam 201 and pre-compensates for astigmatism that will be introduced by the human cornea. The expanded laser beam 203 is then incident onto a second dichroic mirror 809. The second dichroic mirror 809 is configured to transmit the laser wavelength, e.g., 1030 nm in the case of a femtosecond laser, and to not reflect the laser wavelength. The expanded laser beam 203 is then incident into an objective lens 830 included in a focusing objective 814. At this stage the expanded laser beam 203 is parallel to the axis of the objective lens 830 and the lens focuses the laser beam to a point 816 at a predetermined distance from the exit surface of the objective lens. Not shown in FIG. 8B are the optics and the patient interface components that reflect the laser beam into the irideocorneal angle. With reference to FIGS. 7 and 8A, these components may include, for example, a patient interface 800 and a beam-folding mirror 740 and an exit lens 710.

Regarding the diameter of the expanded laser beam 203, the diameter of the beam when it enters the objective lens 830 in the focusing objective 814 determines the final numerical aperture of the laser beam. The larger the diameter of the expanded laser beam 203, the greater the numerical aperture. In general, laser beams with greater numerical apertures are focused onto smaller points 816. The beam diameter and the numerical aperture are design choices that depend on the intended use of the device. In the present integrated surgical system 1000, the diameter of the expanded laser beam 203 is about 6 mm.

Continuing with FIG. 8B, an OCT imaging apparatus 300 transmits an OCT (near infrared) beam 301 onto the first dichroic mirror 807, which transmits the OCT beam. The OCT beam 301 and laser beam 201 are arranged such that both the OCT beam and laser beam are co-aligned and parallel upon emerging from the first dichroic mirror 807. The OCT beam 301 is directed into the pair of scanning mirrors 808 into the expanding telescope 810. The expanding telescope 810 increases the diameter of the OCT beam 301 and it also pre-compensates for astigmatism that will be introduced by the human cornea. The expanded OCT beam 303 is then incident onto the second dichroic mirror 809. The second dichroic mirror 809 is configured to transmit the OCT wavelength, e.g., 850 nm, and to not reflect the OCT wavelength. The second dichroic mirror 809 is further configured to transmit near-infrared and infrared light. The second dichroic mirror 809 is also configured to reflect visible light. The expanded OCT beam 303 is then incident into the objective lens 830 included in the focusing objective 814. At this stage the expanded OCT beam 303 is parallel to the axis of the objective lens 830 and the lens focuses the OCT beam to the same spot 816 as the expanded laser beam 203.

A visual observation apparatus 400 enables visualization of the surgical field. In one configuration, the visual observation apparatus 400 includes an illumination source and a video camera. The illumination source component of the visual observation apparatus 400 shines an illumination beam 401 through a telescope 818 and onto the second dichroic mirror 809. The illumination beam 401 reflects from the second dichroic mirror 809 into the objective lens 830. The objective lens 830 focuses visible light from the illumination beam 401 to illuminate an area within the surgical field. The surgical field consists of the area on the trabecular meshwork that surrounds and is centered over the focus point 816 of the femtosecond laser beam 203 and the OCT beam 303. The illumination beam 401 reflects from the surgical field, returning back through the focusing objective 814 and onto the second dichroic mirror 809. The returning illumination beam 401 of light is focused by the telescope 818 onto the video camera component of the visual observation apparatus 400 where it forms an image of the surgical field.

Continuing with FIG. 8B, a dual aiming beam apparatus 450 comprising an aiming beam source 452, a first beam splitter 822, a focusing lens 824, an aperture 826, and a second beam splitter 828. The aperture 826 is placed at the conjugate plane of the telescope 818, that is, at a location where the telescope forms a second image plane by virtue of the second beam splitter 828. The aiming beam of light 451 shines onto the first beam splitter 822 to form two separate aiming beams of light 451a, 451b. The dual aiming beams of light 451a, 451b are focused by the focusing lens 824 through the aperture 826 onto the second beam splitter 828. Thus, the dual aiming beams 451a, 451b output by the dual aiming beam apparatus 450 enter an optical path 862 of the system 1000 between the visual observation apparatus 400 and the focusing objective 814 at a point before the second dichroic mirror 809. The second beam splitter 828 reflects the dual aiming beams of light 451a, 451b and transmits a fraction of the illumination beam 401 into the telescope 818.

Since the aiming beams of light 451a, 451b are emitted through an aperture 826 at the conjugate plane of the telescope 818, the resulting aiming beams of light 451c, 451d output through the telescope 818 are parallel to the illumination beam 401. The parallel dual aiming beams of light 451c, 451d are then reflected by the second dichroic mirror 809 onto the objective lens 830 included in the focusing objective 814. At this stage the dual aiming beams of light 451c, 451d are parallel to the axis of the objective lens 830 and the lens focuses the beams to the same spot 816 as the expanded laser beam 203 and the expanded OCT beam 303. Thus, through this configuration and arrangement of components, the parallel bundle of optical beams including the aiming beams of light 451c, 451d, the expanded OCT beam 303, and the expanded laser beam 203 are focused onto a single point 816 in a surgical area.

Light from the surgical area near the point 816 resulting from the illumination beam 401 re-enters the focusing objective 814 and is reflected by the second dichroic mirror 809 into the telescope 818. The telescope 818 focuses the illumination light onto the visual observation apparatus 400 where an image is formed. Additionally, the dual aiming beams of light 451c, 451d from the surgical area at the point 816 re-enter the focusing objective 814. A fraction of light from the dual aiming beams of light 451c, 451d is reflected by the second dichroic mirror 809 into the telescope 818. The telescope 818 focuses the dual aiming beams of light 451c, 451d onto the visual observation apparatus 400 where an image of the aiming beams is formed.

Figure 8C:
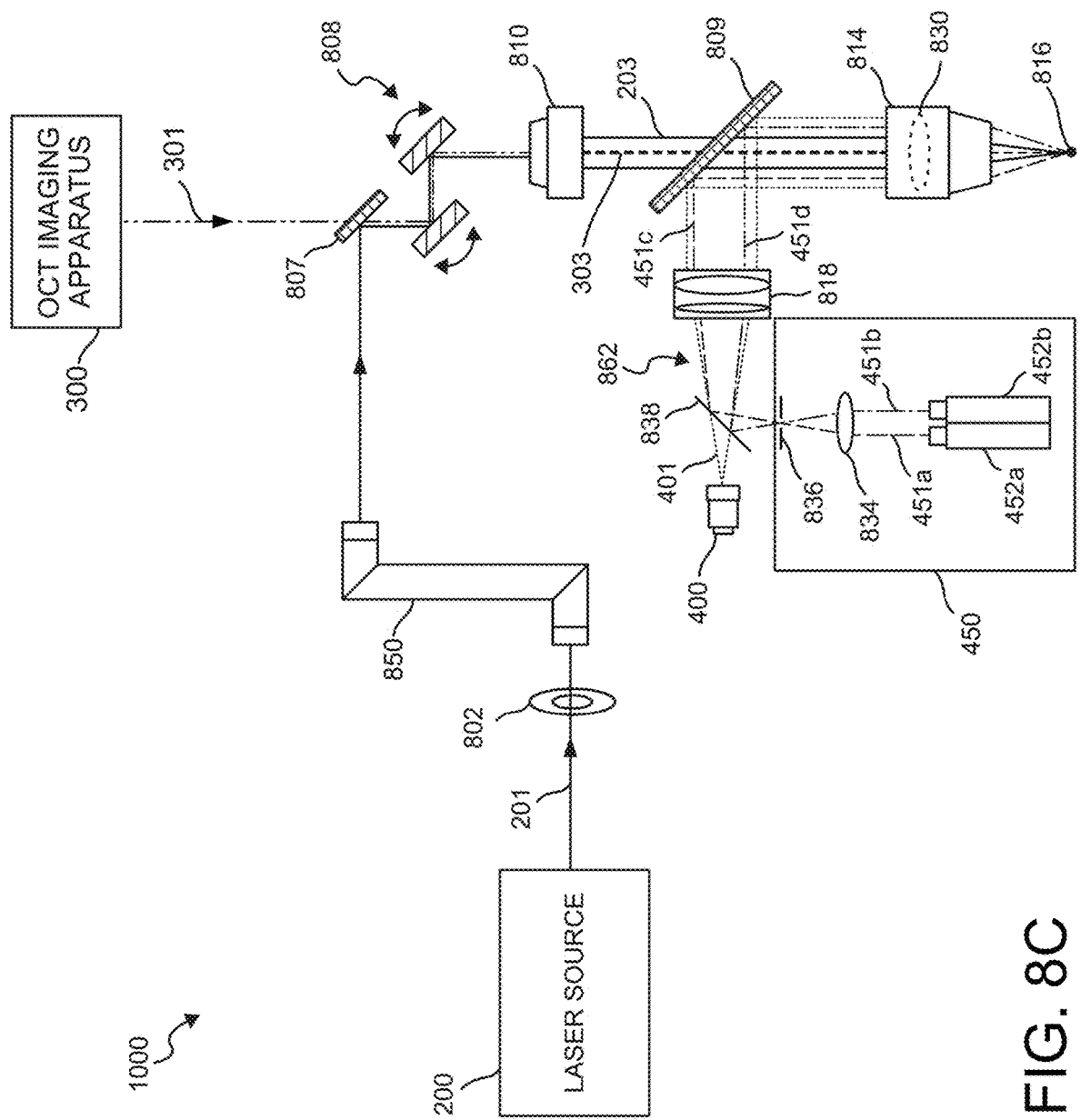
FIG. 8C is a block diagram of an integrated surgical system of FIG. 7 having a second embodiment of a dual aiming beam apparatus.

In the second embodiment shown in FIG. 8C, the arrangement and operation of the laser source 200, the OCT imaging apparatus 300 and various other components is identical the first embodiment with the exception of the dual aiming beam apparatus 450. In the second embodiment, the dual aiming beam apparatus 450 comprises a first aiming beam source 452a configured to output a first aiming beam of light 451a of a first color, a second aiming beam source 452b configured to output a second aiming beam of light 451b of a second color different than the first color, a focusing lens 834, an aperture 836, and a beam splitter 838. As in the first embodiment, the aperture 836 is placed at the conjugate plane of the telescope 818, that is, at a location where the telescope forms a second image plane by virtue of the second beam splitter 838. The aiming beams of light 451a, 451b shine light onto the focusing lens 834 that focuses the beams through the aperture 836 onto the beam splitter 838. Since the aiming beams of light 451a, 451b are emitted through an aperture 836 at the conjugate plane of the telescope 818, the resulting aiming beams of light 451c, 451d output through the telescope 818 are parallel to the illumination beam 401. The parallel dual aiming beams of light 451c, 451d are then reflected by the second dichroic mirror 809 onto the objective lens 830 included in the focusing objective 814. At this stage the dual aiming beams of light 451c, 451d are parallel to the axis of the objective lens 830 and the lens focuses the beams to the same spot 816 as the expanded laser beam 203 and the expanded OCT beam 303. Thus, through this configuration and arrangement of components, the parallel bundle of optical beams including the aiming beams of light 451c, 451d, the expanded OCT beam 303, and the expanded laser beam 203 are focused onto a single point 816.

Figure 8D:
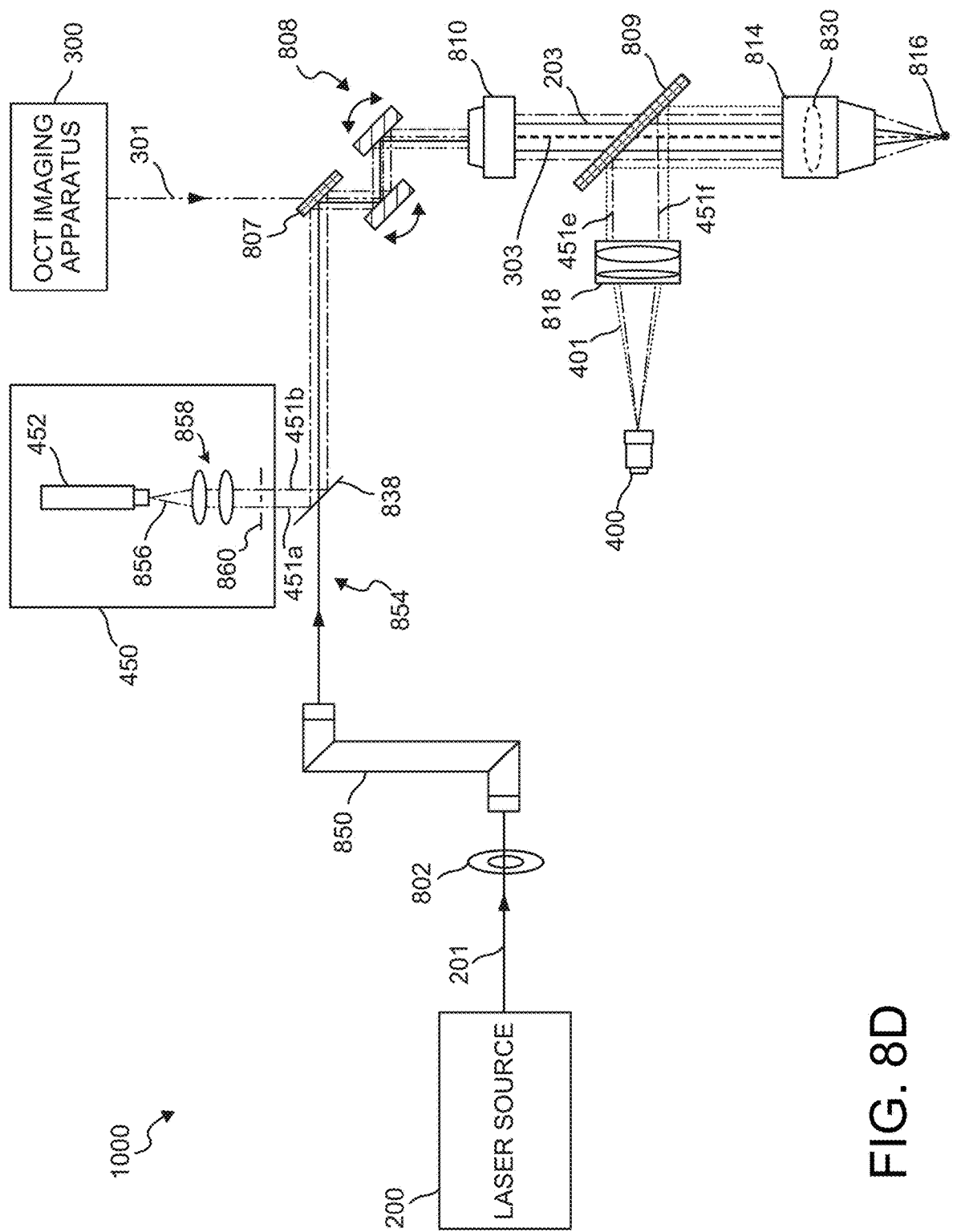
FIG. 8D is a block diagram of an integrated surgical system of FIG. 7 having a third embodiment of a dual aiming beam apparatus.

In the third embodiment shown in FIG. 8D, the arrangement and operation of the laser source 200, the OCT imaging apparatus 300 and various other components is similar to the first embodiment and the second embodiment with the exception of the placement of the dual aiming beam apparatus 450 and the beam splitter 838. In the third embodiment, the dual aiming beams 451a, 451b output by the dual aiming beam apparatus 450 enter an optical path 854 of the system 1000 between the laser source 200 and the focusing objective 814 at a point before the scanning mirror 808. Entry of the dual aiming beams of light 451a, 451b at this point enables the beams to be steered to locations of interest within the surgical area by the scanning mirror 808. This added flexibility allows more active targeting of the ocular tissue of interest, such as the trabecular meshwork.

The dual aiming beam apparatus 450 comprises an aiming beam source 452, an aiming beam telescope 858, and a double aperture 860. In one configuration the aiming beam source 452 is a laser diode configured to output a cone of light 856 as opposed to a discrete beam of light as is done by the aiming beam sources in the first embodiment and the second embodiment. The cone of light 856 is directed into the aiming beam telescope 858. The double aperture 860 placed after the aiming beam telescope 858 masks the cone of light 856, creating discrete aiming beams of parallel light 451a, 451b.

A beam splitter 852 reflects the dual aiming beams of light 451a, 451b such that the aiming beams are co-linear with the femtosecond laser beam 201. The dual aiming beams of light 451a, 451b and the femtosecond laser beam 201 are reflected by a first dichroic mirror 807 into a pair of scanning mirrors 808. An OCT beam 301 is transmitted through the first dichroic mirror 807. Upon transmitting through the dichroic mirror 807, the OCT beam 301 is co-linear with the femtosecond beam 201 and the dual aiming beams of light 451a, 451b. All beams 201, 301, 451a, 451b pass through a pair of scanning mirrors 808 into an expanding telescope 810. The expanding telescope 810 increases the diameter of the femtosecond laser beam 201, the diameter of the OCT beam 301, and the diameters of the dual aiming beams of light 451a and 451b and pre-compensates for astigmatism that will be introduced by the human cornea. The expanded femtosecond beam 203, the expanded OCT beam 303, and the dual aiming beams of light 451a, 451b then transmit through a second dichroic mirror 809 into the focusing objective 814 that focuses the beams onto a single point 816 in a surgical area. In an alternate configuration, the second dichroic mirror 809 may be replaced by a beam splitter.

An illumination beam 401 output by an illumination source of the visual observation apparatus 400 shines visible light through a telescope 818 that collimates the illumination beam 401 onto the second dichroic mirror 809. The second dichroic mirror 809 reflects the illumination beam 401 onto the focusing objective 814. The focusing objective 814 focuses the illumination beam 401 into the surgical area near the point 816.

Light from the surgical area near the point 816 resulting from the illumination beam 401 re-enters the focusing objective 814 and is reflected by the second dichroic mirror 809 into a telescope 818. The telescope 818 focuses the illumination light onto the visual observation apparatus 400 where an image is formed. Additionally, the dual aiming beams of light 451a, 451b from the surgical area at the point 816 re-enter the focusing objective 814. A fraction of light from the dual aiming beams of light 451e, 451f is reflected by the second dichroic mirror 809 into the telescope 818. The telescope 818 focuses the dual aiming beams of light 451e, 451f onto the visual observation apparatus 400 where an image of the aiming beams is formed.

Figure 9A:
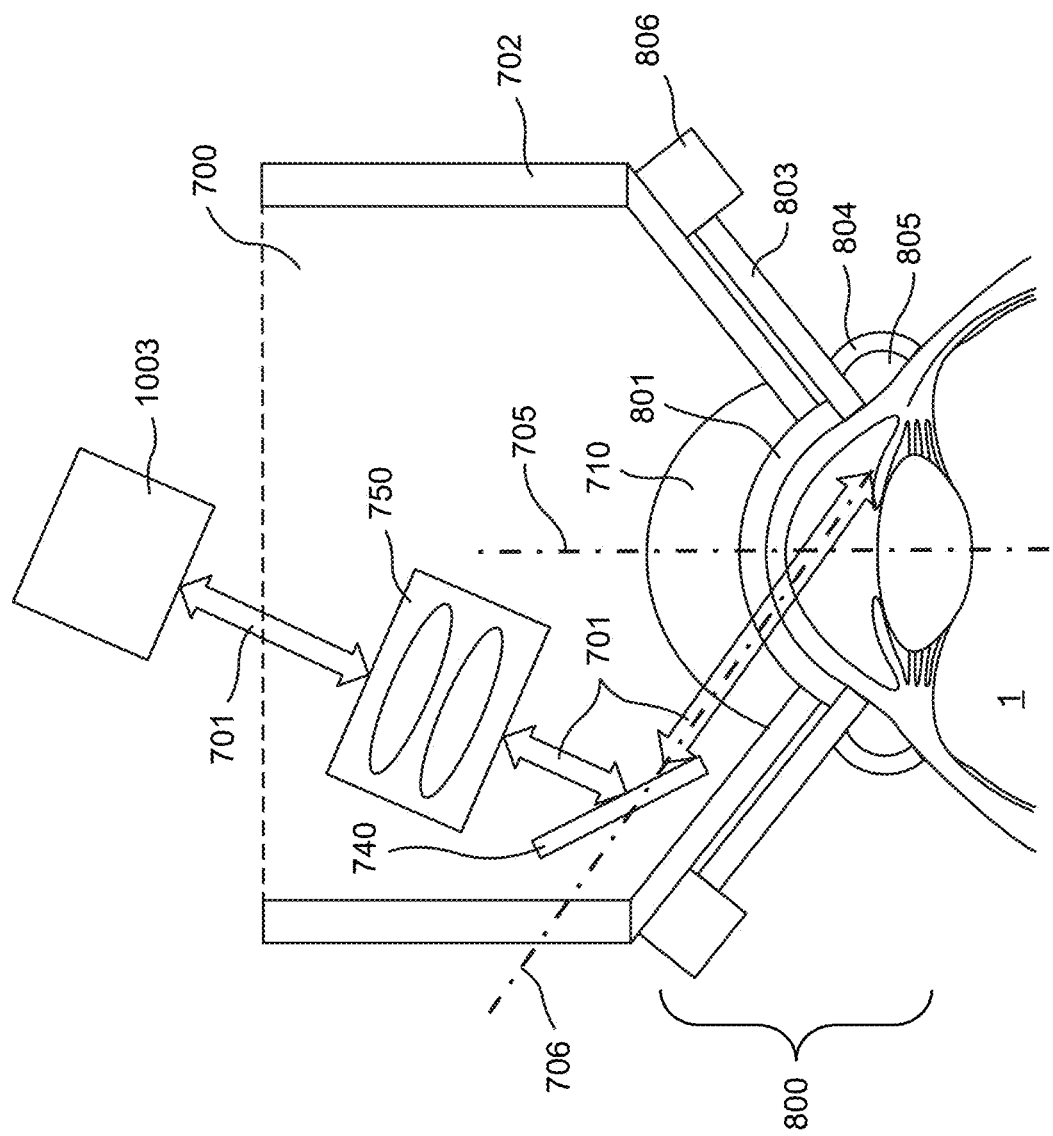

With reference to FIGS. 9A and 9B, in an embodiment of the integrated surgical system 1000, optical components of the focusing objective 700 and patient interface 800 are configured to minimize spatial and chromatic aberrations and spatial and chromatic distortions. FIG. 9A shows a configuration when both the eye 1, the patient interface 800 and the focusing objective 700 all coupled together. FIG. 9B shows a configuration when both the eye 1, the patient interface 800 and the focusing objective 700 all detached from one another.

The patient interface 800 optically and physically couples the eye 1 to the focusing objective 700, which in turn optically couples with other optic components of the integrated surgical system 1000. The patient interface 800 serves multiple functions. It immobilizes the eye relative to components of the integrated surgical system; creates a sterile barrier between the components and the patient; and provides optical access between the eye and the instrument. The patient interface 800 is a sterile, single use disposable device and it is coupled detachably to the eye 1 and to the focusing objective 700 of the integrated surgical system 1000.

Figure 9C:
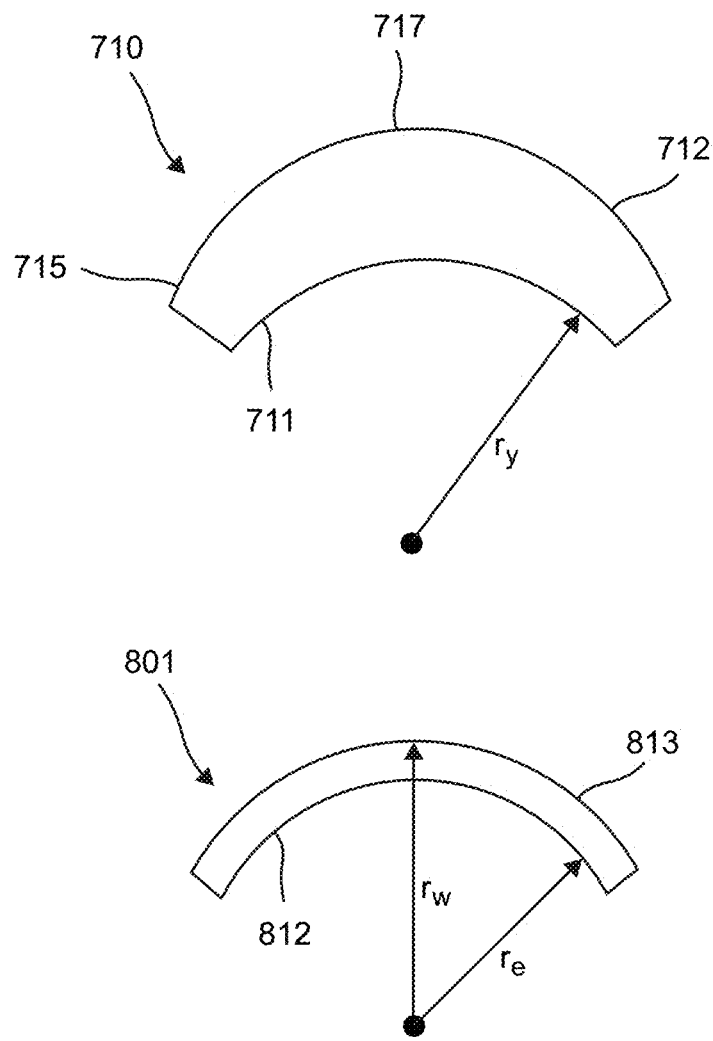
FIG. 9C is a schematic illustration of components of the focusing objective and the patient interface included in FIGS. 9A and 9B.

The patient interface 800 includes a window 801 having an eye-facing, concave surface 812 and an objective-facing, convex surface 813 opposite the concave surface. The window 801 thus has a meniscus form. With reference to FIG. 9C, the concave surface 812 is characterized by a radius of curvature $r_e$, while the convex surface 813 is characterized by a radius of curvature $r_w$. The concave surface 812 is configured to couple to the eye, either through a direct contact or through index matching material, liquid or gel, placed in between the concave surface 812 and the eye 1. The window 801 may be formed of glass and has a refractive index $r_w$. In one embodiment, the window 801 is formed of fused silica and has a refractive index $n_w$ of 1.45.

Fused silica has the lowest index from common inexpensive glasses. Fluoropolymers such as the Teflon AF are another class of low index materials that have refractive indices lower than fused silica, but their optical quality is inferior to glasses and they are relatively expensive for high volume production. In another embodiment the window 801 is formed of the common glass BK7 and has a refractive index $n_w$ of 1.50. A radiation resistant version of this glass, BK7G18 from Schott A G, Mainz, Germany, allows gamma sterilization of the patient interface 800 without the gamma radiation altering the optical properties of the window 801.

Returning to FIGS. 9A and 9B, the window 801 is surrounded by a wall 803 of the patient interface 800 and an immobilization device, such as a suction ring 804. When the suction ring 804 is in contact with the eye 1, an annular cavity 805 is formed between the suction ring and the eye. When vacuum applied to the suction ring 804 and the cavity via a vacuum tube a vacuum pump (not shown in FIGS. 9A and 9B), vacuum forces between the eye and the suction ring attach the eye to the patient interface 800 during surgery. Removing the vacuum releases or detach the eye 1.

The end of the patient interface 800 opposite the eye 1 includes an attachment interface 806 configured to attach to the housing 702 of the focusing objective 700 to thereby affix the position of the eye relative to the other components of the integrated surgical system 1000. The attachment interface 806 can work with mechanical, vacuum, magnetic or other principles and it is also detachable from the integrated surgical system.

The focusing objective 700 includes an aspheric exit lens 710 having an eye-facing, concave surface 711 and a convex surface 712 opposite the concave surface. The exit lens 710 thus has a meniscus form. While the exit lens 710 shown in FIGS. 9A and 9B is an aspheric lens giving more design freedom, in other configurations the exit lens may be a spherical lens. Alternatively, constructing the exit lens 710 as a compound lens, as opposed to a singlet, allows more design freedom to optimize the optics while preserving the main characteristics of the optical system as presented here. With reference to FIG. 9C, the concave surface 711 is characterized by a radius of curvature $r_y$, while the convex surface 712 is characterized by an aspheric shape. The aspheric convex surface 712 in combination with the spherical concave surface 711 result in an exit lens 710 having varying thickness, with the outer perimeter edges 715 of the lens being thinner than the central, apex region 717 of the lens. The concave surface 711 is configured to couple to the convex surface 813 of the window 801. In one embodiment, the exit lens 710 is formed of fused silica and has a refractive index $n_x$ of 1.45.

Figure 10A:
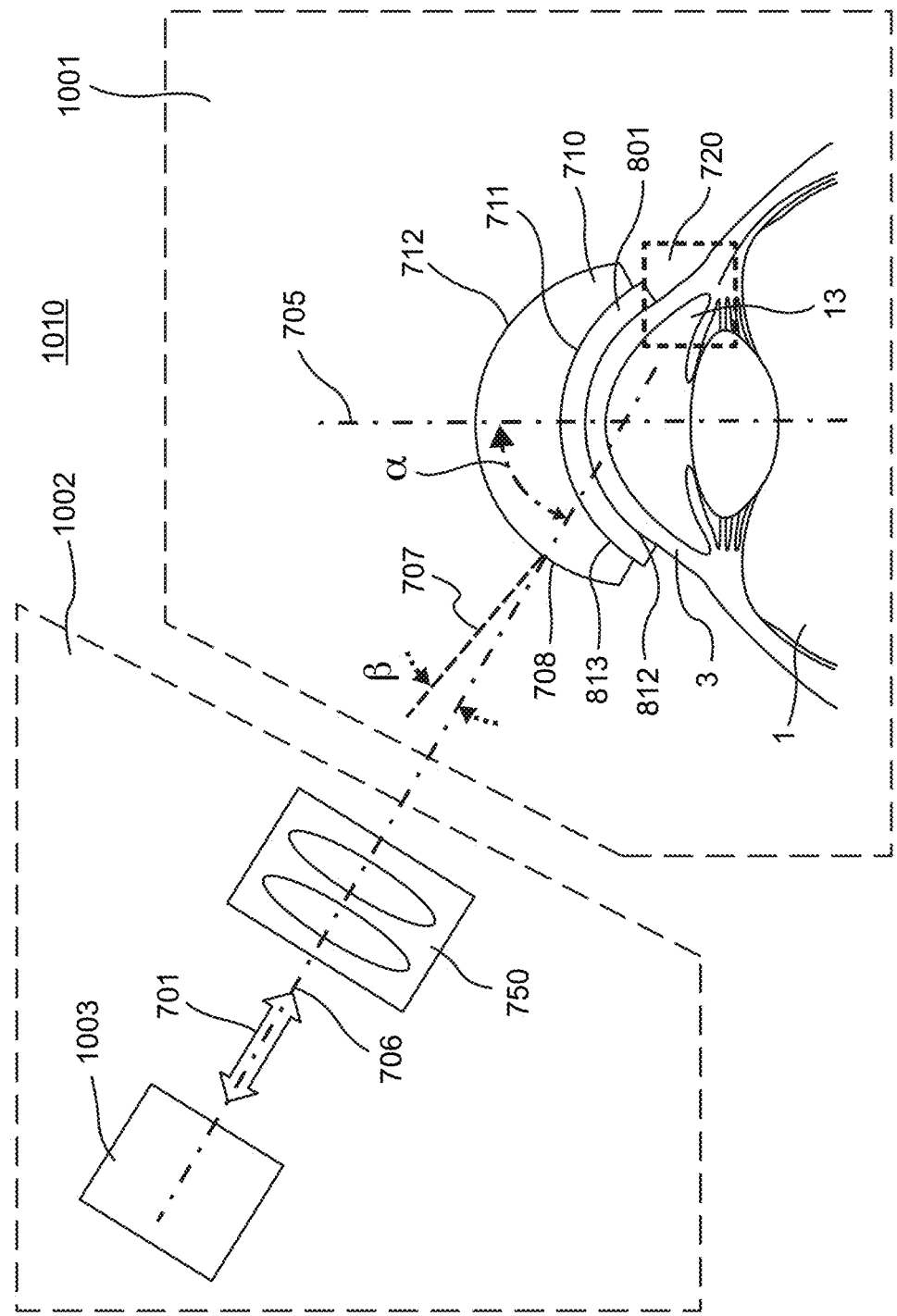
FIGS. 10A and 10B are schematic illustrations of components of the integrated surgical system of FIGS. 7 and 8A functionally arranged to form a first optical system and a second optical subsystem that enable access to the to the irido-corneal angle along the angled beam path of FIG. 6.
Figure 10B:
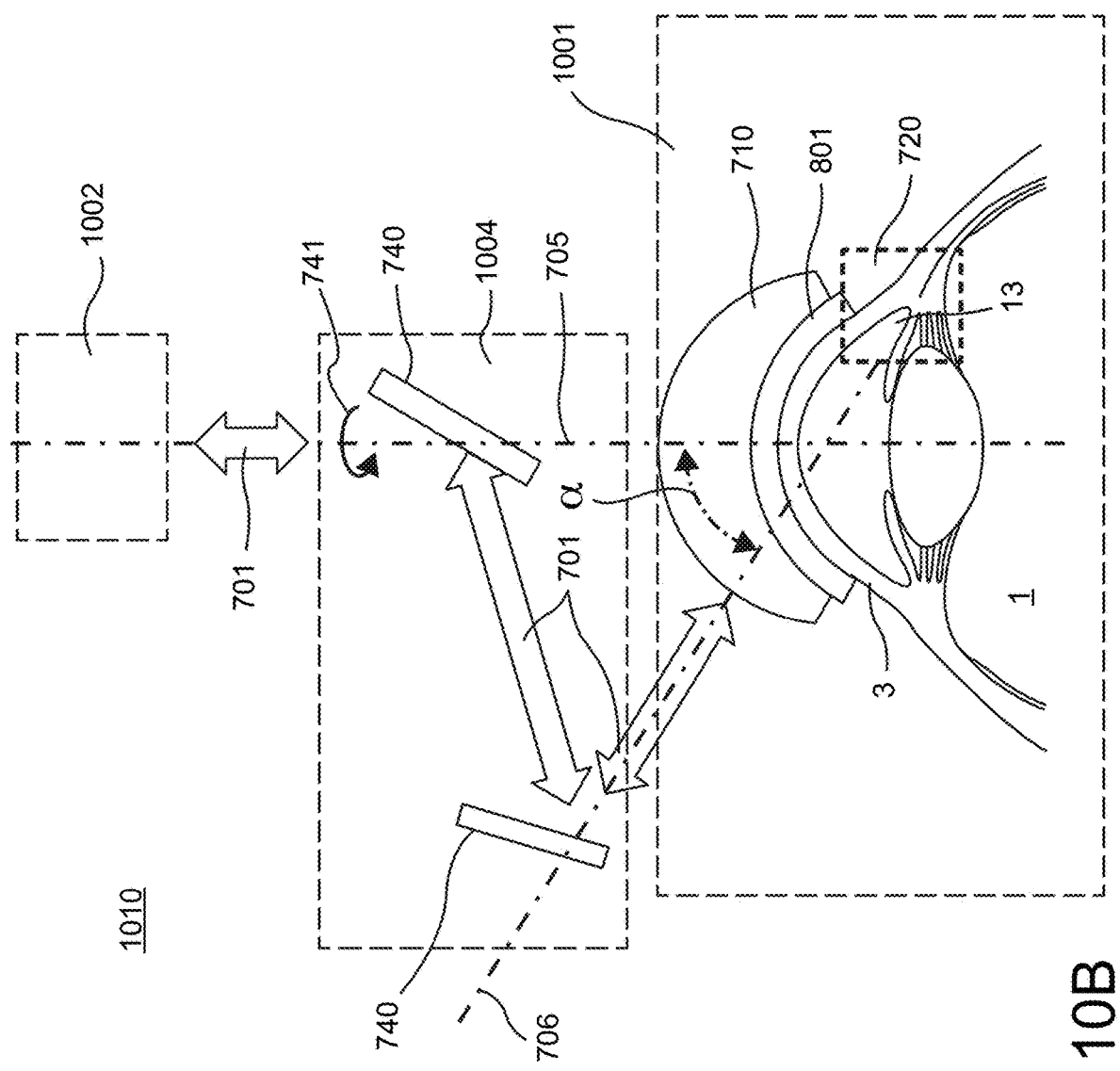
Figure 10C:
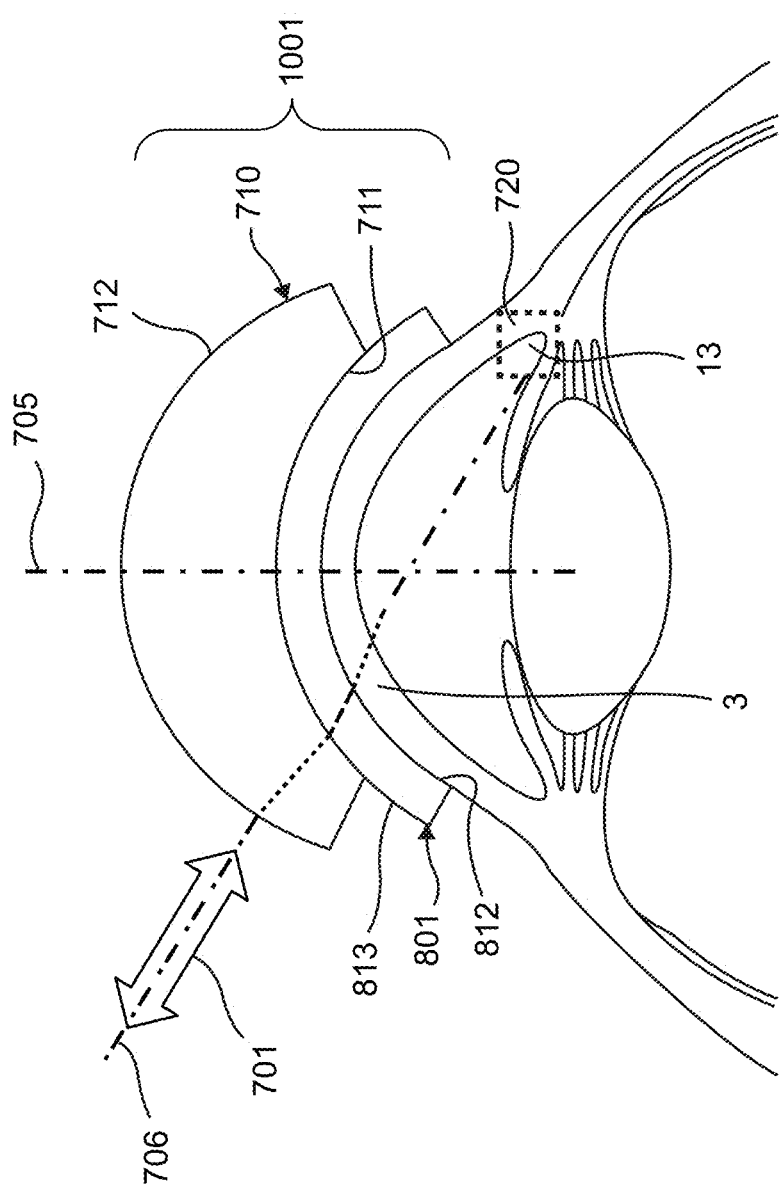
FIG. 10C is a schematic illustration of a beam passing through the first optical subsystem of FIGS. 10A and 10B and into the eye.

FIGS. 10A and 10B are schematic illustrations of components of the integrated surgical system of FIGS. 7 and 8 functionally arranged to form an optical system 1010 having a first optical subsystem 1001 and a second optical subsystem 1002 that enable access to a surgical volume 720 in the irido-corneal angle. Each of FIGS. 10A and 10B include components of the focusing objective 700 and the patient interface 800 of FIG. 9A. However, for simplicity, the entirety of the focusing objective and the patient interface are not included in FIGS. 10A and 10B. Also, for additional simplicity in FIG. 10A, the planar beam-folding mirror 740 of FIGS. 9A and 9B is not included and the combined laser/OCT/illumination beam 701 shown in FIG. 9A is unfolded or straightened out. It is understood by those skilled in the art that adding or removing planar beam folding mirrors does not alter the principal working of the optical system formed by the first optical subsystem and the second optical subsystem. FIG. 10C is a schematic illustration of a beam passing through the first optical subsystem of FIGS. 10A and 10B.

With reference to FIG. 10A, a first optical subsystem 1001 of the integrated surgical system 1000 includes the exit lens 710 of a focusing objective 700 and the window 801 of a patient interface 800. The exit lens 710 and the window 801 are arranged relative to each other to define a first optical axis 705. The first optical subsystem 1001 is configured to receive a beam, e.g., a combined laser/OCT/illumination/aiming beam 701, incident at the convex surface 712 of the exit lens 710 along a second optical axis 706, and to direct the beam toward a surgical volume 720 in the irido-corneal angle 13 of the eye.

During a surgical procedure, the first optical subsystem 1001 may be assembled by interfacing the convex surface 813 of the window 801 with the concave surface 711 of the exit lens 710. To this end, a focusing objective 700 is docked together with a patient interface 800. As a result, the concave surface 711 of the exit lens 710 is coupled to the convex surface 813 of the window 801. The coupling may be by direct contact or through a layer of index matching fluid. For example, when docking the patient interface 800 to focusing objective 700, a drop of index matching fluid can be applied between the contacting surfaces to eliminate any air gap that may be between the two surfaces 711, 813 to thereby help pass the combined laser/OCT/illumination/aiming beam 701 through the gap with minimal Fresnel reflection and distortion.

In order to direct the combined laser/OCT/illumination/aiming beam 701 toward the surgical volume 720 in the irido-corneal angle 13 of the eye, the first optical subsystem 1001 is designed to account for refraction of the beam 701 as it passes through the exit lens 710, the window 801 and the cornea 3. To this end, and with reference to FIG. 10C, the refractive index $n_x$ of the exit lens 710 and the refractive index $n_w$ of the window 801 are selected in view of the refractive index $n_c$ of the cornea 3 to cause appropriate beam bending through the first optical subsystem 1001 so that when the combined laser/OCT/illumination/aiming beam 701 exits the subsystem and passes through the cornea 3, the beam path is generally aligned to fall within the irido-corneal angle 13.

Continuing with reference to FIG. 10C and beginning with the interface between the window 801 and the cornea 3. Too steep of an angle of incidence at the interface where the combined laser/OCT/illumination/aiming beam 701 exits the window 801 and enters the cornea 3, i.e., at the interface between the concave surface 812 of the window and the convex surface of the cornea 3, can create excessive refraction and distortion. To minimize refraction and distortion at this interface, in one embodiment of the first optical subsystem 1001, the refractive index of the window 801 is closely matched to the index of the cornea 3. For example, as describe above with reference to FIGS. 9A and 9B, the window 801 may have a refractive index lower than 1.42 to closely match the cornea 3, which has a refractive index of 1.36.

Excessive refraction and distortion at the interface where the combined laser/OCT/illumination/aiming beam 701 exits the window 801 and enters the cornea 3 may be further compensated for by controlling the bending of the beam 701 as it passes through the exit lens 710 and the window 801. To this end, in one embodiment of the first optical subsystem 1001 the index of refraction $n_w$ of the window 801 is larger than each of the index of refraction $n_x$ of the exit lens 710 and the index of refraction $n_c$ of the cornea 3. As a result, at the interface where the combined laser/OCT/illumination/aiming beam 701 exits the exit lens 710 and enters the window 801, i.e., interface between the concave surface 711 of the exit lens and the convex surface 813 of the window, the beam passes through a refractive index change from high to low that cause the beam to bend in a first direction. Then, at the interface where the combined laser/OCT/illumination/aiming beam 701 exits the window 801 and enters the cornea 3, i.e., interface between the concave surface 812 of the exit lens and the convex surface of the cornea, the beam passes through a refractive index change from low to high that cause the beam to bend in a second direction opposite the first direction.

The shape of the window 801 is chosen to be a meniscus lens. As such, the incidence angle of light has similar values on both surfaces 812, 813 of the window 801. The overall effect is that at the convex surface 813 the light bends away from the surface normal and at the concave surface 812 the light bends towards the surface normal. The effect is like when light passes through a plan parallel plate. Refraction on one surface of the plate is compensated by refraction on the other surface a light passing through the plate does not change its direction. Refraction at the entering, convex surface 712 of the exit lens 710 distal to the eye is minimized by setting the curvature of the entering surface such that angle of incidence $\beta$ of light 701 at the entering surface is close to a surface normal 707 to the entering surface at the intersection point 708.

Here, the exit lens 710, the window 801, and the eye 1 are arranged as an axially symmetric system with a first optical axis 705. In practice, axial symmetry is an approximation because of manufacturing and alignment inaccuracies of the optical components, the natural deviation from symmetry of the eye and the inaccuracy of the alignment of the eye relative to the window 801 and the exit lens 710 in a clinical setting. But, for design and practical purposes the eye 1, the window 801, and the exit lens 710 are considered as an axially symmetric first optical subsystem 1001.

With continued reference to FIG. 10A, a second optical subsystem 1002 is optically coupled to the first optical subsystem 1001 at an angle $\alpha$ relative to the first optical axis 705 of the first optical subsystem 1001. The advantage of this arrangement is that the both optical subsystems 1001, 1002 can be designed at a much lower numerical aperture compared to a system where all optical components are designed on axis with a common optical axis.

The second optical subsystem 1002 includes an objective lens 750 that, as previously described with reference to FIG. 8A, generates a conjugate surgical volume 721 of the surgical volume 720 within the eye. The second optical subsystem 1002 includes various other components collectively indicated as an optical subsystem step 1003. Referring to FIG. 8A, these components may include a femtosecond laser source 200, an OCT imaging apparatus 300, a visual observation apparatus 400, an dual aiming beam apparatus 450, beam conditioners and scanners 500, and beam combiners 600.

The second optical subsystem 1002 may include mechanical parts (not shown) configured to rotate the entire subsystem around the first optical axis 705 of the first optical subsystem 1001. This allows optical access to the whole 360-degree circumference of the irido-corneal angle 13 of the eye 1.

With reference to FIG. 10B, flexibility in arranging the first and second optical subsystems 1001, 1002, relative to each other may be provided by an optical assembly 1004 interposed between the optical output of the second optical subsystem 1002 and the optical input of the first optical subsystem 1001. In one embodiment, the optical assembly 1004 may include one or more planar beam-folding mirrors 740, prisms (not shown) or optical gratings (not shown) configured to receive the optical output, e.g., combined laser/OCT/illumination beam 701, of the second optical subsystem 1002, change or adjust the direction of the combined laser/OCT/illumination beam, and direct the beam to the optical input of the first optical subsystem 1001 while preserving the angle $\alpha$ between the first optical axis 705 and the second optical axis 706.

In another configuration, the optical assembly 1004 of planar beam-folding mirrors 740 further includes mechanical parts (not shown) configured to rotate the assembly around the first optical axis 705 of the first optical subsystem 1001 while keeping the second optical subsystem 1002 stationary. Accordingly, the second optical axis 706 of the second optical subsystem 1002 can be rotated around the first optical axis 705 of the first optical subsystem 1001. This allows optical access to the whole 360-degree circumference of the irido-corneal angle 13 of the eye 1.

With considerations described above with reference to FIGS. 9A, 9B and 9C, the design of the first optical subsystem 1001 is optimized for angled optical access at an angle $\alpha$ relative to the first optical axis 705 of the first optical subsystem 1001. Optical access at the angle $\alpha$ compensates for optical aberrations of the first optical subsystem 1001. Table 1 shows the result of the optimization at access angle $\alpha$=72 degrees with Zemax optical design software package. This design is a practical embodiment for image guided femtosecond glaucoma surgery.

TABLE 1

| Surface | Structure and Material | Refractive index | Radius [mm] | Center Thickness [mm] |
|---|---|---|---|---|
| concave surface 711, convex surface 712 | Exit lens 710 of focusing objective. Fused silica | 1.45 | −10 | 4.5 |
| concave surface 812, convex surface 813 | Window 801 of patient interface. BK7G18 | 1.50 | −10.9 | 1.0 |
| 3 | Cornea | 1.36 | −7.83 | 0.54 |
| 8 | Aqueous humor | 1.32 | −6.53 | 3.5 |
| Target | Ophthalmic tissue | 1.38 | N/A | 0 to 1 mm |

This design produces diffraction limited focusing of 1030 nm wavelength laser beams and 850 nm wavelength OCT beams with numerical aperture (NA) up to 0.2. In one design, the optical aberrations of the first optical subsystem are compensated to a degree that the Strehl ratio of the first optical subsystem for a beam with numerical aperture larger than 0.15 at the irido-corneal angle is larger than 0.9. In another design, the optical aberrations of the first optical subsystem are partially compensated, the remaining uncompensated aberrations of the first optical system are compensated by the second optical subsystem to a degree that the Strehl ratio of the combined first and second optical subsystem for a beam with numerical aperture larger than 0.15 at the irido-corneal angle is larger than 0.9.

Laser Surgical Patterns and Parameters

Figure 11:
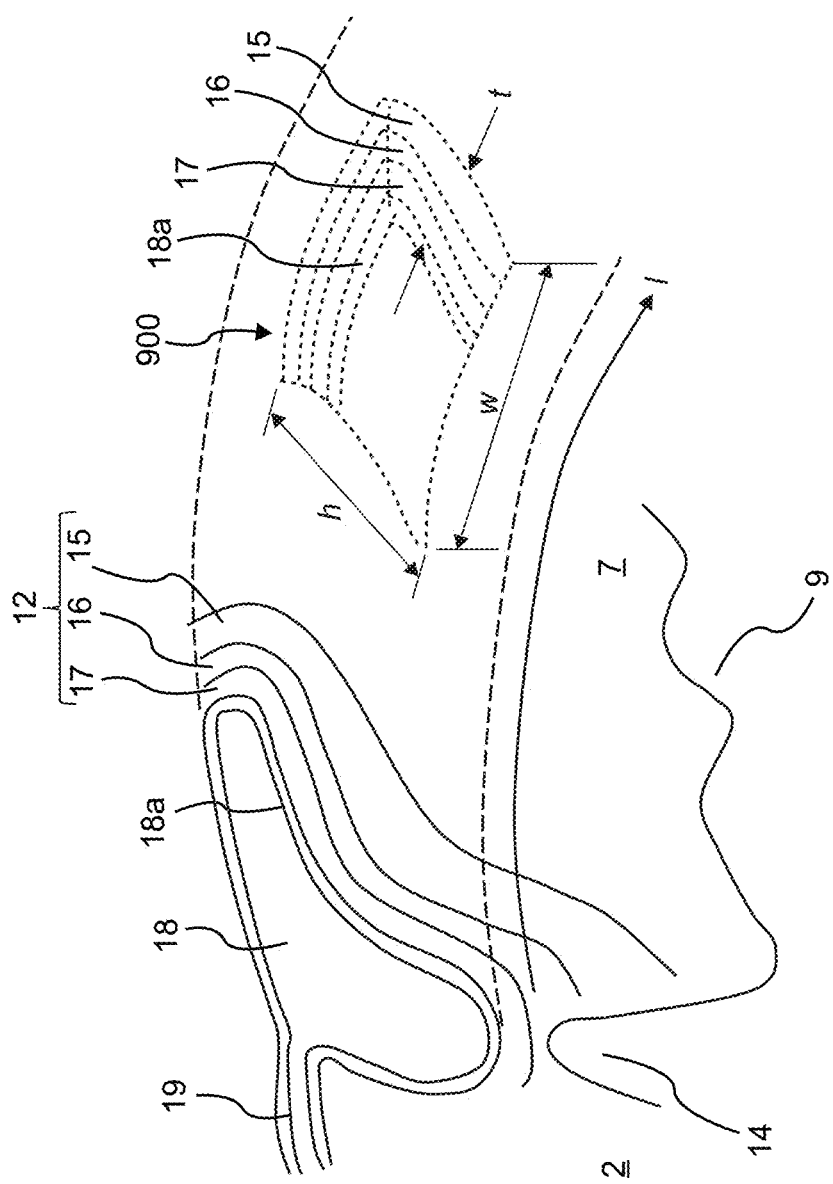
FIG. 11 is a three-dimensional schematic illustration of anatomical structures in the irido-corneal angle, including the trabecular meshwork, Schlemm's canal, a collector channel branching from the Schlemm's canal, and a surgical volume of ocular tissue to be treated by the integrated surgical system of FIG. 7.

FIG. 11 is a three-dimensional schematic illustration of anatomical structures of the eye relevant to the surgical treatment enabled by the integrated surgical system 1000. To reduce the IOP, laser treatment targets ocular tissues that affect the trabecular outflow pathway 40. These ocular tissues may include the trabecular meshwork 12, the scleral spur 14, the Schlemm's canal 18, and the collector channels 19. The trabecular meshwork 12 has three layers, the uveal meshwork 15, the corneoscleral meshwork 16, and the juxtacanalicular tissue 17. These layers are porous and permeable to aqueous, with the uveal meshwork 15 being the most porous and permeable, followed by the corneoscleral meshwork 16. The least porous and least permeable layer of the trabecular meshwork 12 is the juxtacanalicular tissue 17. The inner wall 18a of the Schlemm's canal 18, which is also porous and permeable to aqueous, has characteristics similar to the juxtacanalicular tissue 17.

Figure 12:
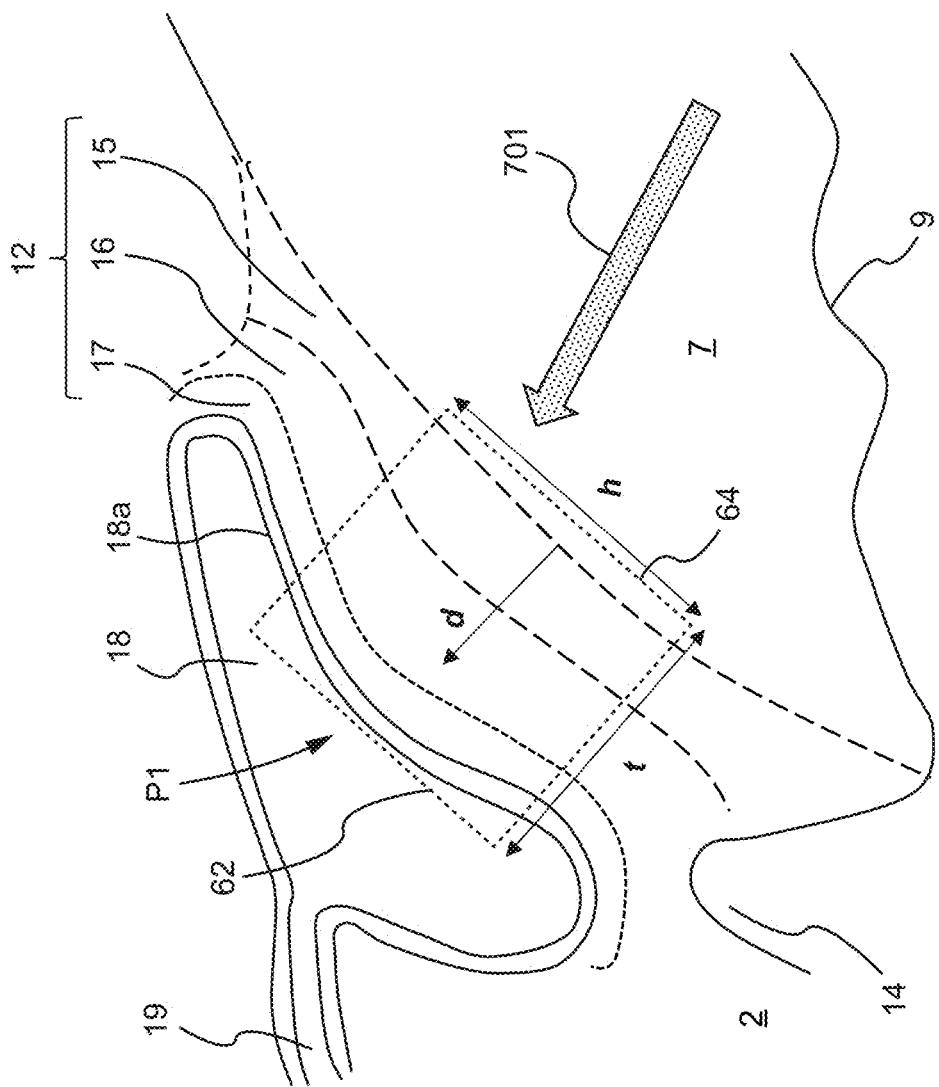
FIG. 12 is a two-dimensional schematic illustration of anatomical structures in the irido-corneal angle and a laser treatment pattern to be applied by the integrated surgical system of FIG. 7 to affect the surgical volume of ocular tissue between the Schlemm's canal and the anterior chamber, as shown in FIG. 11.
Figure 12:
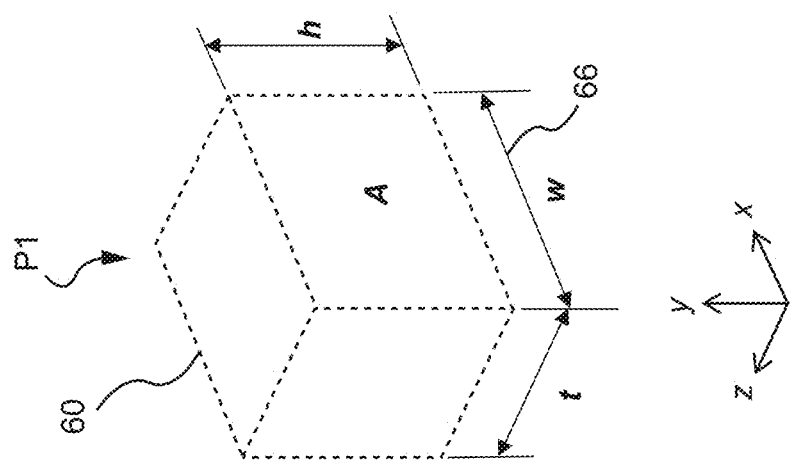

FIG. 12 includes a three-dimensional illustration of a treatment pattern P1 to be applied by the integrated surgical system 1000 to affect the surgical volume 900 of ocular tissue shown in FIG. 11, and a two-dimensional schematic illustration of a treatment pattern P1 overlaying the anatomical structures to be treated. The OCT imaging apparatus 300 of the integrated surgical system 1000 may present a visual image of the anatomical structures similar to the two-dimensional schematic illustration in FIG. 12.

Figure 13:
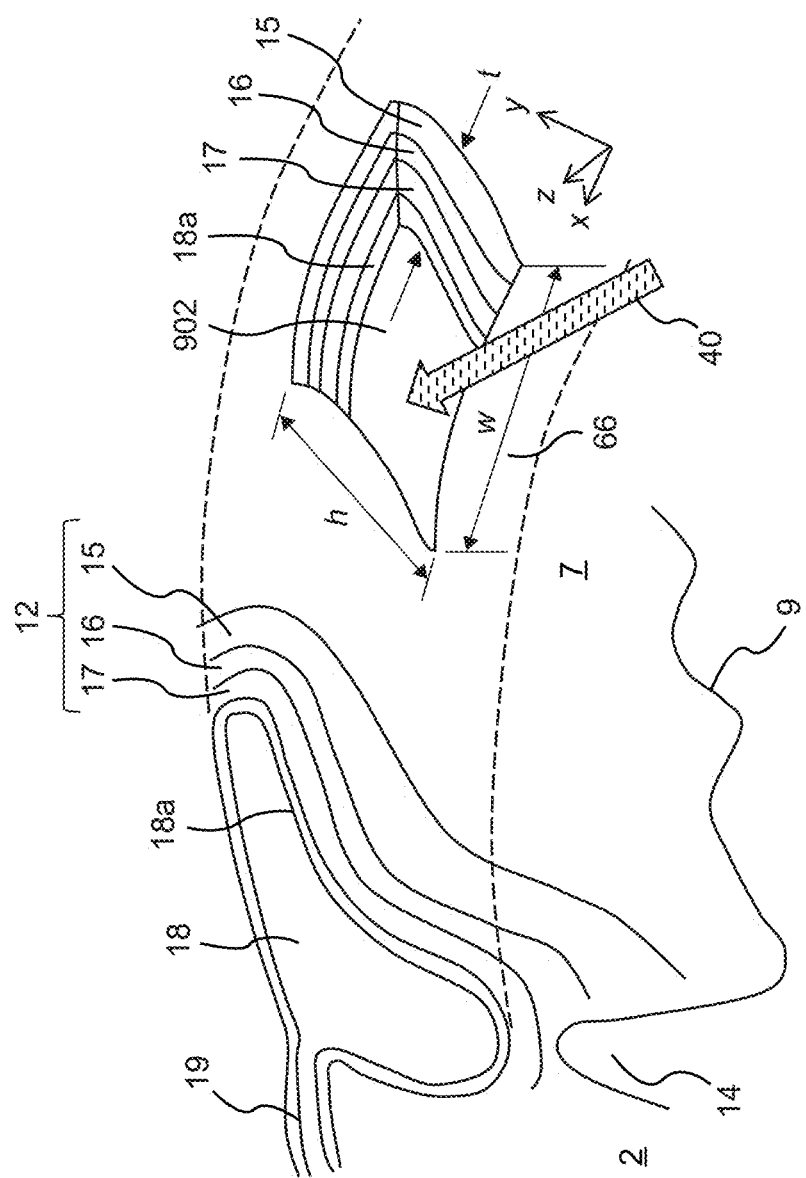
FIG. 13 is a three-dimensional schematic illustration of FIG. 11 subsequent to treatment of the surgical volume of ocular tissue by a laser based on the laser treatment pattern of FIG. 12 that forms an opening between the Schlemm's canal and the anterior chamber.

FIG. 13 is a three-dimensional schematic illustration of the anatomical structures of the eye including an opening 902 through the trabecular meshwork 12 and the inner wall 18a of the Schlemm's canal 18 that results from the application of the laser treatment pattern P1 of FIG. 12. The opening 902 resembles the surgical volume 900 and provides a trabecular outflow pathway 40 that reduces the flow resistance in the ocular tissue to increase aqueous flow from the anterior chamber 7 into the Schlemm's canal 18 and thereby reduce the TOP of the eye. The opening 902 may be a continuous, single lumen defining a fluid pathway, or may be defined by an arrangement of adjacent pores forming a sponge like structure defining a fluid pathway or a combination thereof.

The treatment pattern P1 defines a laser scanning procedure whereby a laser is focused at different depth locations in ocular tissue and then scanned in multiple directions to affect a three-dimensional volume of tissue comprising multiple sheets or layers of affected tissue. A treatment pattern is considered to define a collection of a laser-tissue interaction volumes, referred to herein as cells. The size of a cell is determined by the extent of the influence of the laser-tissue interaction. When the laser cells are spaced close along a line, the laser creates a narrow, microscopic channel. A wider channel can be created by closely spacing a multitude of laser cells within the cross section of the channel. The arrangement of the cells may resemble the arrangement of atoms in a crystal structure.

A treatment pattern P1 may be in the form of a cubic structure that encompasses individual cells arranged in regularly spaced rows, columns and sheets or layers. The treatment pattern P1 may be characterized by x, y, z dimensions, with x, y, z coordinates of the cells being calculated sequentially from neighbor to neighbor in the order of a column location (x coordinate), a row location (y coordinate), and a layer location (z coordinate). A treatment pattern P1 as such, defines a three-dimensional model of ocular tissue to be modified by a laser or a three-dimensional model of ocular fluid to be affected by a laser.

A treatment pattern P1 is typically defined by a set of surgical parameters. The surgical parameters may include one or more of a treatment area A that represents a surface area or layer of ocular tissue through which the laser will travel. The treatment area A is determined by the treatment height, h, and the width or lateral extent 66 of the treatment, w. The lateral extent 66 may be defined in terms of a measure around the circumferential angle. For example, the lateral extent 66 w may be defined in terms of an angle, e.g., 90 degrees, around the circumferential angle. A treatment thickness t that represents the level to which the laser will cut into the ocular tissue from the distal extent 62 or border of the treatment volume at or near the inner wall 18a of the Schlemm's canal 18 to the proximal extent 64 or border at or near the surface of the trabecular meshwork 12. Thus, a laser applied in accordance with a treatment pattern may affect or produce a surgical volume that resembles the three-dimensional model of the treatment pattern, or may affect fluid located in an interior of an eye structure resembled by the three-dimensional model.

Additional surgical parameters define the placement of the surgical volume or affected volume within the eye. For example, with reference to FIGS. 11 and 12, placement parameters may include one or more of a location 1 that represents where the treatment is to occur relative to the circumferential angle of the eye, and a treatment depth d that represents a position of the three-dimensional model of ocular tissue or ocular fluid within the eye relative to a reference eye structure. In the following, the treatment depth d is shown and described relative to the region where the anterior chamber 7 meets the trabecular meshwork 12. Together, the treatment pattern and the placement parameters define a treatment plan.

As previously mentioned, the laser treatment described herein involves photodisruption by a femtosecond laser. A femtosecond laser provides highly localized, non-thermal photo-disruptive laser-tissue interaction with minimal collateral damage to surrounding ocular tissue. Photo-disruptive interaction of the laser is utilized in optically transparent tissue. The principal mechanism of laser energy deposition into the ocular tissue is not by absorption but by a highly nonlinear multiphoton process. This process is effective only at the focus of the pulsed laser where the peak intensity is high. Regions where the beam is traversed but not at the focus are not affected by the laser. Therefore, the interaction region with the ocular tissue is highly localized both transversally and axially along the laser beam.

During a laser scanning procedure, a laser focus is moved to different depths d in ocular tissue and then scanned in two lateral dimensions or directions as defined by a treatment pattern P1 to affect a three-dimensional volume 900 of ocular tissue comprising multiple sheets or layers of affected tissue. The two lateral dimensions are generally orthogonal to the axis of movement of the laser focus. With reference to FIG. 13, the movement of a laser focus during laser scanning is described herein with reference to x, y, and z directions or axes. Movement of the laser focus to different depths d through the thickness t of treatment pattern P1 or the volume 900 of tissue corresponds to movement of the focus along the z axis. The focal point of the laser in the z direction may be referred to as a depth d within the treatment pattern P1 or the volume 900 of tissue.

Movement of the laser focus in two dimensions or directions orthogonal to the z axis corresponds to movement of the laser focus along the width w of the treatment pattern P1 or the volume 900 of tissue in the x direction, and movement of the laser focus along the height h of the treatment pattern P1 or the volume 900 of tissue in the y direction. The two direction or dimension scanning of the laser focus may be in the form of a raster scan and defines a layer of laser scanning, which in turn produces a layer of laser-affected tissue.

During laser scanning, pulse shots of a laser are delivered to tissue within the volume of ocular tissue corresponding to the treatment pattern P1. Because the laser interaction volume is small, on the order of a few micrometers (m), the interaction of ocular tissue with each laser shot of a repetitive laser breaks down ocular tissue locally at the focus of the laser. Pulse duration of the laser for photo-disruptive interaction in ocular tissue can range from several femtoseconds to several nanoseconds and pulse energies from several nanojoules to tens of microjoules. The laser pulses at the focus, through multiphoton processes, breaks down chemical bonds in the molecules, locally photo-dissociate tissue material and create gas bubbles in wet tissue. The breakdown of tissue material and mechanical stress from bubble formation fragments the tissue and create clean continuous cuts when the laser pulses are laid down in proximity to one another along geometrical lines and surfaces.

Laser Surgical Treatment with Tissue Surface Detection

As noted above, a femtosecond laser provides highly localized laser-tissue interaction that creates a cutting effect in tissue at the focus of the femtosecond laser beam. During a laser treatment procedure, surgical femtosecond lasers are tightly focused to a spot at a predetermined location distal to the focusing optics or objective of the surgical system. Having created such a focus and prior to beginning a laser treatment, it is desirable to locate or detect a target surface of ocular tissue on which to place a focus for scanning during a laser treatment, and additionally to locate one or more target sub-surface tissues relative to the target surface.

The integrated surgical system 1000 described above with reference to FIGS. 8A and 8B may be configured to detect or locate a target surface of ocular tissue and relative target sub-surface tissues. For example, a dual aiming beam apparatus 450, either alone or in combination with an OCT imaging apparatus 300, may be used to detect or locate a target surface. Subsequent to detection of a target sub-surface, the OCT imaging apparatus 300 may be used to detect or locate target sub-surfaces.

Figure 14A:
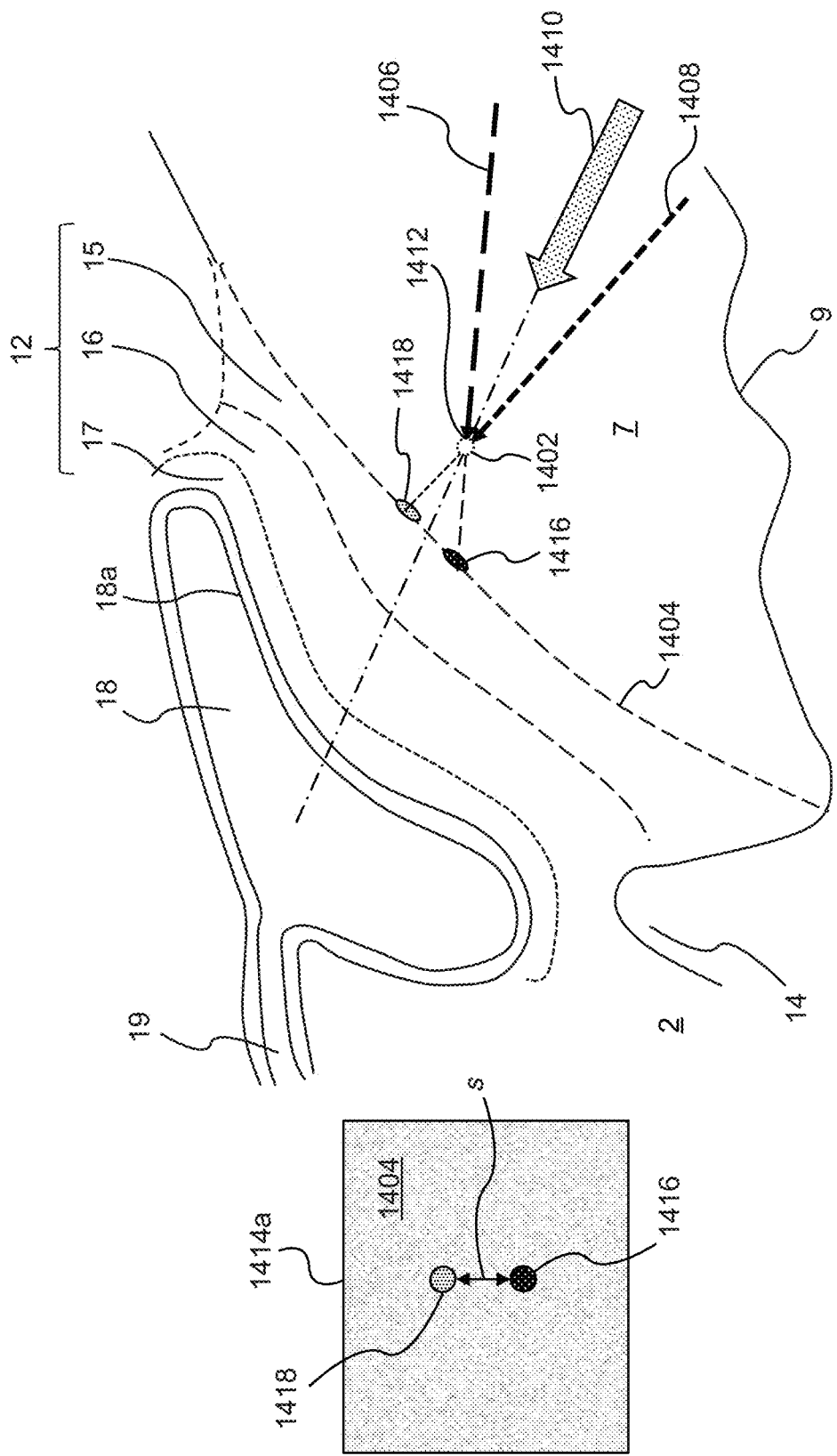
FIGS. 14A, 14B, and 14C are a series of a schematic illustrations of a focus of a femtosecond laser and dual aiming beams with corresponding spots of light on a target surface of ocular tissue as the focus is advanced from the anterior chamber (FIG. 14A), into the trabecular meshwork (FIG. 14B), and back to the target surface (FIG. 14C).

Regarding detection of a target surface, and with reference to FIG. 14A, a first aiming beam of light 1406 and a second aiming beam of light 1408 are directed by an optics subsystem of the surgical system 1000 to be incident with the target surface 1404, which may be, for example, a surface of the trabecular meshwork 12 facing the anterior chamber 7. The first aiming beam of light 1406 and the second aiming beam of light 1408 are aligned relative to each other and relative to a femtosecond laser beam 1410 such that the first aiming beam of light and the second aiming beam of light intersect at a point 1412 corresponding to a focus 1402 of the femtosecond laser beam. In other words, the first aiming beam of light 1406 and the second aiming beam of light 1408 cross each other at a location that is the same as the location of the focus 1402 of the laser beam, or at a location that is nearly the same as the focus or within a measure of tolerance of the focus. This alignment is maintained throughout movement of the focus 1402 of the femtosecond laser beam 1410. An image 1414a of the target surface 1404 captured by the integrated surgical system 1000 includes a first spot 1416 corresponding to the first aiming beam of light 1406 and a second spot 1418 corresponding to a second aiming beam of light 1408. In FIG. 14A, because the focus 1402 of the femtosecond laser beam 1410 is in the anterior chamber 7 some distance from the target surface 1404 of ocular tissue, the first spot 1416 and the second spot 1418 are spaced apart from each other by a distance s, with the second spot being above the first spot.

Figure 14B:
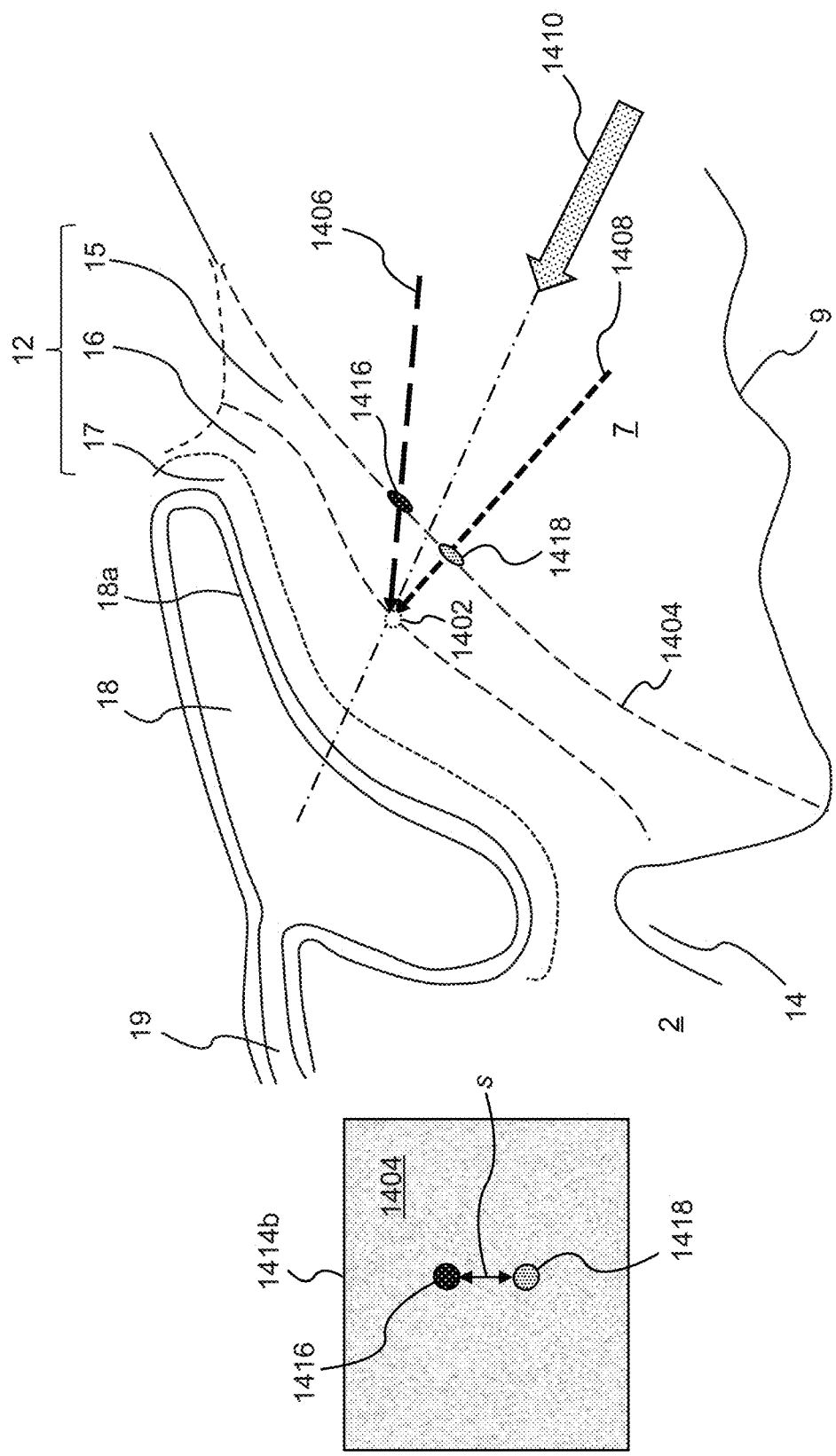

With reference to FIG. 14B, the focus 1402 of the femtosecond laser beam 1410 is moved inside the eye 1 in the direction of propagation of the femtosecond laser beam towards and into the trabecular meshwork 12. The focus 1402 may be moved by the control system 100, either automatically or under operation of a surgeon. Because the focus 1402 of the femtosecond laser beam 1410 is in the trabecular meshwork 12, an image 1414b of the target surface 1404 captured by the integrated surgical system 1000 also includes a first spot 1416 corresponding to the first aiming beam of light 1406 spaced apart by a distance s from a second spot 1418 corresponding to a second aiming beam of light 1408. Comparing this image 1414b to the image of FIG. 14A, it is noted that the relative positions of the spots 1416, 1418 has changed, with the first spot now being above the second spot. This change in position between the spots 1416, 1418 may be used to determine the general location, e.g., either in the anterior chamber 7 (FIG. 14A) or in the trabecular meshwork 12 (FIG. 14B), of the focus 1402 of the femtosecond laser beam 1410 and when that general location has changed. Also, as the femtosecond laser beam 1410 is moved about in the eye, the change in distance s between the spots 1416, 1418 provides an indication of whether the focus 1402 is getting closer too or further from the target surface 1404.

Figure 14C:
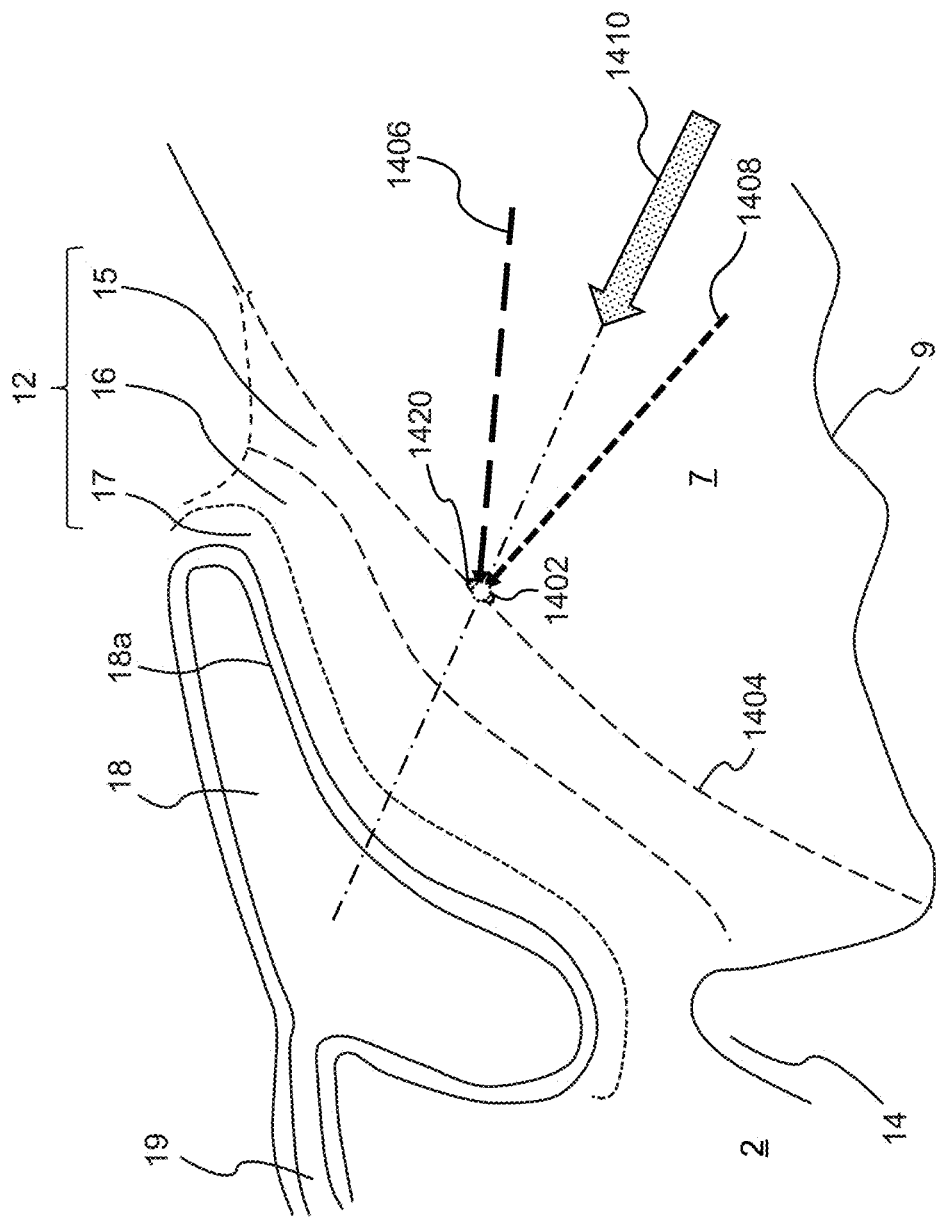
Figure 14C:
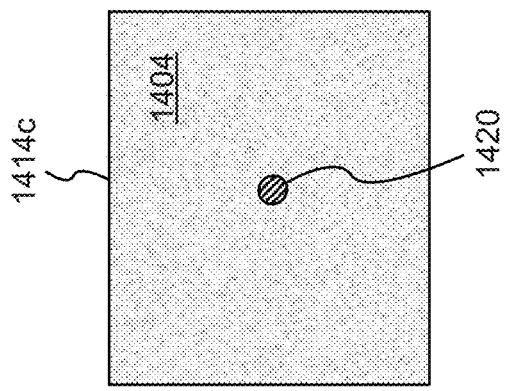

With reference to FIG. 14C, the focus 1402 of the femtosecond laser beam 701 is moved to a location where an image 1414c of the target surface 1404 captured by the integrated surgical system 1000 includes a single spot 1420 that results from an overlap or coalescence of the first spot 1416 corresponding to the first aiming beam of light 1406 and the second spot 1418 corresponding to a second aiming beam of light 1408. This single spot 1420 provides an indication that the focus 1402 of the femtosecond laser beam 1410 is at or on the target surface 1404.

Having determined the focus 1402 of the femtosecond laser beam 1410 is at or on the target surface 1404 based on the dual aiming beam apparatus 450, photodisruption of a target volume of ocular tissue may be initiated. For example, with reference to FIG. 12 a target volume of ocular tissue 60 having a proximal extent 64 at or on the target surface 1404 may be treated by raster scanning the focus 1402 of the femtosecond laser beam 1410 through multiple layers of tissue beginning at the target surface. With reference to FIG. 13, photodisruption of the multiple layers forms an opening 902 between the anterior chamber 7 and the Schlemm's canal 18, thus completing the laser treatment procedure.

Figure 15A:
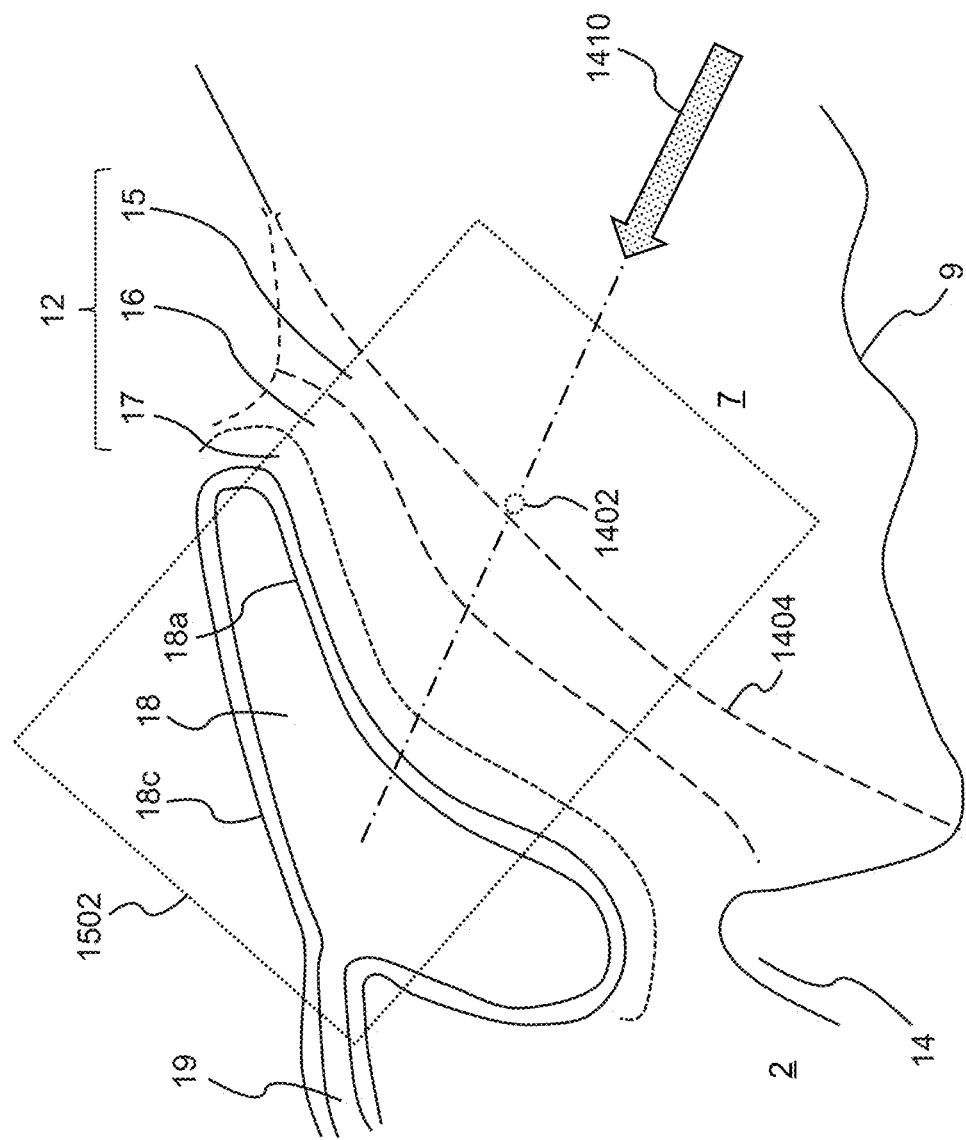
FIGS. 15A-15D are schematic illustrations of OCT images showing a focus of a femtosecond laser at or on a target surface of ocular tissue and spaced apart various distances from target sub-surface tissues.

In some cases, however, detection of the target surface 1404 based on the dual aiming beam apparatus 450 alone may not result in precise placement of the focus 1402 of the femtosecond laser beam 1410 on the target surface. For example, with reference to FIG. 15A, the focus 1402 of the femtosecond laser beam 1410 placed under guidance by a dual aiming beam apparatus 450 may be spaced apart from the target surface 1404. To more precisely place the focus 1402 on the target surface 1404, an OCT image 1502 captured by an OCT imaging apparatus 300 may be used to further detect or located the target surface 1404 and more precisely place the focus in the target surface prior to initiating photodisruption. To this end, a distance between the placement of the focus 1402 of the femtosecond laser beam 1410 and the target surface 1404 may be detected in an OCT image 1502, either visually by a surgeon or automatically by an algorithm executed by a processor in the control system 100. The surgical system 1000 may then automatically advance the focus 1402 of the femtosecond laser beam 1410, under guidance by a processor analyzing the OCT image 1502, until the processor determines that the focus 1402 is on the target surface 1404. Alternatively, the surgical system 1000 may advance the focus 1402 of the femtosecond laser beam 1410 under manual guidance by a surgeon.

Figure 15B:
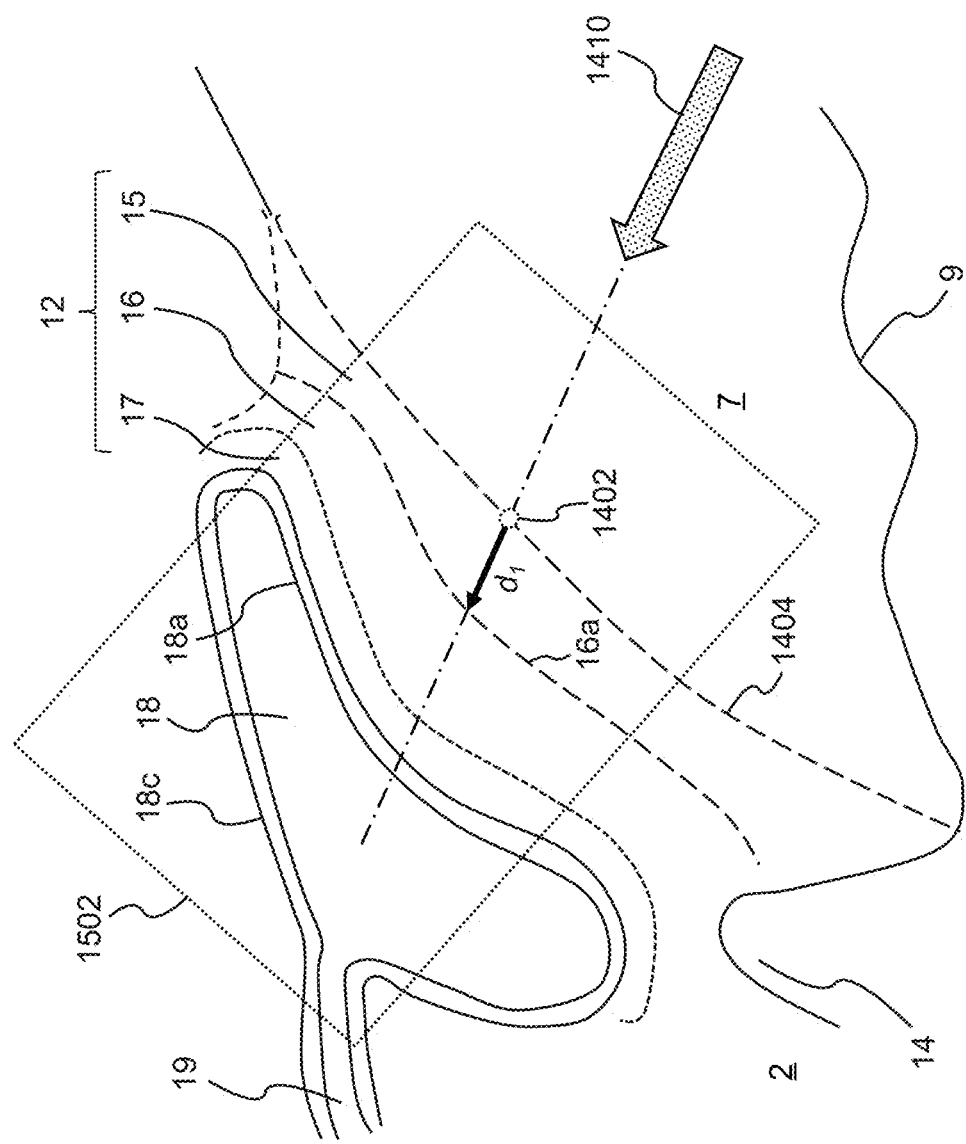
Figure 15C:
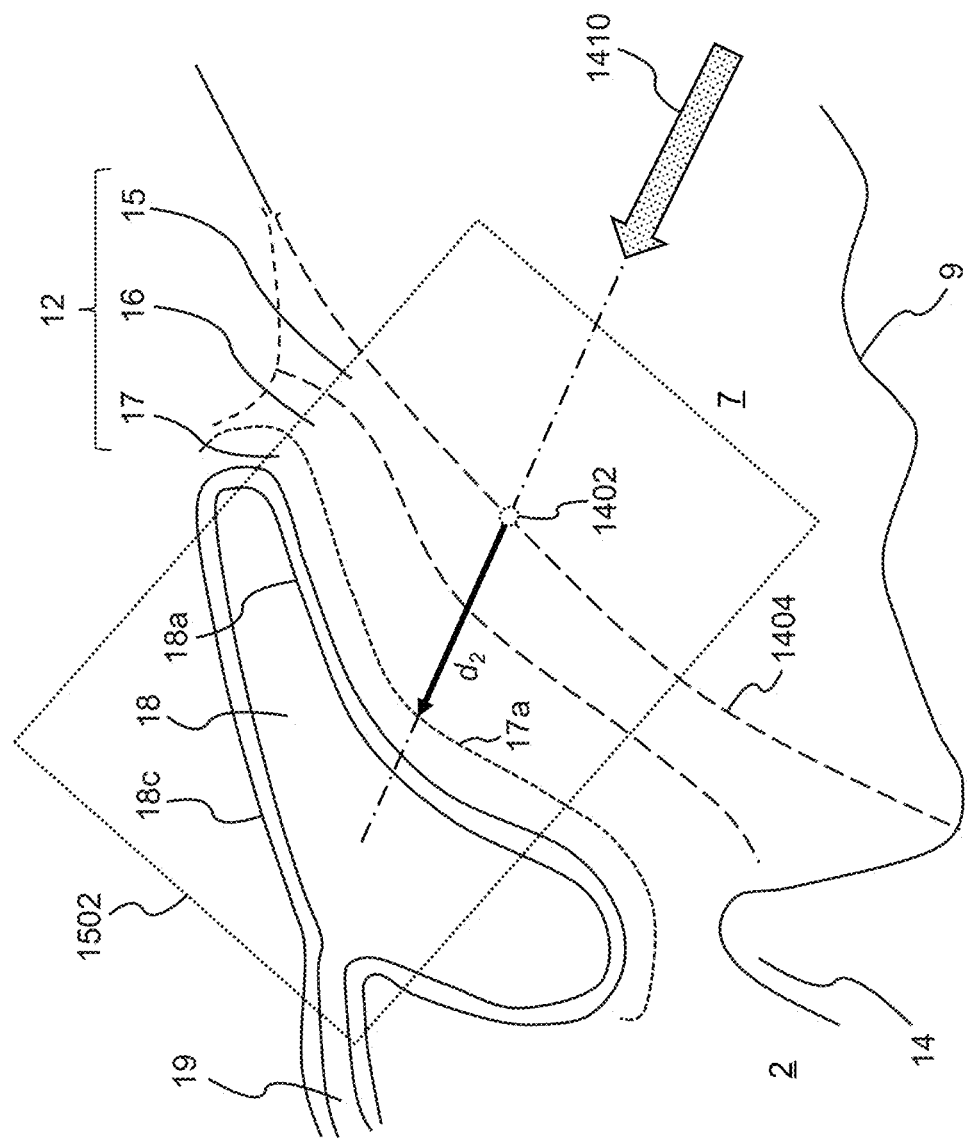
Figure 15D:
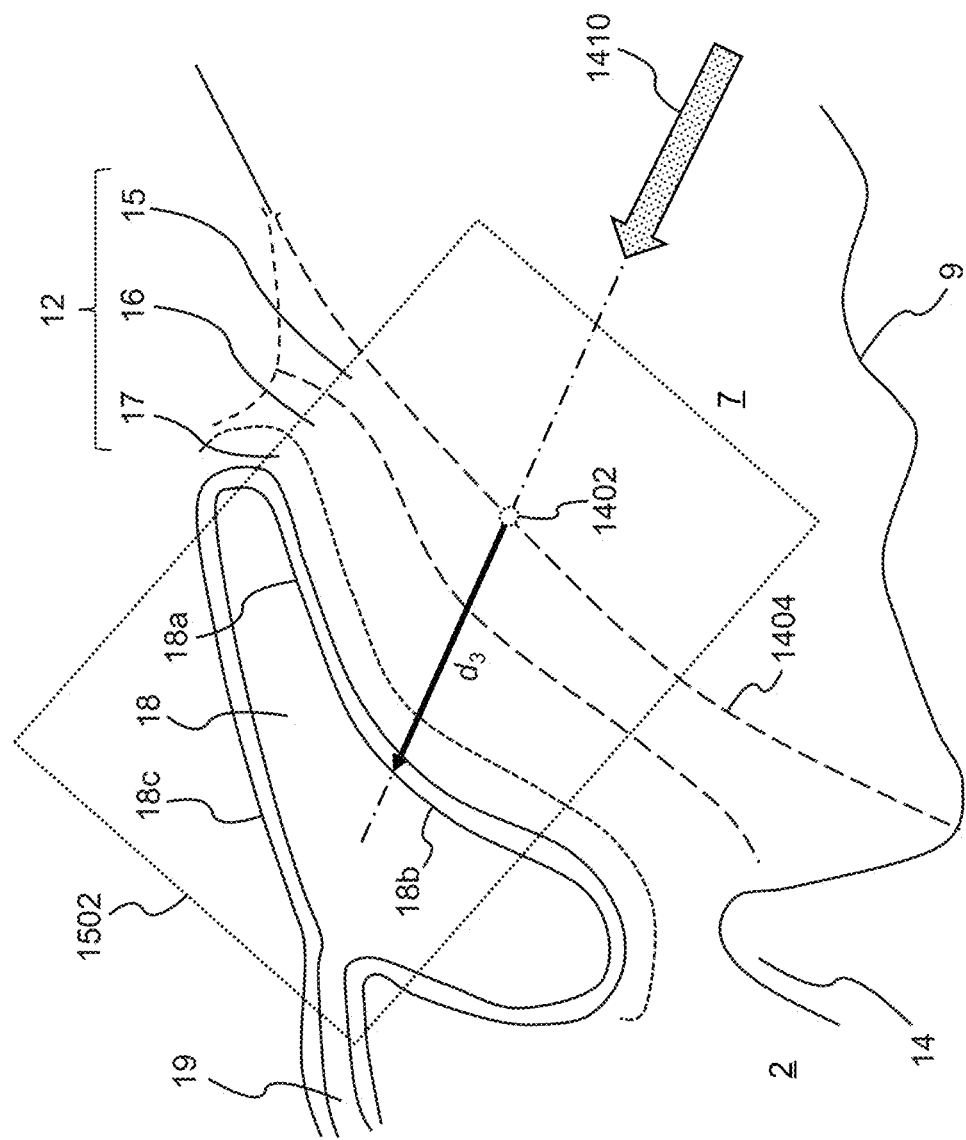

With reference to FIGS. 15B, 15C, and 15D, having determined the focus 1402 of the femtosecond laser beam 701 is at or on the target surface 1404, an OCT imaging apparatus 300 may be used to further detect or located locate target sub-surfaces of tissue relative to the target surface. To this end, an OCT image 1502 of the irido-corneal angle may be obtained by the OCT imaging apparatus 300. The OCT image 1502 may display tissue structures in a surgical field, including for example, a uveal meshwork 15, a corneoscleral meshwork 16, a juxtacanalicular tissue 17, a proximal surface or inner wall 18a of Schlemm's canal, a Schlemm's canal 18, a distal surface or outer wall 18c of Schlemm's canal, and a sclera 2. Based on these images, distances between a sub-surface and the target surface 1404 may be determined and recorded for future use during a treatment procedure. For example, in FIG. 15B a distance $d_1$ between the target surface 1404 and the outer surface 16a of the corneoscleral meshwork 16 may be determined. In FIG. 15C, a distance $d_2$ between the target surface 1404 and the outer surface 17a of the juxtacanalicular tissue 17 may be determined. In FIG. 15D, a distance $d_3$ between the target surface 1404 and the outer surface 18b of the inner wall 18a of Schlemm's canal may be determined. One or more of these determined distances d may define a parameter of a treatment plan. For example, with reference to FIG. 12, the distances d may define the thickness t of a volume of ocular tissue 60 to be treated.

Figure 16:
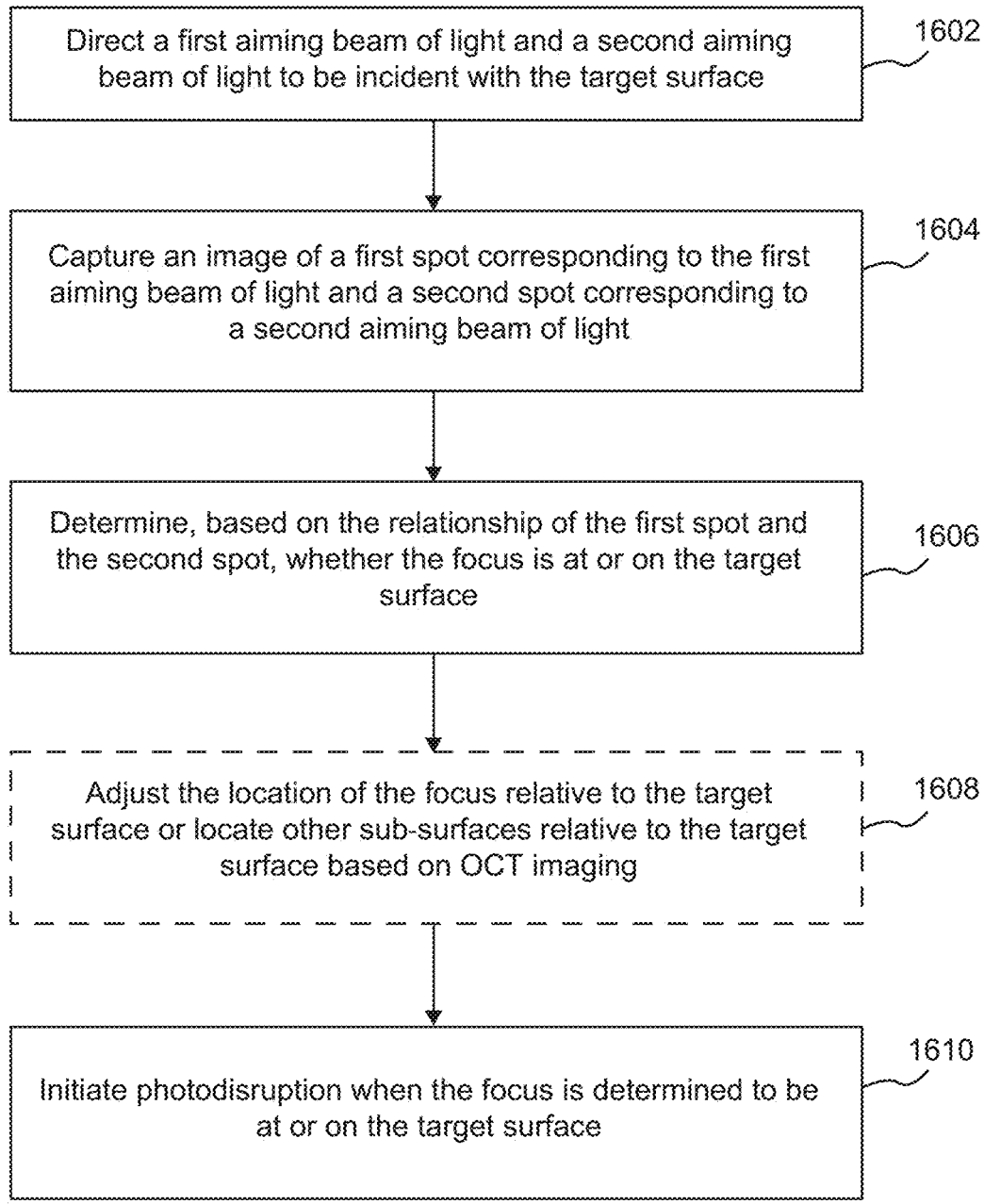
FIG. 16 is a flowchart of a method of locating a target structure of ocular tissue in an irido-corneal angle of an eye for photodisruption by a femtosecond laser.

FIG. 16 is a flowchart of a method of locating a target surface of ocular tissue in an irido-corneal angle of an eye for treatment by a laser. The target surface 1404 of ocular tissue may be, for example, the inner surface of the trabecular meshwork 12 facing the anterior chamber 7. While locating of the target surface is occurring, the laser is maintained at a power level insufficient to treat tissue while it is being directed toward the irido-corneal angle, and is typically maintained at this power level until the time laser treatment of tissue is initiated.

The method, which may be performed by the integrated surgical system 1000 of FIGS. 7-10B, begins at a point in a surgical procedure where access to the irido-corneal angle has been obtained. Systems and methods for accessing the irido-corneal angle are described in U.S. patent application Ser. No. 16/036,883, entitled Integrated Surgical System and Method for Treatment in the Irido-Corneal Angle of the Eye, the disclosure of which is hereby incorporated by reference.

At block 1602, the integrated surgical system 1000 directs a first aiming beam of light 1406 and a second aiming beam of light 1408 to be incident with the target surface 1404. The first aiming beam of light 1406 and the second aiming beam of light 1408 may respectively correspond to a beam of light 451a, 451b in the integrated surgical system of FIG. 8A or 8B.

The first aiming beam of light 1406 and the second aiming beam of light 1408 are aligned relative to each other and relative to a femtosecond laser beam 701 such that the first aiming beam of light and the second aiming beam of light intersect at a point 1412 corresponding to a focus 1402 of the femtosecond laser beam 1410. In one configuration, the intersection point of the first aiming beam of light 1406 and the second aiming beam of light 1408 is at a location that is the same as the location of the focus 1402 of the femtosecond laser beam. In another configuration, the intersection point of the first aiming beam of light 1406 and the second aiming beam of light 1408 is at a location different from the location of the focus 1402 of the femtosecond laser beam. For example, the intersection point may be slightly offset from and not at the exact same location as the focus. The first aiming beam of light 1406 and the second aiming beam of light 1408 each emit a wavelength of light at which the cornea and aqueous humor are transparent. In one configuration, the first aiming beam of light 1406 is characterized by a first wavelength and the second aiming beam of light 1408 is characterized by second wavelength different then the first wavelength. In another configuration, the first aiming beam of light 1406 and the second aiming beam of light 1408 are the same wavelength.

At block 1604, the integrated surgical system 1000 captures an image 1414a of a first spot 1416 corresponding to the first aiming beam of light 1406 and a second spot 1418 corresponding to a second aiming beam of light 1408. In cases where the first aiming beam of light 1406 and the second aiming beam of light 1408 are different wavelengths the spots 1416, 1418 are different colors. In cases where the first aiming beam of light 1406 and the second aiming beam of light 1408 are different wavelengths the spots 1416, 1418 are the same color.

At block 1606, a determination is made based on the relationship of the first spot 1416 and the second spot 1418 as to whether the focus 1402 is at or on the target surface 1404. Such determination may be made visually by a surgeon or automatically by the integrated surgical system 1000. In the case of surgeon determination, the integrated surgical system 1000 presents or displays an image 1414a, 1414b, 1414c of the target surface 1404 together with the first spot 1416 and the second spot 1418, from which the surgeon determines the location of the focus 1402 relative to the target surface 1404. In the case of automated system determination, algorithms executed by a processor in the control system 100 process images of the target surface 1404 together with the first spot 1416 and the second spot 1418 that are captured by the system to determine the location of the focus 1402 relative to the target surface 1404.

In either case, a positional relationship between the first spot 1416 and the second spot 1418 is detected, and the focus 1402 is determined, either visually by a surgeon or automatically by the integrated surgical system 1000, to be at the target surface 1404 based on a detection of an overlap or merger of the first spot 1416 and the second spot 1418. Otherwise, the focus 1402 is determine to be proximal the target surface 1404 or distal the target surface based on a detection of a separation between the first spot 1416 and the second spot 1418 and a corresponding positional arrangement among the first spot and the second spot.

For example, with reference to FIG. 14A, detection of a distance s between the first spot 1416 and the second spot 1418, with the second spot being above the first spot leads to a conclusion that the focus 1402 is located inside the anterior chamber 7 and proximal the target surface 1404. Accordingly, the integrated surgical system 1000, either automatically under processor control or under the control of a surgeon, advances the focus 1402 of the femtosecond laser beam 1410 in a distal direction corresponding a direction of propagation of the femtosecond laser. The focus 1402 may be advanced until the first spot 1416 and the second spot

1418 are determined, either automatically by a processor executing image processing algorithms or visually by a surgeon viewing an image 1414*a*, to overlap or merge into a single spot. Thereby indicating that the focus 1402 is at the target surface 1404.

With reference to FIG. 14B, detection of a distance s between the first spot 1416 and the second spot 1418, with the first spot being above the second spot leads to a conclusion that the focus 1402 is located inside of tissue and distal the target surface 1404. Accordingly, the integrated surgical system 1000, either automatically under processor control or under the control of a surgeon, advances the focus 1402 in a proximal direction corresponding a direction opposite the direction of propagation of the femtosecond laser beam 1410. The focus 1402 may be advanced until the first spot 1416 and the second spot 1418 are determined, either automatically by a processor executing image processing algorithms or visually by a surgeon viewing an image 1414*a*, to overlap or merge into a single spot. Thereby indicating that the focus 1402 is at the target surface 1404.

At block 1608, the integrated surgical system 1000 optionally enables adjusting the location of the focus 1402 relative to the target surface 1404 or the locating and marking of other sub-surfaces relative to the target surface based on OCT imaging. To this end, upon determining that the focus 1402 is at or on the target surface 1404 based on the relationship of the first spot 1416 and the second spot 1418, the target surface in located in an OCT image 1502 that includes an image of the focus. The position of the focus 1402 relative to the target surface 1404 as captured in the OCT image 1502 is adjusted, if needed, to more accurately place the focus on the surface.

Separate from the foregoing adjustment of the focus 1402, one or more OCT images 1502 may be analyzed to detect one or more target sub-surfaces beneath the target surface 1404. These sub-surfaces may be at the interface between the uveal meshwork 15, and the corneoscleral meshwork 16, or the interface between the corneoscleral meshwork and the juxtacanalicular tissue 17, or the interface between the juxtacanalicular tissue and the inner wall 18*a* of Schlemm's canal. Distances between one or more of the detected target sub-surfaces and the target surface are determined and recorded for future use. As previously mentioned, one or more of these determined distances d may define a parameter of a treatment plan. For example, with reference to FIG. 12, the distances d may define the thickness t of a volume of ocular tissue 60 to be treated.

At block 1610, photodisruption is initiated when the focus 1402 is determined to be at or on the target surface 1404. To this end, the power level of the femtosecond laser is increased to a power level sufficient to photodisrupt tissue and the focus is raster scanned in two dimensions to photodisrupt a sheet or layer of tissue.

Returning to block 1602, part of directing the first aiming beam of light 1406 and the second aiming beam of light 1408 to be incident with the target surface 1404 includes receiving the first aiming beam of light and the second aiming beam of light in an arrangement wherein the first aiming beam of light and the second aiming beam of light are parallel relative to each other and with respect to the femtosecond laser beam. In one configuration, receiving the first aiming beam of light 1406 and the second aiming beam of light 1408 in a parallel arrangement relative to each other and with respect to the femtosecond laser beam 1410 includes transmitting a single beam of light 451 from a single aiming beam source 452, and splitting the single beam of light into the first aiming beam of light 451*a* and the second aiming beam of light 451*b*. In another configuration, receiving the first aiming beam of light 1406 and the second aiming beam of light 1408 in a parallel arrangement relative to each other and with respect to the femtosecond laser beam includes transmitting the first aiming beam of light 451*a* from a first aiming beam source 452*a*, and transmitting the second aiming beam of light 451*b* from a second aiming beam source 452*b*.

Continuing with block 1602, directing the first aiming beam of light 1406 and the second aiming beam of light 1408 to be incident with the target surface 1404 further includes adjusting, through an objective lens, the first aiming beam of light 1406 and the second aiming beam of light 1408 to be non-parallel relative to each other and to intersect at the point 1412 corresponding to the focus 1402 of the femtosecond laser beam 1410. In one example, the target surface 1404 may be distal a cornea and adjusting the first aiming beam of light 1406 and the second aiming beam of light 1408 to be non-parallel relative to each other includes adjusting the first aiming beam of light to have a first angle of incidence relative to the cornea and the second aiming beam of light to have a second angle of incidence relative to the cornea that is different from the first angle of incidence.

With reference to FIGS. 7-10B, a surgical system 1000 for locating a target surface of ocular tissue in an irido-corneal angle of an eye for treatment by a laser in accordance with the method of FIG. 16 includes a laser source 200, a dual aiming beam apparatus 450, an optics subsystem, an imaging apparatus 400, and a control system 100 having a processor that executes algorithms that implement some features of the method. The surgical system 1000 may also include an OCT imaging apparatus 300.

The laser source 200 may be a femtosecond laser source configured to output a femtosecond laser beam 201. Alternatively, the laser source may be photodisruptive lasers, also known as photoionizing lasers, such as Nd:YAG or Nd:YLF lasers.

The dual aiming beam apparatus 450 is configured to transmit a first aiming beam of light 451*a* and a second aiming beam of light 451*b*. The first aiming beam of light 451*a* and the second aiming beam of light 451*b* each emit a wavelength of light at which the cornea and aqueous humor are transparent. The first aiming beam of light 451*a* is characterized by a first wavelength and the second aiming beam of light 451*b* is characterized by second wavelength. In one configuration the second wavelength is different than the first wavelength. In another configuration, the first wavelength and the second wavelength are the same.

In one configuration, as shown in FIG. 8B, the dual aiming beam apparatus 450 includes an aiming beam source 452 configured to transmit a single beam of light 451, and a first beam splitter 822 configured to split the single beam of light into the first aiming beam of light 451*a* and the second aiming beam of light 451*b* and direct the first aiming beam of light and the second aiming beam of light into the optical subsystem. In another configuration, as shown in FIG. 8C, the dual aiming beam apparatus 450 includes a first aiming beam source 452*a* configured to transmit the first aiming beam of light 451*a*, and a second aiming beam source 452*b* configured to transmit the second aiming beam of light 451*b*. In either of these configurations, an aiming beam source 452, 452*a*, 452*b* may be a Helium-Neon (He—Ne) laser operating at wavelengths at 543 nm, 594 nm, 604 nm, 612 nm, 633 nm, and 1150 nm. Alternatively, an aiming beam source 452, 452*a*, 452*b* may be a laser diode or light emitting diode (LEDs) operating in a range of wavelengths from 500 nm to 1200 nm. In either configuration, an aiming beam source 452, 452a, 452b may be configured to operate in a continuous wave (CW) mode or in a pulsed laser mode.

In another configuration, as shown in FIG. 8D, the dual aiming beam apparatus 450 includes an aiming beam source 452 configured to transmit a cone of light 856 and an aiming beam telescope 858 and a double aperture 860 configured to transform the cone of light 856 into the first aiming beam of light 451a and the second aiming beam of light 451b and direct the first aiming beam of light and the second aiming beam of light into the optical subsystem.

The optics subsystem is optically aligned with the laser source 200 and the dual aiming beam apparatus 450 to receive the femtosecond laser beam 201, the first aiming beam of light 451a, and the second aiming beam of light 451b. The optics subsystem includes a focusing objective 814 having an objective lens 830 configured to direct the first aiming beam of light 451c and the second aiming beam of light 451d to be incident with the target surface and to align the first aiming beam of light and the second aiming beam of light relative to each other and relative to the femtosecond laser beam 203 such that the first aiming beam of light and the second aiming beam of light intersect at a point 816 corresponding to a focus of the femtosecond laser beam.

The optics subsystem includes one or more optics components 809, 818, 828 configured to transmit the first aiming beam of light 451a, 451c and the second aiming beam of light 451b, 451d to the focusing objective 814 in an arrangement wherein the first aiming beam of light and the second aiming beam of light are parallel relative to each other and with respect to the femtosecond laser beam 203. To this end, a telescope 818 included in the optics subsystem receives the first aiming beam of light 451a and the second aiming beam of light 451b in a non-parallel arrangement. The telescope 818 is optically designed to output the beams of light 451c, 451d in a parallel arrangement. The focusing objective 814 is configured to adjust the first aiming beam of light 451c and the second aiming beam of light 451d to be non-parallel relative to each other and to intersect at the point 816 corresponding to the focus of the femtosecond laser beam 203. To this end, an objective lens 830 included in the focusing objective 814 receives the first aiming beam of light 451c and the second aiming beam of light 451d in a parallel arrangement. The objective lens 830 is optically designed to output the beams of light 451c, 451d in a non-parallel arrangement that will cause the beams of light to converge at the point 816.

The dual aiming beam apparatus 450 includes a focusing lens 824 aligned to receive the first aiming beam of light 451a and the second aiming beam of light 451b from one or more aiming beam sources 452, 452a, 452b and to transmit the first aiming beam of light and the second aiming beam of light. The optical subsystem includes a beam splitter 828 aligned to receive the first aiming beam of light 451a and the second aiming beam of light 451b from the dual aiming beam apparatus 450, and a telescope 818 aligned to receive the first aiming beam of light and the second aiming beam of light from the beam splitter. As previously mention, the telescope 818 is optically designed to output the beams of light 451c, 451d in a parallel arrangement. The dual aiming beam apparatus 450 includes an aperture 826 positioned in an optical path between the focusing lens 824 and the beam splitter 828. The aperture 826 is placed at a conjugate plane of the telescope 818. Those of skill in the art understand that conjugate planes are planes in which an image is formed. If a screen is placed on a conjugate plane of an optical system,
an image will appear sharp and "in focus". But if the screen is moved out of the conjugate place, an image will appear blurry and "out of focus". Considering the embodiment shown in FIG. 8B, camera 400 is observing an image at the point 816. Light emerging from the point 816 propagates through the focusing objective 814, reflects from the second dichroic mirror 809, and is focused by the telescope 818. An image is formed at the conjugate image plane 826. Working in the opposite direction, the light emerging from the conjugate image plane 826 will therefore form an image at the point 816.

The imaging apparatus 400 is optically aligned with the optics subsystem to capture an image 1414a, 1414b, 1414c of the irido-corneal angle including a first spot 1416 corresponding to the first aiming beam of light 451c and a second spot 1418 corresponding to a second aiming beam of light 451d. In one configuration, the imaging apparatus 400 includes an illumination source configured to output an illumination beam 401 of light in a visible spectra, and a video camera configured to provide an image of the target surface 1404 using a light output by the illumination source. The video camera may be configured to provide an image of the target surface using a range of wavelengths from 400 nm to 1200 nm. The imaging apparatus 400 may also include a microscope.

The surgical system 1000 includes a control system 100 that is coupled to the imaging apparatus 400. The control system 100 includes a processor that executes one or more image processing algorithms on images 1414a, 1414b, 1414c captured by the imaging apparatus 400. For example, the processor may process an image 1414a, 1414b, 1414c to detect a positional relationship between a first spot 1416 and a second spot 1418. The positional relationship may be characterized in terms of a distance s or separation between the spots 1416, 1418 and an arrangement of the spots. Based on this positional relationship, the processor may determine that a focus 1402 is at a target surface 1404 when the processor detects an overlap of the first spot 1416 and the second spot 1418. The processor may also determine that a focus 1402 is either proximal the target surface 1404 or distal the target surface based when the processor detects a separation between the first spot 1416 and the second spot 1418 and a corresponding positional relationship among the first spot and the second spot, e.g., which spot is above the other spot.

The control system 100 is also coupled to the laser source 200 and the optics subsystem. The processor of the control system 100 is configured to cause the focusing objective 814 to advance the focus 1402 in a distal direction corresponding a direction of propagation of the femtosecond laser beam 1410 when the focus is determined to be proximal the target surface 1404. This condition is shown in FIG. 14A. Conversely, the processor is configured to causes the focusing objective 814 to advance the focus 1402 in a proximal direction corresponding a direction opposite the direction of propagation of the femtosecond laser beam 1410 when the focus is determined to be distal the target surface 1404. This condition is shown in FIG. 14B. In either case, to advance the focus 1402 in the desired direction, one or more components, e.g., the objective lens 830, of the focusing objective 814 are moved. When the focus 1402 is determined to be at the target surface 1404, the processor of the control system 100 may cause the laser source to initiate laser treatment, e.g., photodisruption.

In surgical systems 100 having a OCT imaging apparatus 300 configured to output an OCT beam 301, the optics subsystem is optically aligned to receive the OCT beam. The optics system is also configured to direct the OCT beam 303 to be incident with the target surface 1404 and to be aligned with the first aiming beam of light 451c and the second aiming beam of light 451d and relative to the femtosecond laser beam 203 such that the OCT beam, the first aiming beam of light, and the second aiming beam of light intersect at a point 816 corresponding to the focus 1402 of the femtosecond laser beam 1410.

The control system 100 is also coupled to the OCT imaging apparatus 300. The control system 100 includes a processor that executes one or more image processing algorithms on images 1502 captured by the OCT imaging apparatus 300. For example, upon a determination based on the dual aiming beam apparatus 450 that a focus 1402 is at or on the target surface 1404, the processor executing image processing algorithms on an OCT image 1502 may locate the focus 1402 and the target surface 1404 in the OCT image, and determine if the focus is precisely placed on the target surface. If the focus 1402 is not precisely placed, as shown for example in FIG. 15A, the processor may control the focusing objective 814 to adjust the location of the focus until the focus is on the target surface 1404.

The processor of the control system 100 is also configured to executing image processing algorithms on one or more OCT images 1502 to detect one or more target sub-surfaces beneath the target surface 1404 and to determine distances between one or more of the detected target sub-surfaces, and the target surface 1404. For example, with reference to FIGS. 15B, 15C, and 15D, the target surface 1404 may be a surface of a trabecular meshwork facing an anterior chamber 7, and the one or more target sub-surfaces may be part of the uveal meshwork 15, the corneoscleral meshwork 16, the juxtacanalicular tissue 17, the proximal surface or inner wall 18a of Schlemm's canal, a Schlemm's canal 18, the distal surface or outer wall 18c of Schlemm's canal, and the sclera 2.

The various aspects of this disclosure are provided to enable one of ordinary skill in the art to practice the present invention. Various modifications to exemplary embodiments presented throughout this disclosure will be readily apparent to those skilled in the art. Thus, the claims are not intended to be limited to the various aspects of this disclosure but are to be accorded the full scope consistent with the language of the claims. All structural and functional equivalents to the various components of the exemplary embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

It is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A system for locating a target surface of ocular tissue in an irido-corneal angle of an eye for photodisruption by a laser, the system comprising:
    a laser source configured to output a laser beam;
    a dual aiming beam apparatus configured to transmit a first aiming beam of light and a second aiming beam of light;
    an optics subsystem optically aligned with the laser source and the dual aiming beam apparatus to receive the laser beam, the first aiming beam of light, and the second aiming beam of light, the optics subsystem comprising a focusing objective configured to:
        direct the laser beam, the first aiming beam of light, and the second aiming beam of light along an angled beam path through a cornea and an anterior chamber of the eye, to be incident with the target surface of ocular tissue in the irido-corneal angle of the eye, and
        align the first aiming beam of light and the second aiming beam of light relative to each other and relative to the laser beam such that the first aiming beam of light and the second aiming beam of light intersect at a point corresponding to a focus of the laser beam; and
    an imaging apparatus optically aligned with the optics subsystem to capture an image of the irido-corneal angle including a first spot corresponding to the first aiming beam of light and a second spot corresponding to a second aiming beam of light.

2. The system of claim 1, wherein:
    the optics subsystem comprises one or more optics components configured to transmit the first aiming beam of light and the second aiming beam of light to the focusing objective in an arrangement wherein the first aiming beam of light and the second aiming beam of light are parallel relative to each other and with respect to the laser beam; and
    the focusing objective is configured to adjust the first aiming beam of light and the second aiming beam of light to be non-parallel relative to each other and to intersect at the point corresponding to the focus of the laser beam.

3. The system of claim 2, wherein:
    the dual aiming beam apparatus comprises a focusing lens aligned to receive the first aiming beam of light and the second aiming beam of light from one or more aiming beam sources, and to transmit the first aiming beam of light and the second aiming beam of light, and
    the optical subsystem comprises a beam splitter aligned to receive the first aiming beam of light and the second aiming beam of light from the dual aiming beam apparatus, and a telescope aligned to receive the first aiming beam of light and the second aiming beam of light from the beam splitter.

4. The system of claim 3, wherein the beam splitter is in an optical path between the imaging apparatus and the focusing objective.

5. The system of claim 3, wherein the dual aiming beam apparatus comprises an aperture positioned between the focusing lens and the beam splitter and placed at a conjugate plane of the telescope.

6. The system of claim 2, wherein the dual aiming beam apparatus comprises:
    an aiming beam source configured to transmit a single beam of light; and
    a first beam splitter configured to split the single beam of light into the first aiming beam of light and the second aiming beam of light and direct the first aiming beam of light and the second aiming beam of light into the optical subsystem.

7. The system of claim 2, wherein the dual aiming beam apparatus comprises:
a first aiming beam source configured to transmit the first aiming beam of light; and
a second aiming beam source configured to transmit the second aiming beam of light.

8. The system of claim 2, wherein:
the dual aiming beam apparatus comprises an aiming beam telescope aligned to receive a cone of light from an aiming beam source, and configured to transform the cone of light into a pair of parallel beams of light, and a double aperture aligned to receive the pair of parallel beams of light and to transmit the first aiming beam of light and the second aiming beam of light; and
the optical subsystem comprises a beam splitter aligned to receive the first aiming beam of light and the second aiming beam of light from the double aperture.

9. The system of claim 8, wherein the beam splitter is in an optical path between the laser source and the focusing objective.

10. The system of claim 1, wherein the first aiming beam of light is characterized by a first wavelength and the second aiming beam of light is characterized by second wavelength different then the first wavelength.

11. The system of claim 1, wherein the dual aiming beam apparatus comprises one or more aiming beam sources comprised of a Helium-Neon (He—Ne) laser operating at wavelengths at 543 nm, 594 nm, 604 nm, 612 nm, 633 nm, and 1150 nm.

12. The system of claim 1, wherein the dual aiming beam apparatus comprises one or more aiming beam sources comprised of laser diodes or light emitting diodes (LEDs) operating in a range of wavelengths from 400 nm to 1200 nm.

13. The system of claim 1, wherein the dual aiming beam apparatus comprises one or more aiming beam sources configured to operate in a continuous wave (CW) mode or in a pulsed laser mode.

14. The system of claim 1, wherein the imaging apparatus comprises:
an illumination source configured to output an illumination beam of light in a visible spectra; and
a video camera configured to provide an image of the target surface using a light output by the illumination source.

15. The system of claim 1, wherein the imaging apparatus comprises a video camera configured to provide an image of the target surface using a range of wavelengths from 400 nm to 1200 nm.

16. The system of claim 15, wherein the imaging apparatus comprises a microscope.

17. The system of claim 1, wherein the intersection point of the first aiming beam of light and the second aiming beam of light is at a location that is the same as the location of the focus of the laser beam.

18. The system of claim 1, wherein the intersection point of the first aiming beam of light and the second aiming beam of light is at a location different from the location of the focus of the laser beam.

19. The system of claim 1, further comprising a processor coupled to the imaging apparatus, wherein the processor is configured to:
detect a positional relationship between the first spot and the second spot;
determine that the focus is at the target surface based on a detection of an overlap of the first spot and the second spot; and
determine that the focus is either proximal the target surface or distal the target surface based on a detection of a separation between the first spot and the second spot and a corresponding positional relationship among the first spot and the second spot.

20. The system of claim 19, wherein the processor is coupled to the laser source and is further configured to cause the laser source to initiate photodisruption when the focus is determined to be at the target surface.

21. The system of claim 19, wherein the processor is coupled to the optics subsystem and is further configured to cause the focusing objective to advance the focus in a distal direction corresponding a direction of propagation of the laser when the focus is determined to be proximal the target surface, and to advance the focus in a proximal direction corresponding a direction opposite the direction of propagation of the laser when the focus is determined to be distal the target surface.

22. The system of claim 19, wherein the processor is configured to determine the positional relationship between the first spot and the second spot by being further configured to analyze the image of the first spot and the second spot.

23. The system of claim 1, further comprising an OCT imaging apparatus configured to output an OCT beam, wherein the optics subsystem is optically aligned to receive the OCT beam and configured to direct the OCT beam along the angled beam path through the cornea and the anterior chamber of the eye, to be incident with the target surface and to be aligned with the first aiming beam of light and the second aiming beam of light and relative to the laser beam such that the OCT beam, the first aiming beam of light, and the second aiming beam of light intersect at a point corresponding to the focus of the laser beam.

24. A method of locating a target surface of ocular tissue in an irido-corneal angle of an eye for photodisruption by a laser, the method comprising:
directing a laser beam, a first aiming beam of light, and a second aiming beam of light along an angled beam path through a cornea and an anterior chamber of the eye, to be incident with the target surface of ocular tissue in the irido-corneal angle of the eye, wherein the first aiming beam of light and the second aiming beam of light are aligned relative to each other and relative to the laser beam such that the first aiming beam of light and the second aiming beam of light intersect at a point corresponding to a focus of the laser beam; and
capturing an image of a first spot corresponding to the first aiming beam of light and a second spot corresponding to a second aiming beam of light.

25. The method of claim 24, wherein directing a first aiming beam of light and a second aiming beam light comprises:
receiving the first aiming beam of light and the second aiming beam of light in an arrangement wherein the first aiming beam of light and the second aiming beam of light are parallel relative to each other and with respect to the laser beam; and
adjusting the first aiming beam of light and the second aiming beam of light to be non-parallel relative to each other and to intersect at the point corresponding to the focus of the laser beam.

26. The method of claim 25, wherein the target surface is distal a cornea and adjusting the first aiming beam of light and the second aiming beam of light to be non-parallel relative to each other comprises adjusting the first aiming beam of light the first aiming beam of light to have a first angle of incidence relative to the cornea and the second aiming beam of light to have a second angle of incidence relative to the cornea that is different from the first angle of incidence.

27. The method of claim 25, wherein receiving the first aiming beam of light and the second aiming beam of light in an arrangement wherein the first aiming beam of light and the second aiming beam of light are parallel relative to each other and with respect to the laser beam comprises:
transmitting a single beam of light from a single aiming beam source; and
splitting the single beam of light into the first aiming beam of light and the second aiming beam of light.

28. The method of claim 25, wherein receiving the first aiming beam of light and the second aiming beam of light in an arrangement wherein the first aiming beam of light and the second aiming beam of light are parallel relative to each other and with respect to the laser beam comprises:
transmitting the first aiming beam of light from a first aiming beam source; and
transmitting the second aiming beam of light from a second aiming beam source.

29. The method of claim 25, wherein receiving the first aiming beam of light and the second aiming beam of light in an arrangement wherein the first aiming beam of light and the second aiming beam of light are parallel relative to each other and with respect to the laser beam comprises:
transmitting a cone of light from a single aiming beam source; and
transforming the cone of light into the first aiming beam of light and the second aiming beam of light.

30. The method of claim 24, wherein the first aiming beam of light is characterized by a first wavelength and the second aiming beam of light is characterized by second wavelength different then the first wavelength.

31. The method of claim 24, further comprising:
detecting a positional relationship between the first spot and the second spot;
determining that the focus is at the target surface based on a detection of an overlap of the first spot and the second spot; and
determining that the focus is either proximal the target surface or distal the target surface based on a detection of a separation between the first spot and the second spot and a corresponding positional relationship among the first spot and the second spot.

32. The method of claim 31, further comprising initiating photodisruption when the focus is determined to be at the target surface.

33. The method of claim 31, further comprising:
advancing the focus in a distal direction corresponding a direction of propagation of the laser when the focus is determined to be proximal the target surface; and
advancing the focus in a proximal direction corresponding a direction opposite the direction of propagation of the laser when the focus is determined to be distal the target surface.

34. The method of claim 31, further comprising presenting an image of the target surface together with the first spot and the second spot.

35. The method of claim 31, further comprising:
upon determining that the focus is at the target surface, locating the target surface in an OCT image;
analyzing one or more OCT images to detect one or more target sub-surfaces beneath the target surface; and
for one or more of the one or more detected target sub-surfaces, determine a distance between the target surface and the target sub-surface.

36. The method of claim 35, wherein the target surface is a surface of a trabecular meshwork facing an anterior chamber, and the one or more target sub-surfaces comprises one of a uveal meshwork, a corneoscleral meshwork, a juxtacanalicular tissue, a proximal surface of Schlemm's canal, a Schlemm's canal, a distal surface of Schlemm's canal, and a sclera.

37. A system for locating a target surface of ocular tissue in an irido-corneal angle of an eye for photodisruption by a laser, the system comprising:
a laser source configured to output a laser beam;
a dual aiming beam apparatus configured to transmit a first aiming beam of light and a second aiming beam of light;
an OCT imaging apparatus configured to output an OCT beam and optically aligned to capture one or more OCT images of the irido-corneal angle;
an optics subsystem optically aligned with the laser source, the dual aiming beam apparatus, and the OCT imaging apparatus to receive the laser beam, the first aiming beam of light, the second aiming beam of light, and the OCT beam, the optics subsystem comprising a focusing objective configured to:
direct the laser beam, the first aiming beam of light, the second aiming beam of light, and the OCT beam along an angled beam path through a cornea and an anterior chamber of the eye, to be incident with the target surface of ocular tissue in the irido-corneal angle of the eye, and
align the first aiming beam of light, the second aiming beam of light and the OCT beam relative to each other and relative to the laser beam such that the first aiming beam of light, the second aiming beam of light, and the OCT beam intersect at a point corresponding to a focus of the laser beam; and
an imaging apparatus optically aligned with the optics subsystem to capture an image of the irido-corneal angle including a first spot corresponding to the first aiming beam of light and a second spot corresponding to a second aiming beam of light.

38. The system of claim 37, further comprising a processor coupled to the OCT imaging apparatus and the imaging apparatus, wherein the processor is configured to:
detect a positional relationship between the first spot and the second spot;
initially determine that the focus is at or on the target surface based on a detection of an overlap of the first spot and the second spot;
determine a location of the focus relative to the target surface based on one or more OCT images; and
adjust the location of the focus when the focus is determined to not be on the target surface.

39. The system of claim 38, wherein the processor is further configured to
upon a determination that the focus is at the target surface, locate the target surface in an OCT image;
analyze one or more OCT images to detect one or more target sub-surfaces beneath the target surface; and
for one or more of the detected target sub-surfaces, determine a distance between the target surface and the target sub-surface.

40. The system of claim 39, wherein the target surface is a surface of a trabecular meshwork facing an anterior chamber, and the one or more target sub-surfaces comprises one of a uveal meshwork, a corneoscleral meshwork, a juxtacanalicular tissue, a proximal surface of Schlemm's canal, a Schlemm's canal, a distal surface of Schlemm's canal, and a sclera.

41. A method of locating a target surface of ocular tissue in an irido-corneal angle of an eye for photodisruption by a laser, the method comprising:

directing a laser beam, an OCT beam, a first aiming beam of light, and a second aiming beam of light along an angled beam path through a cornea and an anterior chamber of the eye, to be incident with the target surface of ocular tissue in the irido-corneal angle of the eye, wherein the OCT beam, the first aiming beam of light and the second aiming beam of light are aligned relative to each other and relative to a laser beam such that the OCT beam, the first aiming beam of light and the second aiming beam of light intersect at a point corresponding to a focus of the laser beam;

capturing an image of a first spot corresponding to the first aiming beam of light and a second spot corresponding to a second aiming beam of light; and capturing one or more OCT images of the irido-corneal angle.

42. The method of claim 41, further comprising:

detecting a positional relationship between the first spot and the second spot;

initially determining that the focus is at or on the target surface based on a detection of an overlap of the first spot and the second spot;

determining a location of the focus relative to the target surface based on one or more OCT images; and adjusting the location of the focus when the focus is determined to not be on the target surface.

43. The method of claim 42, further comprising:

upon a determination that the focus is on the target surface, analyzing one or more OCT images to detect one or more target sub-surfaces beneath the target surface; and for one or more of the detected target sub-surfaces, determining a distance between the target surface and the target sub-surface.

* * * * *